(12) United States Patent
Coombs et al.

(10) Patent No.: US 12,121,539 B2
(45) Date of Patent: Oct. 22, 2024

(54) CHIMERIC ANTIGEN RECEPTORS AND USES THEREOF

(71) Applicant: BIOSCEPTRE (AUST) PTY LTD, North Ryde (AU)

(72) Inventors: Justin Taylor Coombs, Wattle Park (AU); Simon Charles Barry, Longwood (AU); Timothy John Sadlon, Maylands (AU)

(73) Assignee: BIOSCEPTRE (AUST) PTY LTD, North Ryde (AU)

( * ) Notice: Subject to any disclaimer, the term of this patent is extended or adjusted under 35 U.S.C. 154(b) by 581 days.

(21) Appl. No.: 15/759,046

(22) PCT Filed: Sep. 10, 2016

(86) PCT No.: PCT/AU2016/050851
§ 371 (c)(1),
(2) Date: Mar. 9, 2018

(87) PCT Pub. No.: WO2017/041143
PCT Pub. Date: Mar. 16, 2017

(65) Prior Publication Data
US 2019/0365805 A1 Dec. 5, 2019

(30) Foreign Application Priority Data
Sep. 11, 2015 (AU) .................. 2015903719

(51) Int. Cl.
| | |
|---|---|
| *A61K 35/17* | (2015.01) |
| *C07K 14/705* | (2006.01) |
| *C07K 14/715* | (2006.01) |
| *C07K 14/725* | (2006.01) |
| *C07K 14/735* | (2006.01) |
| *C07K 16/28* | (2006.01) |
| *C12N 5/0786* | (2010.01) |
| *C07K 19/00* | (2006.01) |

(52) U.S. Cl.
CPC .......... *A61K 35/17* (2013.01); *C07K 14/7051* (2013.01); *C07K 14/70521* (2013.01); *C07K 14/70535* (2013.01); *C07K 14/70578* (2013.01); *C07K 14/715* (2013.01); *C07K 16/28* (2013.01); *C12N 5/0645* (2013.01); *C07K 19/00* (2013.01); *C07K 2317/622* (2013.01); *C07K 2319/02* (2013.01); *C07K 2319/03* (2013.01); *C07K 2319/30* (2013.01); *C07K 2319/33* (2013.01); *C07K 2319/60* (2013.01)

(58) Field of Classification Search
None
See application file for complete search history.

(56) References Cited

U.S. PATENT DOCUMENTS

| | | |
|---|---|---|
| 7,183,064 B1 | 2/2007 | Slater et al. |
| 7,326,415 B2 | 2/2008 | Barden et al. |
| 7,531,171 B2 | 5/2009 | Barden et al. |
| 7,888,473 B2 | 2/2011 | Barden et al. |
| 8,067,550 B2 | 11/2011 | Barden et al. |
| 8,080,635 B2 | 12/2011 | Barden et al. |
| 8,293,491 B2 | 10/2012 | Gidley-Baird et al. |
| 8,399,617 B2 | 3/2013 | Barden et al. |
| 8,597,643 B2 | 12/2013 | Barden et al. |
| 8,658,385 B2 | 2/2014 | Gidley-Baird et al. |
| 8,709,425 B2 | 4/2014 | Barden et al. |
| 8,835,609 B2 | 9/2014 | Barden et al. |
| 8,840,186 B2 | 9/2014 | Samain |
| 9,127,059 B2 | 9/2015 | Barden et al. |
| 9,181,320 B2 | 11/2015 | Barden et al. |
| 9,328,155 B2 | 5/2016 | Barden et al. |
| 9,428,587 B2 | 8/2016 | Barden et al. |
| 9,562,094 B2 | 2/2017 | Barden et al. |
| 9,566,318 B2 | 2/2017 | Barden et al. |
| 9,663,584 B2 | 5/2017 | Barden et al. |
| 9,688,771 B2 | 6/2017 | Barden et al. |
| 10,053,508 B2 | 8/2018 | Barden et al. |
| 10,232,025 B2 | 3/2019 | Barden et al. |
| 10,238,716 B2 | 3/2019 | Barden et al. |
| 10,245,308 B2 | 4/2019 | Barden et al. |
| 2004/0067542 A1 | 4/2004 | Barden et al. |
| 2004/0067967 A1 | 4/2004 | Barden et al. |
| 2007/0248963 A1 | 10/2007 | Slater et al. |
| 2008/0227122 A1 | 9/2008 | Barden et al. |
| 2010/0036101 A1 | 2/2010 | Gidley-Baird et al. |

(Continued)

FOREIGN PATENT DOCUMENTS

| | | |
|---|---|---|
| WO | WO-2001/006259 A1 | 1/2001 |
| WO | WO-2002/057306 A1 | 7/2002 |

(Continued)

OTHER PUBLICATIONS

Gade et al (Cancer Res 2005, 65(19):9080-9088).*
Barden et al., "Non-functional P2X7: A Novel and Ubiquitous Target in Human Cancer," Journal of Clinical & Cellular Immunology, 5: 4 (2014).
International Search Report for International Application No. PCT/AU2016/050851 mailed Nov. 28, 2016.
Nesselhut et al., "NfP2X7, A Novel Target for Immune Therapeutic Approaches in Cancer Treatment," Journal of Clinical Oncology, 31(15): Abstract 3094 (2013).

(Continued)

*Primary Examiner* — Amy E Juedes
*Assistant Examiner* — Brian Hartnett
(74) *Attorney, Agent, or Firm* — Foley Hoag LLP; Brendan T. Jones; Mi Cai

(57) ABSTRACT

The present invention relates to chimeric antigen receptors (CARs) directed to cells expressing a dysfunctional or non-functional P2X purinoceptor 7 receptor. Further provided are methods of targeting neoplastic cells and tumours expressing a dysfunctional or non-functional P2X purinoceptor 7 receptor and methods of treating and preventing cancer is a subject.

29 Claims, 30 Drawing Sheets

Specification includes a Sequence Listing.

(56) References Cited

U.S. PATENT DOCUMENTS

| | | | |
|---|---|---|---|
| 2011/0111431 A1 | 5/2011 | Slater et al. | |
| 2012/0282278 A1* | 11/2012 | Barden | A61P 35/00 |
| | | | 536/23.53 |
| 2013/0273085 A1 | 10/2013 | Barden et al. | |
| 2014/0323693 A1 | 10/2014 | Barden et al. | |
| 2017/0327592 A1 | 11/2017 | Barden et al. | |
| 2018/0037650 A1 | 2/2018 | Barden | |
| 2019/0224290 A1 | 7/2019 | Barden et al. | |
| 2021/0038649 A1 | 2/2021 | Coombs et al. | |
| 2022/0089718 A1 | 3/2022 | Bandara et al. | |

FOREIGN PATENT DOCUMENTS

| | | | |
|---|---|---|---|
| WO | WO-2003/020762 A1 | 3/2003 | |
| WO | WO-2008/043145 A1 | 4/2008 | |
| WO | WO-2008/043146 A1 | 4/2008 | |
| WO | WO-2009/033233 A1 | 3/2009 | |
| WO | WO-2009/033234 A1 | 3/2009 | |
| WO | WO-2010/000041 A1 | 1/2010 | |
| WO | WO-2011/020155 A1 | 2/2011 | |
| WO | WO-2011/075789 A1 | 6/2011 | |
| WO | WO-2012/031333 A1 | 3/2012 | |
| WO | WO-2012/079000 A1 | 6/2012 | |
| WO | WO-2012/082841 A2 | 6/2012 | |
| WO | WO-2013/003895 A1 | 1/2013 | |
| WO | WO-2014/055657 A1 | 4/2014 | |
| WO | WO-2015121454 A1 * | 8/2015 | A61K 35/17 |
| WO | WO-2016/090369 A1 | 6/2016 | |
| WO | WO-2016/123143 A1 | 8/2016 | |
| WO | WO-2016/154683 A1 | 10/2016 | |
| WO | WO-2017/041143 A1 | 3/2017 | |
| WO | WO-2017/181001 A1 | 10/2017 | |
| WO | WO-2018/017649 A1 | 1/2018 | |
| WO | WO-2018/064626 A1 | 4/2018 | |
| WO | WO-2018/071959 A1 | 4/2018 | |
| WO | WO-2021/019222 A1 | 2/2021 | |

OTHER PUBLICATIONS

Pergram et al., "Tumor-targeted T Cells Modified to Secrete IL-12 Eradicate Systemic Tumors without Need for Prior Conditioning," Blood, 119(18): 4133-4141 (2012).

Stephan et al., "T Cell-Encoded CD80 and 4-1BBL Induce Auto- and Transcostimulation, Resulting in Potent Tumor Rejection," Nature Medicine, 13(12): 1440-1449 (2007).

Supplementary Search Report issued by the European Patent Office in corresponding Application No. EP 16843305 completed Jan. 22, 2019.

Hillerdal et al., "Chimeric Antigen Receptor-Engineered T Cells for the Treatment of Metastatic Prostate Cancer," BioDrugs, 29: 75-89 (2015).

Hudecek et al., "The non-signaling extracellular spacer domain of chimeric antigen receptors is decisive for in vivo antitumor activity," Cancer Immunology Research, 3(2): 20 pages (2015).

International Search Report and Written Opinion for International Application No. PCT/AU2019/050487 dated Jul. 19, 2019.

Kunkele et al., "Functional Tuning of CARs Reveals Signlaing Threshold above Which CD8+ CTL Antitumor Potency Is Attenuated due to Cell Fas-FasL-Dependent AICD," Cancer Immunology Research, 3(4): 368-379 (2015).

Nakazawa et al., "Genetically modified T-cell therapy using chimeric antigen receptor (CAR)," Shinshu Medical Journal, 61(4):197-203 (2013).

Li et al., "Increasing the safety and efficacy of chimeric antigen receptor T cell therapy," Protein Cell, 8(8):573-589 (2017).

Moot et al., "Genetic engineering of chimeric antigen receptors using lamprey derived variable lymphocyte receptors," Molecular Therapy Oncolytics, 3:16026 (2016).

Newick et al., "Chimeric antigen receptor T-cell therapy for solid tumors," Molecular Therapy Oncolytics, 3:16006 (2016).

Raikar et al., "Development of chimeric antigen receptors targeting T-cell malignancies using two structurally different anti-CD5 antigen binding domains in NK and CRISPR-edited T cell lines," Oncoimmunology, 7(3):e1407898 (2018).

Srivastava et al., "Engineering CART-T cells: Design concepts," Trends in Immunology, 36(8):494-502 (2015).

Wang et al., "Current status and perspectives of chimeric antigen receptor modified T cells for cancer treatment," Protein Cell, 8(12):896-925 (2017).

National Cancer Institute Webpage "CAR T Cells: Engineering Patients' Immune Cells to Treat Their Cancers," retrieved online <https://www.cancer.gov/about-cancer/treatment/research/car-t-cells>: 9 pages (2019).

Barden et al., "Specific detection of non-functional human P2X(7) receptors in HEK293 cells and B-lymphocytes", FEBS Lett. Mar. 13;538(1-3):159-62. doi: 10.1016/s0014-5793(03)00172-8 (2003).

Keating et al., "StoneHinge: Hinge prediction by network analysis of individual protein structures", Protein Sci. Feb. 18(2):359-71. doi: 10.1002/pro.38 (2009).

Li et al., "Association of a polymorphism in the P2X7 gene with tuberculosis in a Gambian population", *The Journal of infectious diseases* 186.10: 1458-1462 (2002).

Xu et al., "The basics of CAR T design and challenges in immunotherapy of solid tumors—Ovarian cancer as a model", Hum Vaccin Immunother. Jul. 3;13(7):1548-1555. doi: 10.1080/21645515.2017.1291473 (2017).

Adinolfi et al., "Accelerated Tumor Progression in Mice Lacking the ATP Receptor P2X7", Cancer Research, 75 (4) Feb. 15, 2015, pp. 635-644.

Delprado et al., "Non-Functional P2X7: A Novel and Ubiquitous Target in Human Cancer", Journal of Clinical & Cellular Immunology vol. 5(4) (2014).

Di Virgilio et al., "Purinergic P2X7 receptor: a pivotal role in inflammation and immunomodulation," *Drug Development Research* 45.3 4: 207-213 (1998).

Goel et al., "Plasticity within the Antigen-Combining Site May Manifest as Molecular Mimicry in the Humoral Immune Response", J Immunol 173 (12): 7358-7367 (2004).

Miller et al., "The role of the P2X7 receptor in infectious diseases", *PLoS pathogens* 7.11: e1002212 (2011).

National Institute of Health, "CAR T Cells: Engineering Patients' Immune Cells to Treat Their Cancers," National Cancer Institute, retrieved Nov. 20, 2023.

Rabia et al., "Understanding and overcoming trade-offs between antibody affinity,specificity, stability and solubility", Biochemical Engineering Journal 137: 365-374 (2018).

Townsend et al., "Significant Differences in Physiochemical Properties of Human Immunoglobulin Kappa and Lambda CDR3 Regions", Frontiers in Immunology vol. 7(388), (2016).

Wiley et al., "An lle-568 to Asn polymorphism prevents normal trafficking and function of the human P2X7 receptor", *Journal of Biological Chemistry* 278.19: 17108-17113 (2003).

Yip et al., "Autocrine regulation of T-cell activation by ATP release and P2X7 receptors", *The FASEB Journal* 23.6: 1685-1693 (2009).

* cited by examiner

BLIV-CAR-short hinge

BLIV-CAR-long hinge

FIGURE 5
A  Transfection of 293T cell with BLIV-CAR-short hinge
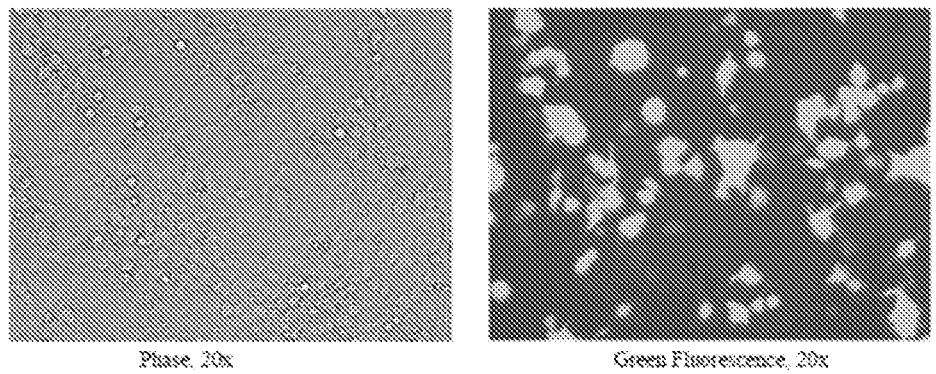
Phase, 20x  Green Fluorescence, 20x
B  Tranduction of 293T cell with BLIV-CAR-short hinge
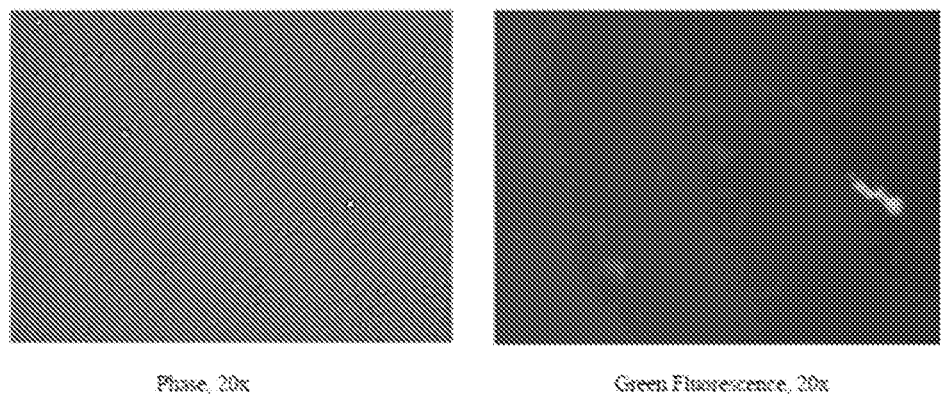
Phase, 20x  Green Fluorescence, 20x FIGURE 6
A
Transfection of 293T cell with BLIV-CAR-long hinge
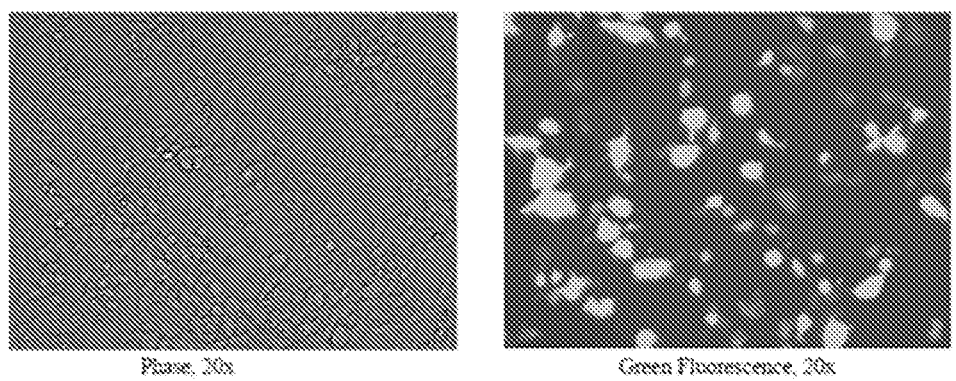
B
Transduction of 293T cell with BLIV-CAR-long hing
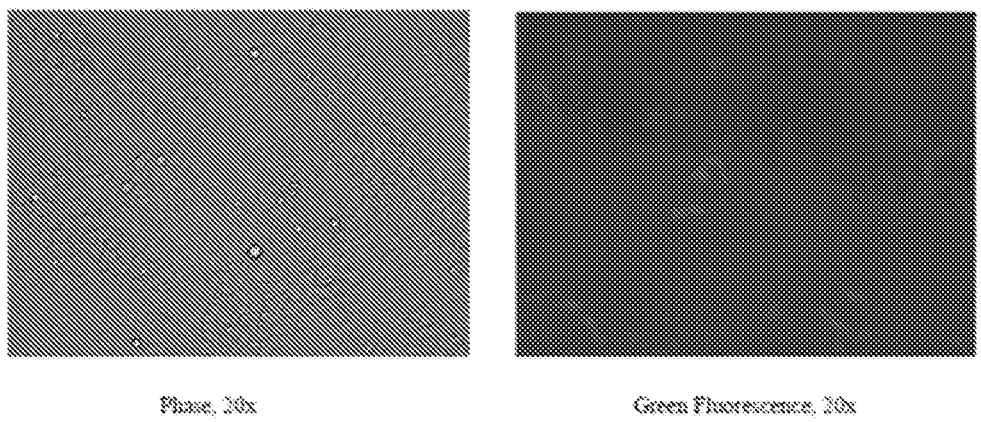

```
                                                                      Ig k-chain leader sequence
                                                    ┌─────────────────────────────────────────────────────────────┐
721  CTTGGGGATA TCCACC ATG GAG ACA GAC ACA CTC CTG CTA TGG GTA CTG CTG
                       Met Glu Thr Asp Thr Leu Leu Leu Trp Val Leu Leu
                                                              ├──────────
                                                              hemagglutinin A epitope
               SfiI            BglII        XmaI│SmaI                        SacII       PstI│SalI│AccI
773  CTC TGG GTT CCA GGT TCC ACT GGT GAC TAT CCA TAT GAT GTT CCA GAT
     Leu Trp Val Pro Gly Ser Thr Gly Asp Tyr Pro Tyr Asp Val Pro Asp
     ──────┤

821  TAT GCT GGG GCC CAG CCG GCC A GATCTCCCCGG GATCCCGCGG CTGCAGGTC GAC
     Tyr Ala
         ├────────
         myc epitope
                                                                  ┌─PDGFR transmembrane domain (5' end)
874  GAA CAA AAA CTC ATC TCA GAA GAG GAT CTG AATGCTGTGG GCCAGGACAC
     Glu Gln Lys Leu Ile Ser Glu Glu Asp Leu …
                                 ─────────────┤

924  GCAGGAGGTC ATCGGTGTGC CACACTCCTT GCCCCTTAAG GTGGTGGTGA TCTCAGCCAT

984  CCTGGCCCTG GTGGTGCTCA CCATCATCTC CCTTATCATC CTCATCATGC TTTGGCAGAA
                                                              PDGFR (3' end) ┐
1044 GAAGCCACGT TAGGCGGCCG CTCGAGATCA GCCTCGACTG TGCCTTCTAG TTGCCAGCCA
``` pLV-416- EXD2_K193A

Non-transduced HEK293T cells

FIGURE 22
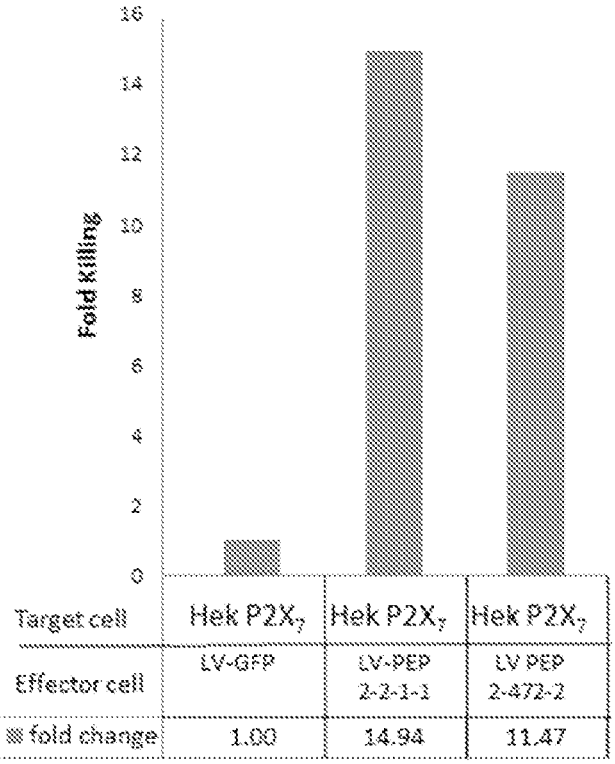
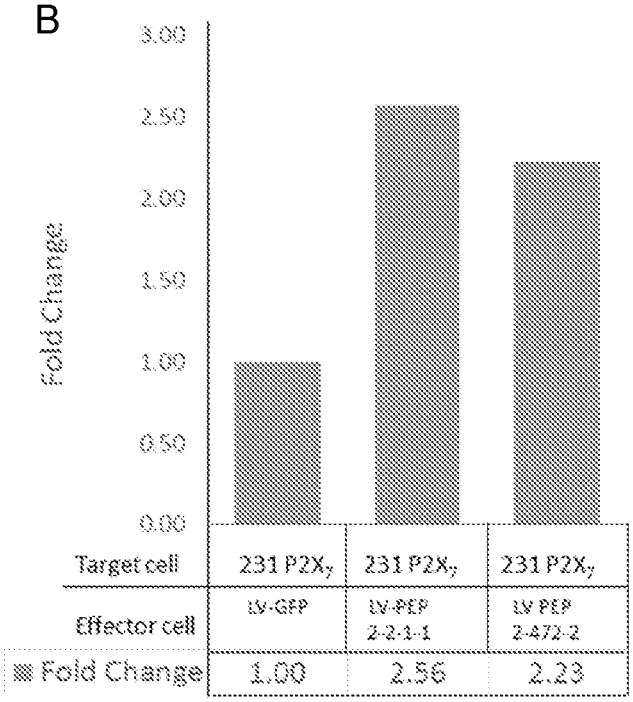

SEQUENCE LISTING

<160> NUMBER OF SEQ ID NOS: 66

<210> SEQ ID NO 1
<211> LENGTH: 3680
<212> TYPE: DNA
<213> ORGANISM: Homo sapiens

<400> SEQUENCE: 1
gtcattggag gagcttgaag ttaaagactc ctgctaaaaa ccagtacgtt tcattttgca    60

```
gttactggga gggggcttgc tgtggccctg tcaggaagag tagagctctg gtccagctcc    120
gcgcagggag ggaggctgtc accatgccgg cctgctgcag ctgcagtgat gttttccagt    180
atgagacgaa caaagtcact cggatccaga gcatgaatta tggcaccatt aagtggttct    240
tccacgtgat catctttttcc tacgtttgct ttgctctggt gagtgacaag ctgtaccagc    300
ggaaagagcc tgtcatcagt tctgtgcaca ccaaggtgaa ggggatagca gaggtgaaag    360
aggagatcgt ggagaatgga gtgaagaagt tggtgcacag tgtctttgac accgcagact    420
acaccttccc tttgcagggg aactctttct tcgtgatgac aaactttctc aaaacagaag    480
gccaagagca gcggttgtgt cccgagtatc ccacccgcag gacgctctgt tcctctgacc    540
gaggttgtaa aagggatgg atggacccgc agagcaaagg aattcagacc ggaaggtgtg    600
tagtgtatga agggaaccag aagacctgtg aagtctctgc ctggtgcccc atcgaggcag    660
tggaagaggc cccccggcct gctctcttga acagtgccga aaacttcact gtgctcatca    720
agaacaatat cgacttcccc ggccacaact acaccacgag aaacatcctg ccaggtttaa    780
acatcacttg taccttccac aagactcaga atccacagtg tcccattttc cgactaggag    840
acatcttccg agaaacaggc gataattttt cagatgtggc aattcagggc ggaataatgg    900
gcattgagat ctactgggac tgcaacctag accgttggtt ccatcactgc cgtcccaaat    960
acagtttccg tcgccttgac gacaagacca ccaacgtgtc cttgtaccct ggctacaact   1020
tcagatacgc caagtactac aaggaaaaca atgttgagaa acggactctg ataaaagtct   1080
tcgggatccg ttttgacatc ctggtttttg gcaccggagg aaaatttgac attatccagc   1140
tggttgtgta catcggctca accctctcct acttcggtct ggccgctgtg ttcatcgact   1200
tcctcatcga cacttactcc agtaactgct gtcgctccca tatttatccc tggtgcaagt   1260
gctgtcagcc ctgtgtggtc aacgaatact actacaggaa gaagtgcgag tccattgtgg   1320
agccaaagcc gacattaaag tatgtgtcct ttgtggatga atcccacatt aggatggtga   1380
accagcagct actagggaga agtctgcaag atgtcaaggg ccaagaagtc ccaagacctg   1440
cgatggactt cacagatttg tccaggctgc ccctggccct ccatgacaca ccccgattc   1500 ctggacaacc agaggagata cagctgctta gaaaggaggc gactcctaga tccagggata   1560
gccccgtctg gtgccagtgt ggaagctgcc tcccatctca actccctgag agccacaggt   1620
gcctggagga gctgtgctgc cggaaaaagc cgggggcctg catcaccacc tcagagctgt   1680
tcaggaagct ggtcctgtcc agacacgtcc tgcagttcct cctgctctac caggagccct   1740
tgctggcgct ggatgtggat tccaccaaca gccggctgcg gcactgtgcc tacaggtgct   1800
acgccacctg gcgcttcggc tcccaggaca tggctgactt tgccatcctg cccagctgct   1860
gccgctggag gatccggaaa gagtttccga gagtgaagg gcagtacagt ggcttcaaga   1920
gtccttactg aagccaggca ccgtggctca cgtctgtaat cccagcgctt tgggaggccg   1980
aggcaggcag atcacctgag gtcgggagtt ggagacccgc ctggctaaca aggcgaaatc   2040
ctgtctgtac taaaaataca aaaatcagcc agacatggtg gcatgcacct gcaatcccag   2100
ctactcggga ggctgaggca caagaatcac ttgaacccgg gaggcagagg ttgtagtgag   2160
cccagattgt gccactgctc tccagcctgg gaggcacagc aaactgtccc ccaaaaaaaa   2220
aaaagagtcc ttaccaatag caggggctgc agtagccatg ttaacatgac atttaccagc   2280
aacttgaact tcacctgcaa agctctgtgg ccacattttc agccaaaggg aaatatgctt   2340
tcatcttctg ttgctctctg tgtctgagag caaagtgacc tggttaaaca aaccagaatc   2400
cctctacatg gactcagaga aaagagattg agatgtaagt ctcaactctg tccccaggaa   2460
```

```
gttgtgtgac cctaggcctc tcacctctgt gcctctgtct ccttgttgcc caactactat      2520
ctcagagata ttgtgaggac aaattgagac agtgcacatg aactgtcttt taatgtgtaa      2580
agatctacat gaatgcaaaa catttcatta tgaggtcaga ctaggataat gtccaactaa      2640
aaacaaaccc ttttcatcct ggctggagaa tgtggagaac taaaggtggc cacaaattct      2700
ttgacactca gtcccccaa gacctaaggg ttttatctcc tccccttgaa tatgggtggc       2760
tctgattgct ttatccaaaa gtggaagtga cattgtgtca gtttcagatc ctgatcttaa      2820
gaggctgaca gcttctactt gctgtccctt ggaactcttg ctatcgggga agccagacgc      2880
catttaaaag tctgcctatc ctggccaggt gtggtggctc acacctgtaa tcccagcact      2940
ttgggagacc aaggcgggcg gatcacttaa agtcaggagt ccaagaccag actcgccaac      3000
atggtgaaac cgtatctcta ataaaaatac aaaaattagc tgggcatggt gcgggcacct      3060
gtagtcctag ctatcaagag gctgagacag gagaaacact tgaacctggg aggtggaggt      3120
tgcattgagc tgagatcgtg ccactgcact ccaggctggg tgacagagcg agactccatc      3180
tcaaaaaaaa aaaaagaaa aaaaaatgt ctgcctatcc tgagactgcc ctgctgtgag        3240
gaagcccaag cagtcacgtg gacagtgcct gaccagcccc agcttttcaag ccatccaagc     3300 ccagtcacca aacatgagag agaagaagcc ttcaggtgat tctggactcc actaacatat      3360
gactgatacc gcatgataca tcccaagtga aactgcccc ataaatccag aaaaccacat       3420
tgctatctta agtccctaag tttggggctt atttgttcca cagcaacagg taactggaac      3480
agagggcaag cctgatgaat gggcacacag actcagccca taccttccct ggttctaatg     3540
ttctcaggga gcccggacca acctgggag cctcaggaac ttaggtttcc actggacagt       3600
tctagaaggg ctatagacca aatcaggtaa ctcaccagac cagccttgga atctatcaaa      3660
tctaactgct gagctaccca                                                  3680
```

<210> SEQ ID NO 2
<211> LENGTH: 1788
<212> TYPE: DNA
<213> ORGANISM: Homo sapiens

<400> SEQUENCE: 2

```
atgccggcct gctgcagctg cagtgatgtt ttccagtatg agacgaacaa agtcactcgg      60
atccagagca tgaattatgg caccattaag tggttcttcc acgtgatcat cttttcctac     120
gtttgctttg ctctggtgag tgacaagctg taccagcgga agagcctgt catcagttct       180 gtgcacacca aggtgaaggg gatagcagag gtgaaagagg gatcgtgga aatggagtg       240 aagaagttgg tgcacagtgt ctttgacacc gcagactaca ccttcccttt gcagggaac      300 tctttcttcg tgatgacaaa cttttctcaaa acagaaggcc aagagcagcg gttgtgtccc    360
gagtatccca cccgcaggac gctctgttcc tctgaccgag gttgtaaaaa gggatggatg    420
gacccgcaga gcaaaggaat tcagaccgga aggtgtgtag tgtatgaagg gaaccagaag    480
acctgtgaag tctctgcctg gtgccccatc gaggcagtgg aagaggcccc ccggcctgct    540
ctcttgaaca gtgccgaaaa cttcactgtg ctcatcaaga acaatatcga cttccccggc    600
cacaactaca ccacgagaaa catcctgcca ggtttaaaca tcacttgtac cttccacaag    660
actcagaatc cacagtgtcc catttttccga ctaggagaca tcttccgaga aacaggcgat   720 aattttttcag atgtggcaat tcagggcgga ataatgggca ttgagatcta ctgggactgc   780
aacctagacc gttggttcca tcactgccgt cccaaataca gtttccgtcg ccttgacgac   840
```

```
aagaccacca acgtgtccct gtaccctggc tacaacttca gatacgccaa gtactacaag    900
gaaaacaatg ttgagaaacg gactctgata aaagtcttcg ggatccgttt tgacatcctg    960
gtttttggca ccggaggaaa atttgacatt atccagctgg ttgtgtacat cggctcaacc   1020
ctctcctact tcggtctggc cgctgtgttc atcgacttcc tcatcgacac ttactccagt   1080
aactgctgtc gctcccatat ttatccctgg tgcaagtgct gtcagccctg tgtggtcaac   1140
gaatactact acaggaagaa gtgcgagtcc attgtggagc caaagccgac attaaagtat   1200
gtgtcctttg tggatgaatc ccacattagg atggtgaacc agcagctact agggagaagt   1260
ctgcaagatg tcaagggcca agaagtccca agacctgcga tggacttcac agatttgtcc   1320
aggctgcccc tggccctcca tgacacaccc ccgattcctg acaaccaga ggagatacag    1380
ctgcttagaa aggaggcgac tcctagatcc agggatagcc ccgtctggtg ccagtgtgga   1440
agctgcctcc catctcaact ccctgagagc acaggtgcc tggaggagct gtgctgccgg    1500
aaaaagccgg gggcctgcat caccacctca gagctgttca ggaagctggt cctgtccaga   1560
cacgtcctgc agttcctcct gctctaccag gagcccttgc tggcgctgga tgtggattcc   1620
accaacagcc ggctgcggca ctgtgcctac aggtgctacg ccacctggcg cttcggctcc   1680
caggacatgg ctgactttgc catcctgccc agctgctgcc gctggaggat ccggaaagag   1740
tttccgaaga gtgaagggca gtacagtggc ttcaagagtc cttactga                 1788
```

<210> SEQ ID NO 3
<211> LENGTH: 595
<212> TYPE: PRT
<213> ORGANISM: Homo sapiens

<400> SEQUENCE: 3

```
Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
    130                 135                 140

Lys Gly Ile Gln Thr Gly Arg Cys Val Val Tyr Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205
```

```
Leu Pro Gly Leu Asn Ile Thr Cys Thr Phe His Lys Thr Gln Asn Pro
210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Ile Met Gly Ile Glu Ile
            245                 250                 255

Tyr Trp Asp Cys Asn Leu Asp Arg Trp Phe His His Cys Arg Pro Lys
                260                 265                 270

Tyr Ser Phe Arg Arg Leu Asp Asp Lys Thr Thr Asn Val Ser Leu Tyr
            275                 280                 285

Pro Gly Tyr Asn Phe Arg Tyr Ala Lys Tyr Tyr Lys Glu Asn Asn Val
290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                325                 330                 335

Ile Gly Ser Thr Leu Ser Tyr Phe Gly Leu Ala Ala Val Phe Ile Asp
            340                 345                 350

Phe Leu Ile Asp Thr Tyr Ser Ser Asn Cys Cys Arg Ser His Ile Tyr
                355                 360                 365

Pro Trp Cys Lys Cys Gln Pro Cys Val Val Asn Glu Tyr Tyr Tyr
370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
            405                 410                 415

Leu Gly Arg Ser Leu Gln Asp Val Lys Gly Gln Glu Val Pro Arg Pro
            420                 425                 430

Ala Met Asp Phe Thr Asp Leu Ser Arg Leu Pro Leu Ala Leu His Asp
            435                 440                 445

Thr Pro Pro Ile Pro Gly Gln Pro Glu Glu Ile Gln Leu Leu Arg Lys
450                 455                 460

Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
            485                 490                 495

Leu Cys Cys Arg Lys Lys Pro Gly Ala Cys Ile Thr Thr Ser Glu Leu
            500                 505                 510

Phe Arg Lys Leu Val Leu Ser Arg His Val Leu Gln Phe Leu Leu Leu
            515                 520                 525

Tyr Gln Glu Pro Leu Leu Ala Leu Asp Val Asp Ser Thr Asn Ser Arg
530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Arg Trp Arg
            565                 570                 575

Ile Arg Lys Glu Phe Pro Lys Ser Glu Gly Gln Tyr Ser Gly Phe Lys
            580                 585                 590

Ser Pro Tyr
        595

<210> SEQ ID NO 4
<211> LENGTH: 164
<212> TYPE: PRT
```

-continued

<213> ORGANISM: Homo sapiens

<400> SEQUENCE: 4

```
Met Lys Trp Lys Ala Leu Phe Thr Ala Ala Ile Leu Gln Ala Gln Leu
1               5                   10                  15
Pro Ile Thr Glu Ala Gln Ser Phe Gly Leu Leu Asp Pro Lys Leu Cys
            20                  25                  30
Tyr Leu Leu Asp Gly Ile Leu Phe Ile Tyr Gly Val Ile Leu Thr Ala
        35                  40                  45
Leu Phe Leu Arg Val Lys Phe Ser Arg Ser Ala Asp Ala Pro Ala Tyr
    50                  55                  60
Gln Gln Gly Gln Asn Gln Leu Tyr Asn Glu Leu Asn Leu Gly Arg Arg
65                  70                  75                  80
Glu Glu Tyr Asp Val Leu Asp Lys Arg Arg Gly Arg Asp Pro Glu Met
                85                  90                  95
Gly Gly Lys Pro Gln Arg Arg Lys Asn Pro Gln Glu Gly Leu Tyr Asn
            100                 105                 110
Glu Leu Gln Lys Asp Lys Met Ala Glu Ala Tyr Ser Glu Ile Gly Met
        115                 120                 125
Lys Gly Glu Arg Arg Arg Gly Lys Gly His Asp Gly Leu Tyr Gln Gly
    130                 135                 140
Leu Ser Thr Ala Thr Lys Asp Thr Tyr Asp Ala Leu His Met Gln Ala
145                 150                 155                 160
Leu Pro Pro Arg
```

<210> SEQ ID NO 5
<211> LENGTH: 207
<212> TYPE: PRT
<213> ORGANISM: Homo sapiens

<400> SEQUENCE: 5

```
Met Gln Ser Gly Thr His Trp Arg Val Leu Gly Leu Cys Leu Leu Ser
1               5                   10                  15
Val Gly Val Trp Gly Gln Asp Gly Asn Glu Glu Met Gly Gly Ile Thr
            20                  25                  30
Gln Thr Pro Tyr Lys Val Ser Ile Ser Gly Thr Thr Val Ile Leu Thr
        35                  40                  45
Cys Pro Gln Tyr Pro Gly Ser Glu Ile Leu Trp Gln His Asn Asp Lys
    50                  55                  60
Asn Ile Gly Gly Asp Glu Asp Lys Asn Ile Gly Ser Asp Glu Asp
65                  70                  75                  80
His Leu Ser Leu Lys Glu Phe Ser Glu Leu Glu Gln Ser Gly Tyr Tyr
                85                  90                  95
Val Cys Tyr Pro Arg Gly Ser Lys Pro Glu Asp Ala Asn Phe Tyr Leu
            100                 105                 110
Tyr Leu Arg Ala Arg Val Cys Glu Asn Cys Met Glu Met Asp Val Met
        115                 120                 125
Ser Val Ala Thr Ile Val Ile Val Asp Ile Cys Ile Thr Gly Gly Leu
    130                 135                 140
Leu Leu Leu Val Tyr Tyr Trp Ser Lys Asn Arg Lys Ala Lys Ala Lys
145                 150                 155                 160
Pro Val Thr Arg Gly Ala Gly Ala Gly Gly Arg Gln Arg Gly Gln Asn
                165                 170                 175
Lys Glu Arg Pro Pro Pro Val Pro Asn Pro Asp Tyr Glu Pro Ile Arg
            180                 185                 190
```

```
Lys Gly Gln Arg Asp Leu Tyr Ser Gly Leu Asn Gln Arg Ile
        195                 200                 205
```

<210> SEQ ID NO 6
<211> LENGTH: 180
<212> TYPE: PRT
<213> ORGANISM: Homo sapiens

<400> SEQUENCE: 6

```
Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg
            180
```

<210> SEQ ID NO 7
<211> LENGTH: 171
<212> TYPE: PRT
<213> ORGANISM: Homo sapiens

<400> SEQUENCE: 7

```
Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125
```

Glu Thr Gly Arg Leu Ser Gly Ala Ala Asp Thr Gln Ala Leu Leu Arg
            130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 8
<211> LENGTH: 244
<212> TYPE: PRT
<213> ORGANISM: Homo sapiens

<400> SEQUENCE: 8

Met Asp Thr Glu Ser Asn Arg Arg Ala Asn Leu Ala Leu Pro Gln Glu
1               5                   10                  15

Pro Ser Ser Val Pro Ala Phe Glu Val Leu Glu Ile Ser Pro Gln Glu
            20                  25                  30

Val Ser Ser Gly Arg Leu Leu Lys Ser Ala Ser Ser Pro Pro Leu His
        35                  40                  45

Thr Trp Leu Thr Val Leu Lys Lys Glu Gln Glu Phe Leu Gly Val Thr
50                  55                  60

Gln Ile Leu Thr Ala Met Ile Cys Leu Cys Phe Gly Thr Val Val Cys
65                  70                  75                  80

Ser Val Leu Asp Ile Ser His Ile Glu Gly Asp Ile Phe Ser Ser Phe
                85                  90                  95

Lys Ala Gly Tyr Pro Phe Trp Gly Ala Ile Phe Phe Ser Ile Ser Gly
            100                 105                 110

Met Leu Ser Ile Ile Ser Glu Arg Arg Asn Ala Thr Tyr Leu Val Arg
        115                 120                 125

Gly Ser Leu Gly Ala Asn Thr Ala Ser Ser Ile Ala Gly Gly Thr Gly
130                 135                 140

Ile Thr Ile Leu Ile Ile Asn Leu Lys Lys Ser Leu Ala Tyr Ile His
145                 150                 155                 160

Ile His Ser Cys Gln Lys Phe Phe Glu Thr Lys Cys Phe Met Ala Ser
                165                 170                 175

Phe Ser Thr Glu Ile Val Val Met Met Leu Phe Leu Thr Ile Leu Gly
            180                 185                 190

Leu Gly Ser Ala Val Ser Leu Thr Ile Cys Gly Ala Gly Glu Glu Leu
        195                 200                 205

Lys Gly Asn Lys Val Pro Glu Asp Arg Val Tyr Glu Glu Leu Asn Ile
210                 215                 220

Tyr Ser Ala Thr Tyr Ser Glu Leu Glu Asp Pro Gly Glu Met Ser Pro
225                 230                 235                 240

Pro Ile Asp Leu

<210> SEQ ID NO 9
<211> LENGTH: 374
<212> TYPE: PRT
<213> ORGANISM: Homo sapiens

<400> SEQUENCE: 9

Met Trp Phe Leu Thr Thr Leu Leu Leu Trp Val Pro Val Asp Gly Gln
1               5                   10                  15

Val Asp Thr Lys Ala Val Ile Thr Leu Gln Pro Pro Trp Val Ser
            20                  25                  30

Val Phe Gln Glu Glu Thr Val Thr Leu His Cys Glu Val Leu His Leu
 35                  40                  45

Pro Gly Ser Ser Ser Thr Gln Trp Phe Leu Asn Gly Thr Ala Thr Gln
 50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                 85                  90                  95

Gln Leu Glu Ile His Arg Gly Trp Leu Leu Leu Gln Val Ser Ser Arg
            100                 105                 110

Val Phe Thr Glu Gly Glu Pro Leu Ala Leu Arg Cys His Ala Trp Lys
        115                 120                 125

Asp Lys Leu Val Tyr Asn Val Leu Tyr Tyr Arg Asn Gly Lys Ala Phe
130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Val Leu Phe Tyr Leu Ala Val Gly Ile Met Phe Leu
290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Glu Leu Lys
            340                 345                 350

Cys Gln Glu Gln Lys Glu Glu Gln Leu Gln Glu Gly Val His Arg Lys
        355                 360                 365

Glu Pro Gln Gly Ala Thr
        370

<210> SEQ ID NO 10
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PEP2-2-3

<400> SEQUENCE: 10

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn His
            20                  25                  30

Asp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Lys Pro Met Asp Thr Glu Phe Asp Tyr Trp Ser Pro Gly
            100                 105                 110

Thr Leu Val Thr Val Ser Ser
            115
```

```
<210> SEQ ID NO 11
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PEP2-2-3 coding sequence

<400> SEQUENCE: 11
gaagttcaac tgctggagag tggagggggc ctcgtgcagc cgggcggcag cttgcgcctg      60
tcatgtgcag caagcgggtt cacctttagg aaccacgata tggggtgggt gaggcaggct     120
ccgggaaagg gtctggaatg ggtgagtgcc atatcaggga gcggaggctc cacctactac     180
gcagactccg tgaagggtcg gtttacgatt tccagagaca attccaagaa taccctgtac     240
ctgcagatga actccctccg cgccgaagat acagcagtct actactgtgc agaaccaaaa     300
ccaatggata cagaattcga ctattggagt cctggaactc ttgtcactgt atccagt       357

<210> SEQ ID NO 12
<211> LENGTH: 21
<212> TYPE: PRT
<213> ORGANISM: Homo sapiens

<400> SEQUENCE: 12

Met Ala Leu Pro Val Thr Ala Leu Leu Leu Pro Leu Ala Leu Leu Leu
1               5                   10                  15

His Ala Ala Arg Pro
            20

<210> SEQ ID NO 13
<211> LENGTH: 72
<212> TYPE: DNA
<213> ORGANISM: Homo sapiens

<400> SEQUENCE: 13
gagcgcgtca tggctcttcc tgtgaccgca ttgctgctgc cgctggcctt gctgctgcat      60
gcagctcggc ca                                                          72

<210> SEQ ID NO 14
<211> LENGTH: 228
<212> TYPE: PRT
```

<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Long hinge

<400> SEQUENCE: 14

Glu Ser Lys Tyr Gly Pro Pro Cys Pro Ser Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys
225

<210> SEQ ID NO 15
<211> LENGTH: 684
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Long hinge

<400> SEQUENCE: 15
gagagtaaat atggacctcc gtgtccgagt tgtcccgcgc ctcctgtggc cggcccctct      60
gtatttctgt ttccacctaa gccgaaagat acattgatga ttagccgaac accagaggtt     120
acttgtgtgg ttgttgacgt gagtcaagag gaccctgagg tgcagtttaa ttggtatgtc     180
gacggagttg aggtgcataa cgccaagacg aagccgcgag aggagcagtt taattccacc     240
tacagggtcg tatccgttct cactgtcctt caccaggact ggctgaatgg aaggagtac      300 aaatgcaaag tgagcaataa aggcctgccg agctccatcg aaaaaaccat ttccaaggca     360

```
aaaggccaac cccgagagcc acaggtctat accctgccac caagccagga ggaaatgacc        420
aagaatcagg tgagcctcac ctgtctggtc aagggcttct acccgtccga catcgcggtg        480
gagtgggaga gtaacggaca gcctgaaaac aattacaaga caaccccgcc tgttttggac        540
tctgacggct ccttttttct gtactctcgg cttaccgtgg ataagagtag atggcaagaa        600
ggcaacgtct tcagctgttc cgtgatgcat gaggcgctgc ataaccatta tacacaaaaa        660
agtctgtcct tgagcctggg caaa                                               684
```

```
<210> SEQ ID NO 16
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Short hinge

<400> SEQUENCE: 16

Gly Gly Gly Gly Ser Gly Gly Gly Gly Ser Gly Gly Gly Gly Ser Glu
1               5                   10                  15

Ser Lys Tyr Gly Pro Pro Cys Pro Pro Cys Pro Asp Pro Lys
            20                  25                  30
```

```
<210> SEQ ID NO 17
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Short hinge

<400> SEQUENCE: 17
ggcggcggcg gctctggcgg tggggggtagc ggaggcggcg aagcgaatc caaatatggc         60 cctccttgtc caccgtgccc cgatccaaag                                         90
```

```
<210> SEQ ID NO 18
<211> LENGTH: 68
<212> TYPE: PRT
<213> ORGANISM: Homo sapiens

<400> SEQUENCE: 18

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser
65
```

```
<210> SEQ ID NO 19
<211> LENGTH: 204
<212> TYPE: DNA
<213> ORGANISM: Artificial Sequence
<220> FEATURE:
<223> OTHER INFORMATION: Description of Artificial Sequence: Synthetic
      polynucleotide
```

<220> FEATURE:
<223> OTHER INFORMATION: CD28 coding sequence

<400> SEQUENCE: 19

```
ttttgggtgc tggtggtggt ggggggtgtc ctcgcttgct acagtttgtt ggtgacagtt    60
gcctttatta ttttttgggt gcgcagtaag cggagtcgcc tccttcattc cgactatatg   120
aacatgacac tcgccgccc aggcccaacg aggaaacatt atcagccata tgcaccacct    180
agagactttg ccgcttaccg gtcc                                          204
```

<210> SEQ ID NO 20
<211> LENGTH: 36
<212> TYPE: PRT
<213> ORGANISM: Homo sapiens

<400> SEQUENCE: 20

Arg Asp Gln Arg Leu Pro Pro Asp Ala His Lys Pro Pro Gly Gly Gly
1               5                   10                  15

Ser Phe Arg Thr Pro Ile Gln Glu Glu Gln Ala Asp Ala His Ser Thr
            20                  25                  30

Leu Ala Lys Ile
        35

<210> SEQ ID NO 21
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: OX40 coding sequence

<400> SEQUENCE: 21

```
cgagatcaaa ggcttccccc cgatgcacac aaaccacccg gcggtggctc atttcgaaca    60
ccaattcagg aagagcaggc agacgcccac agcaccctgg ccaagatc               108
```

<210> SEQ ID NO 22
<211> LENGTH: 112
<212> TYPE: PRT
<213> ORGANISM: Homo sapiens

<400> SEQUENCE: 22

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 23
<211> LENGTH: 336

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Coding sequence for CD3zeta

<400> SEQUENCE: 23
cgggtaaagt tcagccgaag tgcagatgcg ccggcatacc agcagggcca gaatcaattg    60
tacaatgagc ttaacctcgg ccgcagagag gagtatgatg tactggataa gcggcgcgga   120
cgggatcctg agatgggagg aaagcctcgg agaaaaaatc cccaggaagg actttacaat   180
gagttgcaga aggataagat ggccgaagca tattctgaaa tcgggatgaa aggtgagcgg   240
cggagaggaa aaggccacga cgggctctac caggggctga gcacagctac taaagataca   300
tacgacgcac ttcatatgca agccctgcct ccccgc                             336

<210> SEQ ID NO 24
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: P2A

<400> SEQUENCE: 24

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 25
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Coding sequence for P2A

<400> SEQUENCE: 25
ggaagcggtg ccacgaactt ttctctcctc aaacaggctg gggacgtcga ggaaaatcca    60
ggtccc                                                               66

<210> SEQ ID NO 26
<211> LENGTH: 611
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CAR-Long hinge

<400> SEQUENCE: 26

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45
```

Thr Phe Arg Asn His Asp Met Gly Trp Val Arg Gln Ala Pro Gly Lys
    50                  55                  60

Gly Leu Glu Trp Val Ser Ala Ile Ser Gly Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Glu Pro Lys Pro Met Asp Thr Glu Phe Asp
        115                 120                 125

Tyr Trp Ser Pro Gly Thr Leu Val Thr Val Ser Ser Gly Gly Gly Glu
    130                 135                 140

Ser Lys Tyr Gly Pro Pro Cys Pro Ser Cys Pro Ala Pro Pro Val Ala
145                 150                 155                 160

Gly Pro Ser Val Phe Leu Phe Pro Pro Lys Pro Lys Asp Thr Leu Met
                165                 170                 175

Ile Ser Arg Thr Pro Glu Val Thr Cys Val Val Val Asp Val Ser Gln
            180                 185                 190

Glu Asp Pro Glu Val Gln Phe Asn Trp Tyr Val Asp Gly Val Glu Val
        195                 200                 205

His Asn Ala Lys Thr Lys Pro Arg Glu Glu Gln Phe Asn Ser Thr Tyr
    210                 215                 220

Arg Val Val Ser Val Leu Thr Val Leu His Gln Asp Trp Leu Asn Gly
225                 230                 235                 240

Lys Glu Tyr Lys Cys Lys Val Ser Asn Lys Gly Leu Pro Ser Ser Ile
                245                 250                 255

Glu Lys Thr Ile Ser Lys Ala Lys Gly Gln Pro Arg Glu Pro Gln Val
            260                 265                 270

Tyr Thr Leu Pro Pro Ser Gln Glu Glu Met Thr Lys Asn Gln Val Ser
        275                 280                 285

Leu Thr Cys Leu Val Lys Gly Phe Tyr Pro Ser Asp Ile Ala Val Glu
    290                 295                 300

Trp Glu Ser Asn Gly Gln Pro Glu Asn Asn Tyr Lys Thr Thr Pro Pro
305                 310                 315                 320

Val Leu Asp Ser Asp Gly Ser Phe Phe Leu Tyr Ser Arg Leu Thr Val
                325                 330                 335

Asp Lys Ser Arg Trp Gln Glu Gly Asn Val Phe Ser Cys Ser Val Met
            340                 345                 350

His Glu Ala Leu His Asn His Tyr Thr Gln Lys Ser Leu Ser Leu Ser
        355                 360                 365

Leu Gly Lys Phe Trp Val Leu Val Val Val Gly Gly Val Leu Ala Cys
    370                 375                 380

Tyr Ser Leu Leu Val Thr Val Ala Phe Ile Ile Phe Trp Val Arg Ser
385                 390                 395                 400

Lys Arg Ser Arg Leu Leu His Ser Asp Tyr Met Asn Met Thr Pro Arg
                405                 410                 415

Arg Pro Gly Pro Thr Arg Lys His Tyr Gln Pro Tyr Ala Pro Pro Arg
            420                 425                 430

Asp Phe Ala Ala Tyr Arg Ser Arg Asp Gln Arg Leu Pro Pro Asp Ala
        435                 440                 445

His Lys Pro Pro Gly Gly Gly Ser Phe Arg Thr Pro Ile Gln Glu Glu
    450                 455                 460

```
Gln Ala Asp Ala His Ser Thr Leu Ala Lys Ile Arg Val Lys Phe Ser
465                 470                 475                 480

Arg Ser Ala Asp Ala Pro Ala Tyr Gln Gln Gly Gln Asn Gln Leu Tyr
            485                 490                 495

Asn Glu Leu Asn Leu Gly Arg Arg Glu Glu Tyr Asp Val Leu Asp Lys
        500                 505                 510

Arg Arg Gly Arg Asp Pro Glu Met Gly Gly Lys Pro Arg Arg Lys Asn
    515                 520                 525

Pro Gln Glu Gly Leu Tyr Asn Glu Leu Gln Lys Asp Lys Met Ala Glu
530                 535                 540

Ala Tyr Ser Glu Ile Gly Met Lys Gly Glu Arg Arg Arg Gly Lys Gly
545                 550                 555                 560

His Asp Gly Leu Tyr Gln Gly Leu Ser Thr Ala Thr Lys Asp Thr Tyr
                565                 570                 575

Asp Ala Leu His Met Gln Ala Leu Pro Pro Arg Gly Ser Gly Ala Thr
            580                 585                 590

Asn Phe Ser Leu Leu Lys Gln Ala Gly Asp Val Glu Glu Asn Pro Gly
        595                 600                 605

Pro Gly Glu
    610

<210> SEQ ID NO 27
<211> LENGTH: 408
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CAR-Short hinge

<400> SEQUENCE: 27

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Arg Asn His Asp Met Gly Trp Val Arg Gln Ala Pro Gly Lys
    50                  55                  60

Gly Leu Glu Trp Val Ser Ala Ile Ser Gly Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Glu Pro Lys Pro Met Asp Thr Glu Phe Asp
        115                 120                 125

Tyr Trp Ser Pro Gly Thr Leu Val Thr Val Ser Ser Gly Gly Gly Gly
    130                 135                 140

Ser Gly Gly Gly Ser Gly Gly Gly Ser Glu Ser Lys Tyr Gly
145                 150                 155                 160

Pro Pro Cys Pro Pro Cys Pro Asp Pro Lys Phe Trp Val Leu Val Val
                165                 170                 175

Val Gly Gly Val Leu Ala Cys Tyr Ser Leu Leu Val Thr Val Ala Phe
            180                 185                 190
```

Ile Ile Phe Trp Val Arg Ser Lys Arg Ser Arg Leu Leu His Ser Asp
            195                 200                 205

Tyr Met Asn Met Thr Pro Arg Arg Pro Gly Pro Thr Arg Lys His Tyr
            210                 215                 220

Gln Pro Tyr Ala Pro Pro Arg Asp Phe Ala Ala Tyr Arg Ser Arg Asp
225                 230                 235                 240

Gln Arg Leu Pro Pro Asp Ala His Lys Pro Pro Gly Gly Gly Ser Phe
                245                 250                 255

Arg Thr Pro Ile Gln Glu Glu Gln Ala Asp Ala His Ser Thr Leu Ala
            260                 265                 270

Lys Ile Arg Val Lys Phe Ser Arg Ser Ala Asp Ala Pro Ala Tyr Gln
            275                 280                 285

Gln Gly Gln Asn Gln Leu Tyr Asn Glu Leu Asn Leu Gly Arg Arg Glu
290                 295                 300

Glu Tyr Asp Val Leu Asp Lys Arg Arg Gly Arg Asp Pro Glu Met Gly
305                 310                 315                 320

Gly Lys Pro Arg Arg Lys Asn Pro Gln Glu Gly Leu Tyr Asn Glu Leu
            325                 330                 335

Gln Lys Asp Lys Met Ala Glu Ala Tyr Ser Glu Ile Gly Met Lys Gly
            340                 345                 350

Glu Arg Arg Arg Gly Lys Gly His Asp Gly Leu Tyr Gln Gly Leu Ser
            355                 360                 365

Thr Ala Thr Lys Asp Thr Tyr Asp Ala Leu His Met Gln Ala Leu Pro
370                 375                 380

Pro Arg Gly Ser Gly Ala Thr Asn Phe Ser Leu Leu Lys Gln Ala Gly
385                 390                 395                 400

Asp Val Glu Glu Asn Pro Gly Pro
            405

<210> SEQ ID NO 28
<211> LENGTH: 1875
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Coding CAR-long hinge

<400> SEQUENCE: 28
gaccggcgcc tactctagag gagcgcgtca tggctcttcc tgtgaccgca ttgctgctgc      60
cgctggcctt gctgctgcat gcagctcggc cagaagttca actgctggag agtggagggg     120
gcctcgtgca gccgggcggc agcttgcgcc tgtcatgtgc agcaagcggg ttcaccttta     180
ggaaccacga tatggggtgg gtgaggcagg ctccggaaaa gggtctggaa tgggtgagtg     240
ccatatcagg gagcggaggc tccacctact acgcagactc cgtgaagggt cggtttacga     300
tttccagaga caattccaag aatacctgt acctgcagat gaactcctc cgcgccgaag     360 atacagcagt ctactactgt gcagaaccaa accaatgga tacagaattc gactattgga     420
gtcctggaac tcttgtcact gtatccagtg gaggaggcga gagtaaatat ggacctccgt     480 gtcccgagttg tcccgcgcct cctgtggccg gcccctctgt atttctgttt ccacctaagc     540
cgaaagatac attgatgatt agccgaacac cagaggttac ttgtgtggtt gttgacgtga     600
gtcaagagga ccctgaggtg cagtttaatt ggtatgtcga cggagttgag gtgcataacg     660
ccaagacgaa gccgcgagag gagcagttta attccaccta cagggtcgta tccgttctca     720

| | |
|---|---|
| ctgtccttca ccaggactgg ctgaatggga aggagtacaa atgcaaagtg agcaataaag | 780 |
| gcctgccgag ctccatcgaa aaaccattt ccaaggcaaa aggccaaccc cgagagccac | 840 |
| aggtctatac cctgccacca agccaggagg aaatgaccaa gaatcaggtg agcctcacct | 900 |
| gtctggtcaa gggcttctac ccgtccgaca tcgcggtgga gtgggagagt aacggacagc | 960 |
| ctgaaaacaa ttacaagaca accccgcctg ttttggactc tgacggctcc ttttttctgt | 1020 |
| actctcggct taccgtggat aagagtagat ggcaagaagg caacgtcttc agctgttccg | 1080 |
| tgatgcatga ggcgctgcat aaccattata cacaaaaaag tctgtccttg agcctgggca | 1140 |
| aatttttgggt gctggtggtg gtgggggtg cctcgcttg ctacagtttg ttggtgacag | 1200 |
| ttgcctttat tattttttgg gtgcgcagta agcggagtcg cctccttcat tccgactata | 1260 |
| tgaacatgac acctcgccgc ccaggcccaa cgaggaaaca ttatcagcca tatgcaccac | 1320 |
| ctagagactt tgccgcttac cggtcccgag atcaaaggct tccccccgat gcacacaaac | 1380 |
| cacccggcgg tggctcattt cgaacaccaa ttcaggaaga gcaggcagac gcccacagca | 1440 |
| ccctggccaa gatccgggta agttcagcc gaagtgcaga tgcgccggca taccagcagg | 1500 |
| gccagaatca attgtacaat gagcttaacc tcggccgcag agaggagtat gatgtactgg | 1560 |
| ataagcggcg cggacgggat cctgagatgg gaggaaagcc tcggagaaaa aatccccagg | 1620 |
| aaggacttta caatgagttg cagaaggata agatggccga agcatattct gaaatcggga | 1680 |
| tgaaaggtga gcggcggaga ggaaaaggcc acgacgggct ctaccagggg ctgagcacag | 1740 |
| ctactaaaga tacatacgac gcacttcata tgcaagccct gcctcccgc ggaagcggtg | 1800 |
| ccacgaactt ttctctcctc aaacaggctg gggacgtcga ggaaaatcca ggtcccggcg | 1860 |
| aattcgccac catgc | 1875 |

<210> SEQ ID NO 29
<211> LENGTH: 1272
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Coding CAR-short hinge

<400> SEQUENCE: 29

| | |
|---|---|
| gaccggcgcc tactctagag gagcgcgtca tggccctgcc tgtgacagcc ctgctgctgc | 60 |
| cactcgctct tctccttcac gccgcaagac ccgaagtgca gcttctggag tctggaggtg | 120 |
| gtttggtgca gcctggcggg tctctcagat tgtcatgcgc cgcatccggt ttcaccttc | 180 |
| ggaaccatga tatgggttgg gtccgccagg ccccaggcaa gggtcttgag tgggtctccg | 240 |
| ccatcagcgg cagtggcggg tccacatact acgcagactc cgtcaaaggc agatttacaa | 300 |
| tttcacggga taatagtaag aacactctgt acctccagat gaatagtctc cgggcggagg | 360 |
| acacagctgt gtactattgc gcggagccaa agccaatgga tactgagttt gattattgga | 420 |
| gcccgggaac cctggtgaca gtatccagcg gcggcggcgg ctctggcggt gggggtagcg | 480 |
| gaggcggcgg aagcgaatcc aaatatggcc ctccttgtcc accgtgcccc gatccaaagt | 540 |
| tctgggtgct ggtggtagtg ggtggcgtcc tggcctgtta ttctctgctt gtgacagtcg | 600 |
| cgtttatcat cttttgggtc cggtctaaac gctctaggtt gttgcactcc gattacatga | 660 |
| acatgacccc acgccggcct ggccctacgg gaagcactca ccaaccttac gctcctccca | 720 |
| gggatttcgc cgcttacagg agccgagatc agagactgcc acccgatgca cacaaaccac | 780 |

```
ccggtggtgg gtctttcagg accccaatcc aggaggagca agctgacgcg cattccaccc      840
ttgccaagat aagggtcaaa tttagtaggt cagctgacgc gccggcctat caacagggac      900
agaaccagtt gtataatgaa ctcaatctcg gacgacgcga ggagtacgac gtactggata      960
agaggcgcgg cagggatcct gaaatgggcg gcaagcccg gcgaaaaaac ccccaggagg      1020
gactctacaa tgagctgcag aaggacaaaa tggcagaagc ttactccgaa attggaatga     1080
agggcgaaag aaggagaggg aaagggcacg atggcctgta tcagggcctg agtaccgcca     1140
ccaaggacac gtatgatgcc ctgcatatgc aggcactgcc ccctagagga agcggggcta     1200
cgaatttcag cctcctgaaa caggctggcg acgtggagga aaatccgggg ccaggcgaat     1260
tcgccaccat gc                                                          1272
```

<210> SEQ ID NO 30
<211> LENGTH: 21
<212> TYPE: PRT
<213> ORGANISM: Homo sapiens

<400> SEQUENCE: 30

Met Ala Leu Pro Val Thr Ala Leu Leu Leu Pro Leu Ala Leu Leu Leu
1               5                   10                  15

His Ala Ala Arg Pro
            20

<210> SEQ ID NO 31
<211> LENGTH: 63
<212> TYPE: DNA
<213> ORGANISM: Homo sapiens

<400> SEQUENCE: 31
atggctcttc ctgtgaccgc attgctgctg ccgctggcct tgctgctgca tgcagctcgg      60
cca                                                                   63

<210> SEQ ID NO 32
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PEP2-2-1-1 binding peptide

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn His
            20                  25                  30

Asp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Lys Pro Met Asp Thr Glu Phe Asp Tyr Arg Ser Pro Gly
            100                 105                 110

Thr Leu Val Thr Val Ser Ser

<210> SEQ ID NO 33
<211> LENGTH: 119
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: PEP2-472-2 binding peptide

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Tyr Thr Phe Pro Met Lys
            20                  25                  30

Asp Met Gly Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Lys Pro Met Asp Thr Glu Phe Asp Tyr Arg Ser Pro Gly
            100                 105                 110

Thr Leu Val Thr Val Leu Glu
        115

<210> SEQ ID NO 34
<211> LENGTH: 119
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: PEP2-2-12 binding peptide

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn His
            20                  25                  30

Asp Met Gly Trp Val Arg Gln Ala Pro Gly Lys Gly Leu Glu Trp Val
        35                  40                  45

Ser Ala Ile Ser Gly Ser Gly Ser Thr Tyr Tyr Ala Asn Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Pro Lys Pro Met Asp Thr Glu Phe Asp Tyr Pro Ser Pro Gly
            100                 105                 110

Thr Leu Val Thr Val Ser Ser
        115

<210> SEQ ID NO 35
<211> LENGTH: 1864

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PEP2-2-1-1 Chimeric Antigen Receptor

<400> SEQUENCE: 35
cctccataga agattctaga gctagcgaat tctgcagtcg acggtaccgc gggcccggga    60
tccaccggtg ccgccgccat ggctcttcct gtgaccgcat tgctgctgcc gctggccttg   120
ctgctgcatg cagctcggcc agaagttcaa ctgctggaga gtggaggggg cctcgtgcag   180
ccgggcggca gcttgcgcct gtcatgtgca gcaagcgggt tcacctttag gaaccacgat   240
atggggtggg tgaggcaggc tccgggaaag gtctggaat gggtgagtgc catatcaggg    300
agcggaggct ccacctacta cgcagactcc gtgaagggtc ggtttacgat ttccagagac   360
aattccaaga ataccctgta cctgcagatg aactccctcc gcgccgaaga tacagcagtc   420
tactactgtg cagaaccaaa accaatggat acagaattcg actataggag tcctggaact   480
cttgtcactg tatccagtgg aggaggcgag agtaaatatg gacctccgtg tccgagttgt   540
cccgcgcctc ctgtggccgg ccctctgta tttctgtttc cacctaagcc gaaagataca    600
ttgatgatta gccgaacacc agaggttact tgtgtggttg ttgacgtgag tcaagaggac   660
cctgaggtgc agtttaattg gtatgtcgac ggagttgagg tgcataacgc caagacgaag   720
ccgcgagagg agcagtttaa ttccaccta cagggtcgtat ccgttctcac tgtccttcac   780
caggactggc tgaatgggaa ggagtacaaa tgcaaagtga gcaataaagg cctgccgagc   840
tccatcgaaa aaaccatttc caaggcaaaa ggccaacccc gagagccaca ggtctatacc   900
ctgccaccaa gccaggagga atgaccaag aatcaggtga gcctcacctg tctggtcaag    960
ggcttctacc cgtccgacat cgcggtggag tgggagagta cggacagcc tgaaaacaat   1020
tacaagacaa ccccgcctgt tttggactct gacggctcct ttttctgta ctctcggctt   1080
accgtggata gagtagatg gcaagaaggc aacgtcttca gctgttccgt gatgcatgag   1140
gcgctgcata accattatac acaaaaaagt ctgtccttga gctgggcaa accttttgg    1200
gtgctggtgg tggtggggg tgtcctcgct tgctacagtt tgttggtgac agttgccttt   1260
attattttt gggtgcgcag taagcggagt cgcctccttc attccgacta tatgaacatg   1320
acacctcgcc gcccaggccc aacgaggaaa cattatcagc catatgcacc acctagagac   1380
tttgccgctt accggtcccg agatcaaagg cttccccccg atgcacacaa accacccggc   1440
ggtggctcat ttcgaacacc aattcaggaa gagcaggcag acgcccacag caccctggcc   1500
aagatccggg taaagttcag ccgaagtgca gatgcgccgg cataccagca gggccagaat   1560
caattgtaca atgagcttaa cctcggccgc agagaggagt atgatgtact ggataagcgg   1620
cgcggacggg atcctgagat gggaggaaag cctcggagaa aaatccccca ggaaggactt   1680
tacaatgagt tgcagaagga taagatggcc gaagcatatt ctgaaatcgg gatgaaaggt   1740
gagcggcgga gaggaaaagg ccacgacggg ctctaccagg ggctgagcac agctactaaa   1800
gatacatacg acgcacttca tatgcaagcc ctgcctcccc gcgcggccgc agcatcgata   1860
agta                                                                1864
```

<210> SEQ ID NO 36
<211> LENGTH: 1863
<212> TYPE: DNA
<213> ORGANISM: Artificial Sequence

```
<220> FEATURE:
<223> OTHER INFORMATION: Description of Artificial Sequence: Synthetic
      polynucleotide
<220> FEATURE:
<223> OTHER INFORMATION: PEP2-472-2 Chimeric Antigen Receptor

<400> SEQUENCE: 36
cctccataga agattctaga gctagcgaat tctgcagtcg acggtaccgc gggcccggga      60
tccaccggtc cgccgccatg gcattgccag ttacggcgct cctcctgcca ctcgcactcc     120
tcttgcacgc agctcgaccc gaggtccagc ttctcgagtc cggtggtgga cttgtgcaac     180
cgggcggctc cttgcgactt tcctgtgccg cctccggtta cactttcccc atgaaagaca     240
tgggatgggt gcgccaggcg ccagggaagg gtcttgagtg ggtcagcgct ataagtggga     300
gtggtggggg aacatattat gcagattcag taaaaggccg cttcactatc agtcgcgata     360
acagcaaaaa cacactgtat cttcagatga atagcttgag agctgaagat acggcggtgt     420
attactgtgc ggagccgaaa ccaatggata ccgagttcga ctaccgctcc cctggcacct     480
tggttactgt ccttgaaggc ggcgagaga gcaagtacgg gccgccgtgc ccaagttgcc      540
ctgccccgcc tgtggctggt ccttcagttt tcctgtttcc gcctaaacca aaagacactc     600
ttatgatttc tcgcacgcct gaagtcactt gtgttgtcgt agatgtcagt caggaggacc     660
cggaagtcca atttaattgg tacgtggatg gagttgaggt gcataacgcc aagacgaagc     720
cgcgagagga gcagtttaat tccacctaca gggtcgtatc cgttctcact gtccttcacc     780
aggactggct gaatgggaag gagtacaaat gcaaagtgag caataaaggc ctgccgagct     840
ccatcgaaaa aaccatttcc aaggcaaaag gccaaccccg agagccacag gtctataccc     900
tgccaccaag ccaggaggaa atgaccaaga tcaggtgagc cctcacctgt ctggtcaagg     960
gcttctaccc gtccgacatc gcggtggagt gggagagtaa cggacagcct gaaaacaatt    1020
acaagacaac cccgcctgtt ttggactctg acggctcctt ttttctgtac tctcggctta    1080
ccgtggataa gagtagatgg caagaaggca acgtcttcag ctgttccgtg atgcatgagg    1140
cgctgcataa ccattataca caaaaaagtc tgtccttgag cctgggcaaa ccttttttggg   1200
tgctggtggt ggtgggggt gtcctcgctt gctacagttt gttggtgaca gttgcctta     1260
ttatttttg ggtgcgcagt aagcggagtc gcctccttca ttccgactat atgaacatga     1320
cacctcgccg cccaggccca acgaggaaac attatcagcc atatgcacca cctagagact    1380
tgccgctta ccggtcccga gatcaaaggc ttccccccga tgcacacaaa ccacccggcg    1440
gtggctcatt tcgaacacca attcaggaag agcaggcaga cgcccacagc accctggcca    1500
agatccgggt aaagttcagc cgaagtgcag atgcgccggc ataccagcag ggccagaatc    1560
aattgtacaa tgagcttaac ctcggccgca gagaggagta tgatgtactg gataagcggc    1620
gcggacggga tcctgagatg ggaggaaagc ctcggagaaa aaatcccag gaaggacttt      1680
acaatgagtt gcagaaggat aagatggccg aagcatattc tgaaatcggg atgaaaggtg    1740
agcggcggag aggaaaaggc cacgacgggc tctaccaggg gctgagcaca gctactaaag    1800
atacatacga cgcacttcat atgcaagccc tgcctccccg cgcggccgca gcatcgataa    1860
gta                                                                  1863

<210> SEQ ID NO 37
<211> LENGTH: 1863
<212> TYPE: DNA
<213> ORGANISM: Artificial Sequence
<220> FEATURE:
<223> OTHER INFORMATION: Description of Artificial Sequence: Synthetic
```

```
         polynucleotide
<220> FEATURE:
<223> OTHER INFORMATION: PEP2-2-12 Chimeric Antigen Receptor

<400> SEQUENCE: 37
cctccataga agattctaga gctagcgaat tctgcagtcg acggtaccgc gggcccggga    60
tccaccggtc cgccgccatg gctctgcccg taactgctct ccttcttcca cttgcactgc   120
ttctccacgc ggctaggccg gaagtccaac ttctggaatc tggaggtggt ctcgtgcagc   180
ctggcggatc cctccggctt tcttgcgccg cttcaggatt cacatttcgg aaccacgaca   240
tggggtgggt taggcaagcg ccgggcaagg gcctcgaatg ggtttcagcc atatctggtt   300
ccggaggttc tacctactat gctaactcag tcaagggcag atttacgatc tcaagagaca   360
atagtaagaa cacgctgtac cttcagatga actctcttag agcagaagat acagctgtgt   420
actattgtgc tgaaccgaag cctatggata ctgagtttga ctaccctagt ccggggacgc   480
tggtaaccgt ctccagtggg ggcggagaaa gcaaatacgg tccccctgc ccctcttgcc    540 ctgccccgcc tgtggctggt ccttcagttt tcctgtttcc gcctaaacca aaagacactc   600
ttatgatttc tcgcacgcct gaagtcactt gtgttgtcgt agatgtcagt caggaggacc   660
cggaagtcca atttaattgg tacgtggatg gagttgaggt gcataacgcc aagacgaagc   720
cgcgagagga gcagtttaat tccacctaca gggtcgtatc cgttctcact gtccttcacc   780
aggactggct gaatgggaag gagtacaaat gcaaagtgag caataaaggc ctgccgagct   840
ccatcgaaaa aaccatttcc aaggcaaaag gccaaccccg agagccacag gtctataccc   900
tgccaccaag ccaggaggaa atgaccaaga atcaggtgag cctcacctgt ctggtcaagg   960
gcttctaccc gtccgacatc gcggtggagt gggagagtaa cggacagcct gaaaacaatt  1020
acaagacaac cccgcctgtt ttggactctg acggctcctt ttttctgtac tctcggctta  1080
ccgtggataa gagtagatgg caagaaggca acgtcttcag ctgttccgtg atgcatgagg  1140
cgctgcataa ccattataca caaaaaagtc tgtccttgag cctgggcaaa ccttttggg    1200 tgctggtggt ggtgggggt gtcctcgctt gctacagttt gttggtgaca gttgccttta   1260
ttattttttg ggtgcgcagt aagcggagtc gcctccttca ttccgactat atgaacatga   1320
cacctcgccg cccaggccca acgaggaaac attatcagcc atatgcacca cctagagact   1380
ttgccgctta ccggtcccga gatcaaaggc ttccccccga tgcacacaaa ccacccggcg   1440
gtggctcatt tcgaacacca attcaggaag agcaggcaga cgcccacagc accctggcca   1500
agatccgggt aaagttcagc cgaagtgcag atgcgccggc ataccagcag gccagaatc    1560 aattgtacaa tgagcttaac ctcggccgca gagaggagta tgatgtactg ataagcggc    1620 gcggacggga tcctgagatg ggaggaaagc ctcgagaaa aaatcccag gaaggacttt    1680 acaatgagtt gcagaaggat aagatggccg aagcatattc tgaaatcggg atgaaaggtg   1740
agcggcggag aggaaaaggc cacgacgggc tctaccaggg gctgagcaca gctactaaag   1800
atacatacga cgcacttcat atgcaagccc tgcctcccg cgcggccgca gcatcgataa    1860
gta                                                                1863

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: pCHD-CMV-For primer

<400> SEQUENCE: 38
ggtgggaggt ctatataagc                                                    20

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pCHD-coGFP-Rev primer

<400> SEQUENCE: 39
tgatgcggca ctcgatctc                                                     19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 2-2-1-1-Rev primer

<400> SEQUENCE: 40
cttcacggag tctgcgtag                                                     19

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 2-2-1-1-For primer

<400> SEQUENCE: 41
tcttgtcact gtatccagtg                                                    20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 2-472-2-Rev primer

<400> SEQUENCE: 42
cgtatcttca gctctcaagc                                                    20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 2-472-2-For primer

<400> SEQUENCE: 43
tggtccttca gttttcctgt 20

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 2-12-2-Rev primer

<400> SEQUENCE: 44
cagctgtatc ttctgctc 18

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Com-For-1 primer

<400> SEQUENCE: 45
agtgggagag taacggacag 20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Com-For-2 primer

<400> SEQUENCE: 46
agggccagaa tcaattgtac 20

<210> SEQ ID NO 47
<211> LENGTH: 1117
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: EXD2_K193A fusion gene block

<400> SEQUENCE: 47
ggggacaagt ttgtacaaaa aagcaggcta tggagacaga cacactcctg ctatgggtac    60
tgctgctctg ggttccaggt tccactggtg actatccata tgatgttcca gattatgctg   120
gggccagtga caagctgtac cagcggaaag agcctgtcat cagttctgtg cacaccaagg   180
tgaaggggat agcagaggtg aaagaggaga tcgtggagaa tggagtgaag aagttggtgc   240
acagtgtctt tgacaccgca gactacacct ccctttgca ggggaactct tcttcgtga    300 tgacaaactt tctcaaaaca gaaggccaag agcagcggtt gtgtcccgag tatcccaccc   360
gcaggacgct ctgttcctct gaccgaggtt gtaaaaaggg atggatggac ccgcagagca   420
aaggaattca gaccgaaagg tgtgtagtgt atgaagggaa ccagaagacc tgtgaagtct   480
ctgcctggtg ccccatcgag gcagtggaag aggccccccg gcctgctctc ttgaacagtg   540
ccgaaaactt cactgtgctc atcgcgaaca atatcgactt ccccggccac aactacacca   600

```
cgagaaacat cctgccaggt ttaaacatca cttgtacctt ccacaagact cagaatccac    660
agtgtcccat tttccgacta ggagacatct tccgagaaac aggcgataat ttttcagatg    720
tggcaattca gggcggaata atgggcattg agatctactg ggactgcaac ctagaccgtt    780
ggttccatca ctgccgtccc aaatacagtt tccgtcgcct tgacgacaag accaccaacg    840
tgtccttgta ccctggctac aacttcagat acgccaagta ctacaaggaa aacaatgttg    900
agaaagaaca aaaactcatc tcagaagagg atctgaatgc tgtgggccag gacacgcagg    960
aggtcatcgt ggtgccacac tccttgccct taaggtggt ggtgatctca gccatcctgg   1020
ccctggtggt gctcaccatc atctccctta tcatcctcat catgctttgg cagaagaagc   1080
cacgttagac ccagctttct tgtacaaagt ggtcccc                           1117
```

<210> SEQ ID NO 48
<211> LENGTH: 1117
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: EXD2_WT fusion gene block

<400> SEQUENCE: 48

```
ggggacaagt ttgtacaaaa aagcaggcta tggagacaga cacactcctg ctatgggtac     60
tgctgctctg ggttccaggt tccactggtg actatccata tgatgttcca gattatgctg    120
gggccagtga caagctgtac cagcggaaag agcctgtcat cagttctgtg cacaccaagg    180
tgaaggggat agcagaggtg aaagaggaga tcgtggagaa tggagtgaag aagttggtgc    240
acagtgtctt tgacaccgca gactacacct tccctttgca ggggaactct ttcttcgtga    300
tgacaaactt tctcaaaaca gaaggccaag agcagcggtt gtgtcccgag tatcccaccc    360
gcaggacgct ctgttcctct gaccgaggtt gtaaaaaggg atggatggac ccgcagagca    420
aaggaattca gaccggaagg tgtgtagtgt atgaagggaa ccagaagacc tgtgaagtct    480
ctgcctggtg ccccatcgag gcagtggaag aggccccccg gcctgctctc ttgaacagtg    540
ccgaaaactt cactgtgctc atcaagaaca atatcgactt ccccggccac aactacacca    600
cgagaaacat cctgccaggt ttaaacatca cttgtacctt ccacaagact cagaatccac    660
agtgtcccat tttccgacta ggagacatct tccgagaaac aggcgataat ttttcagatg    720
tggcaattca gggcggaata atgggcattg agatctactg ggactgcaac ctagaccgtt    780
ggttccatca ctgccgtccc aaatacagtt tccgtcgcct tgacgacaag accaccaacg    840
tgtccttgta ccctggctac aacttcagat acgccaagta ctacaaggaa aacaatgttg    900
agaaagaaca aaaactcatc tcagaagagg atctgaatgc tgtgggccag gacacgcagg    960
aggtcatcgt ggtgccacac tccttgccct taaggtggt ggtgatctca gccatcctgg   1020
ccctggtggt gctcaccatc atctccctta tcatcctcat catgctttgg cagaagaagc   1080
cacgttagac ccagctttct tgtacaaagt ggtcccc                           1117
```

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:

<223> OTHER INFORMATION: EXD-F1 primer

<400> SEQUENCE: 49
acaagctgta ccagcggaaa        20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: EXD2-R1 primer

<400> SEQUENCE: 50
caccaccacc ttaaagggca        20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: EXD2-F1 primer

<400> SEQUENCE: 51
acaagctgta ccagcggaaa        20

<210> SEQ ID NO 52
<211> LENGTH: 588
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PEP2-2-1-1 CAR amino acid sequence

<400> SEQUENCE: 52

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Arg Asn His Asp Met Gly Trp Val Arg Gln Ala Pro Gly Lys
    50                  55                  60

Gly Leu Glu Trp Val Ser Ala Ile Ser Gly Ser Gly Gly Ser Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Glu Pro Lys Pro Met Asp Thr Glu Phe Asp
        115                 120                 125

Tyr Arg Ser Pro Gly Thr Leu Val Thr Val Ser Ser Gly Gly Gly Glu
    130                 135                 140

Ser Lys Tyr Gly Pro Pro Cys Pro Ser Cys Pro Ala Pro Pro Val Ala
145                 150                 155                 160

```
Gly Pro Ser Val Phe Leu Phe Pro Pro Lys Pro Lys Asp Thr Leu Met
            165                 170                 175

Ile Ser Arg Thr Pro Glu Val Thr Cys Val Val Val Asp Val Ser Gln
            180                 185                 190

Glu Asp Pro Glu Val Gln Phe Asn Trp Tyr Val Asp Gly Val Glu Val
            195                 200                 205

His Asn Ala Lys Thr Lys Pro Arg Glu Glu Gln Phe Asn Ser Thr Tyr
            210                 215                 220

Arg Val Val Ser Val Leu Thr Val Leu His Gln Asp Trp Leu Asn Gly
225                 230                 235                 240

Lys Glu Tyr Lys Cys Lys Val Ser Asn Lys Gly Leu Pro Ser Ser Ile
                245                 250                 255

Glu Lys Thr Ile Ser Lys Ala Lys Gly Gln Pro Arg Glu Pro Gln Val
            260                 265                 270

Tyr Thr Leu Pro Pro Ser Gln Glu Glu Met Thr Lys Asn Gln Val Ser
            275                 280                 285

Leu Thr Cys Leu Val Lys Gly Phe Tyr Pro Ser Asp Ile Ala Val Glu
            290                 295                 300

Trp Glu Ser Asn Gly Gln Pro Glu Asn Asn Tyr Lys Thr Thr Pro Pro
305                 310                 315                 320

Val Leu Asp Ser Asp Gly Ser Phe Phe Leu Tyr Ser Arg Leu Thr Val
                325                 330                 335

Asp Lys Ser Arg Trp Gln Glu Gly Asn Val Phe Ser Cys Ser Val Met
                340                 345                 350

His Glu Ala Leu His Asn His Tyr Thr Gln Lys Ser Leu Ser Leu Ser
            355                 360                 365

Leu Gly Lys Pro Phe Trp Val Leu Val Val Val Gly Gly Val Leu Ala
            370                 375                 380

Cys Tyr Ser Leu Leu Val Thr Val Ala Phe Ile Ile Phe Trp Val Arg
385                 390                 395                 400

Ser Lys Arg Ser Arg Leu Leu His Ser Asp Tyr Met Asn Met Thr Pro
                405                 410                 415

Arg Arg Pro Gly Pro Thr Arg Lys His Tyr Gln Pro Tyr Ala Pro Pro
            420                 425                 430

Arg Asp Phe Ala Ala Tyr Arg Ser Arg Asp Gln Arg Leu Pro Pro Asp
            435                 440                 445

Ala His Lys Pro Pro Gly Gly Gly Ser Phe Arg Thr Pro Ile Gln Glu
            450                 455                 460

Glu Gln Ala Asp Ala His Ser Thr Leu Ala Lys Ile Arg Val Lys Phe
465                 470                 475                 480

Ser Arg Ser Ala Asp Ala Pro Ala Tyr Gln Gln Gly Gln Asn Gln Leu
                485                 490                 495

Tyr Asn Glu Leu Asn Leu Gly Arg Arg Glu Glu Tyr Asp Val Leu Asp
            500                 505                 510

Lys Arg Arg Gly Arg Asp Pro Glu Met Gly Gly Lys Pro Arg Arg Lys
            515                 520                 525

Asn Pro Gln Glu Gly Leu Tyr Asn Glu Leu Gln Lys Asp Lys Met Ala
            530                 535                 540

Glu Ala Tyr Ser Glu Ile Gly Met Lys Gly Glu Arg Arg Arg Gly Lys
545                 550                 555                 560

Gly His Asp Gly Leu Tyr Gln Gly Leu Ser Thr Ala Thr Lys Asp Thr
                565                 570                 575

Tyr Asp Ala Leu His Met Gln Ala Leu Pro Pro Arg
```

<210> SEQ ID NO 53
<211> LENGTH: 588
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PEP2-472-2 CAR amino acid sequence

<400> SEQUENCE: 53

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Tyr
        35                  40                  45

Thr Phe Pro Met Lys Asp Met Gly Trp Val Arg Gln Ala Pro Gly Lys
    50                  55                  60

Gly Leu Glu Trp Val Ser Ala Ile Ser Gly Ser Gly Gly Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Glu Pro Lys Pro Met Asp Thr Glu Phe Asp
        115                 120                 125

Tyr Arg Ser Pro Gly Thr Leu Val Thr Val Leu Glu Gly Gly Gly Glu
    130                 135                 140

Ser Lys Tyr Gly Pro Pro Cys Pro Ser Cys Pro Ala Pro Pro Val Ala
145                 150                 155                 160

Gly Pro Ser Val Phe Leu Phe Pro Pro Lys Pro Lys Asp Thr Leu Met
                165                 170                 175

Ile Ser Arg Thr Pro Glu Val Thr Cys Val Val Val Asp Val Ser Gln
            180                 185                 190

Glu Asp Pro Glu Val Gln Phe Asn Trp Tyr Val Asp Gly Val Glu Val
        195                 200                 205

His Asn Ala Lys Thr Lys Pro Arg Glu Glu Gln Phe Asn Ser Thr Tyr
    210                 215                 220

Arg Val Val Ser Val Leu Thr Val Leu His Gln Asp Trp Leu Asn Gly
225                 230                 235                 240

Lys Glu Tyr Lys Cys Lys Val Ser Asn Lys Gly Leu Pro Ser Ser Ile
                245                 250                 255

Glu Lys Thr Ile Ser Lys Ala Lys Gly Gln Pro Arg Glu Pro Gln Val
            260                 265                 270

Tyr Thr Leu Pro Pro Ser Gln Glu Glu Met Thr Lys Asn Gln Val Ser
        275                 280                 285

Leu Thr Cys Leu Val Lys Gly Phe Tyr Pro Ser Asp Ile Ala Val Glu
    290                 295                 300

Trp Glu Ser Asn Gly Gln Pro Glu Asn Asn Tyr Lys Thr Thr Pro Pro
305                 310                 315                 320

Val Leu Asp Ser Asp Gly Ser Phe Phe Leu Tyr Ser Arg Leu Thr Val
                325                 330                 335

Asp Lys Ser Arg Trp Gln Glu Gly Asn Val Phe Ser Cys Ser Val Met

His Glu Ala Leu His Asn His Tyr Thr Gln Lys Ser Leu Ser Leu Ser
                355                 360                 365

Leu Gly Lys Pro Phe Trp Val Leu Val Val Gly Val Leu Ala
        370                 375                 380

Cys Tyr Ser Leu Leu Val Thr Val Ala Phe Ile Ile Phe Trp Val Arg
385                 390                 395                 400

Ser Lys Arg Ser Arg Leu Leu His Ser Asp Tyr Met Asn Met Thr Pro
                405                 410                 415

Arg Arg Pro Gly Pro Thr Arg Lys His Tyr Gln Pro Tyr Ala Pro Pro
                420                 425                 430

Arg Asp Phe Ala Ala Tyr Arg Ser Arg Asp Gln Arg Leu Pro Pro Asp
                435                 440                 445

Ala His Lys Pro Pro Gly Gly Gly Ser Phe Arg Thr Pro Ile Gln Glu
                450                 455                 460

Glu Gln Ala Asp Ala His Ser Thr Leu Ala Lys Ile Arg Val Lys Phe
465                 470                 475                 480

Ser Arg Ser Ala Asp Ala Pro Ala Tyr Gln Gln Gly Gln Asn Gln Leu
                485                 490                 495

Tyr Asn Glu Leu Asn Leu Gly Arg Arg Glu Glu Tyr Asp Val Leu Asp
                500                 505                 510

Lys Arg Arg Gly Arg Asp Pro Glu Met Gly Gly Lys Pro Arg Arg Lys
                515                 520                 525

Asn Pro Gln Glu Gly Leu Tyr Asn Glu Leu Gln Lys Asp Lys Met Ala
                530                 535                 540

Glu Ala Tyr Ser Glu Ile Gly Met Lys Gly Glu Arg Arg Arg Gly Lys
545                 550                 555                 560

Gly His Asp Gly Leu Tyr Gln Gly Leu Ser Thr Ala Thr Lys Asp Thr
                565                 570                 575

Tyr Asp Ala Leu His Met Gln Ala Leu Pro Pro Arg
                580                 585

<210> SEQ ID NO 54
<211> LENGTH: 588
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PEP2-2-12 CAR amino acid sequence

<400> SEQUENCE: 54

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
                20                  25                  30

Val Gln Pro Gly Gly Ser Leu Arg Leu Ser Cys Ala Ala Ser Gly Phe
            35                  40                  45

Thr Phe Arg Asn His Asp Met Gly Trp Val Arg Gln Ala Pro Gly Lys
        50                  55                  60

Gly Leu Glu Trp Val Ser Ala Ile Ser Gly Gly Gly Ser Thr Tyr
65                  70                  75                  80

Tyr Ala Asn Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr

-continued

```
                100                     105                     110
Ala Val Tyr Tyr Cys Ala Glu Pro Lys Pro Met Asp Thr Glu Phe Asp
            115                     120                 125

Tyr Pro Ser Pro Gly Thr Leu Val Thr Val Ser Ser Gly Gly Gly Glu
        130                     135                 140

Ser Lys Tyr Gly Pro Pro Cys Pro Ser Cys Pro Ala Pro Pro Val Ala
145                     150                     155                 160

Gly Pro Ser Val Phe Leu Phe Pro Pro Lys Pro Lys Asp Thr Leu Met
                    165                     170                 175

Ile Ser Arg Thr Pro Glu Val Thr Cys Val Val Val Asp Val Ser Gln
                180                     185                 190

Glu Asp Pro Glu Val Gln Phe Asn Trp Tyr Val Asp Gly Val Glu Val
            195                     200                 205

His Asn Ala Lys Thr Lys Pro Arg Glu Glu Gln Phe Asn Ser Thr Tyr
        210                     215                 220

Arg Val Val Ser Val Leu Thr Val Leu His Gln Asp Trp Leu Asn Gly
225                     230                     235                 240

Lys Glu Tyr Lys Cys Lys Val Ser Asn Lys Gly Leu Pro Ser Ser Ile
                    245                     250                 255

Glu Lys Thr Ile Ser Lys Ala Lys Gly Gln Pro Arg Glu Pro Gln Val
                260                     265                 270

Tyr Thr Leu Pro Pro Ser Gln Glu Glu Met Thr Lys Asn Gln Val Ser
            275                     280                 285

Leu Thr Cys Leu Val Lys Gly Phe Tyr Pro Ser Asp Ile Ala Val Glu
        290                     295                 300

Trp Glu Ser Asn Gly Gln Pro Glu Asn Asn Tyr Lys Thr Thr Pro Pro
305                     310                     315                 320

Val Leu Asp Ser Asp Gly Ser Phe Phe Leu Tyr Ser Arg Leu Thr Val
                    325                     330                 335

Asp Lys Ser Arg Trp Gln Glu Gly Asn Val Phe Ser Cys Ser Val Met
                340                     345                 350

His Glu Ala Leu His Asn His Tyr Thr Gln Lys Ser Leu Ser Leu Ser
            355                     360                 365

Leu Gly Lys Pro Phe Trp Val Leu Val Val Gly Gly Val Leu Ala
        370                     375                 380

Cys Tyr Ser Leu Leu Val Thr Val Ala Phe Ile Ile Phe Trp Val Arg
385                     390                     395                 400

Ser Lys Arg Ser Arg Leu Leu His Ser Asp Tyr Met Asn Met Thr Pro
                    405                     410                 415

Arg Arg Pro Gly Pro Thr Arg Lys His Tyr Gln Pro Tyr Ala Pro Pro
                420                     425                 430

Arg Asp Phe Ala Ala Tyr Arg Ser Arg Asp Gln Arg Leu Pro Pro Asp
            435                     440                 445

Ala His Lys Pro Pro Gly Gly Gly Ser Phe Arg Thr Pro Ile Gln Glu
        450                     455                 460

Glu Gln Ala Asp Ala His Ser Thr Leu Ala Lys Ile Arg Val Lys Phe
465                     470                     475                 480

Ser Arg Ser Ala Asp Ala Pro Ala Tyr Gln Gln Gly Gln Asn Gln Leu
                    485                     490                 495

Tyr Asn Glu Leu Asn Leu Gly Arg Arg Glu Glu Tyr Asp Val Leu Asp
                500                     505                 510

Lys Arg Arg Gly Arg Asp Pro Glu Met Gly Gly Lys Pro Arg Arg Lys
            515                     520                 525
```

Asn Pro Gln Glu Gly Leu Tyr Asn Glu Leu Gln Lys Asp Lys Met Ala
            530                 535                 540

Glu Ala Tyr Ser Glu Ile Gly Met Lys Gly Glu Arg Arg Arg Gly Lys
545                 550                 555                 560

Gly His Asp Gly Leu Tyr Gln Gly Leu Ser Thr Ala Thr Lys Asp Thr
                565                 570                 575

Tyr Asp Ala Leu His Met Gln Ala Leu Pro Pro Arg
            580                 585

<210> SEQ ID NO 55
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Met Val Leu Ser Leu Leu Tyr Leu Leu Thr Ala Leu Pro Gly Ile
1               5                   10                  15

Leu Ser Glu Val Gln Pro Gln Gln Ser Gly Pro Ser Leu Val Lys Pro
            20                  25                  30

Ser Gln Thr Leu Ser Leu Thr Cys Ser Val Thr Gly Asp Ser Ile Thr
        35                  40                  45

Ser Gly Tyr Trp Asn Trp Ile Arg Ile Phe Pro Glu Asn Lys Ile Asp
    50                  55                  60

Tyr Met Gly Tyr Ile Asn Tyr Ser Gly Thr Thr Tyr Tyr Asn Pro Ser
65                  70                  75                  80

Leu Lys Ser Arg Val Ser Ile Thr Arg Asp Thr Ser Asn Asn Gln Tyr
                85                  90                  95

Tyr Asp Arg Leu Asn Ser Val Thr Ala Glu Asp Thr Ala Thr Tyr Tyr
            100                 105                 110

Cys Ala Lys Gly Arg Asn Thr Tyr Ser Gly Phe Ala Phe Trp Gly Pro
        115                 120                 125

Gly Thr Leu Val Thr Val Ser Ala Ala Lys Thr Thr Pro Pro Ser Val
    130                 135                 140

Tyr Pro Leu Ala Pro Gly Cys Gly Asp Thr Thr Gly Ser Ser
145                 150                 155

<210> SEQ ID NO 56
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Met Met Val Leu Ser Leu Leu Tyr Leu Leu Thr Ala Leu Pro Gly Ile
1               5                   10                  15

Asp Ser Glu Val Gln Leu Gln Glu Ser Gly Pro Ser Leu Val Lys Pro
            20                  25                  30

Ser Gln Thr Leu Ser Leu Thr Cys Ser Val Thr Gly Asp Ser Ile Thr
        35                  40                  45

Ser Gly Tyr Trp Asn Trp Ile Arg Lys Phe Pro Gly Asn Lys Leu Glu
    50                  55                  60

Tyr Met Gly Tyr Ile Asn Lys Ser Gly Asn Thr Tyr Tyr Asn Pro Ser
65                  70                  75                  80

Leu Asn Ser Arg Leu Ser Ile Thr Arg Asp Thr Ser Lys Asn Gln Tyr
                85                  90                  95

Asn Leu Gln Leu Ser Ser Val Thr Ala Glu Asp Thr Ala Thr Tyr Tyr
            100                 105                 110

Cys Ala Arg Gly Arg Ala Ile Tyr Tyr Tyr Lys Ser Gly Phe Ala Tyr
        115                 120                 125

Trp Gly Gln Gly Thr Leu Val Thr Val Ser Ala Ala Lys Thr Thr Pro
    130                 135                 140

Pro Ser Val Tyr Pro Leu Ala Pro Gly Cys Gly Asp Thr Thr Gly
145                 150                 155

<210> SEQ ID NO 57
<211> LENGTH: 159
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Met Val Leu Ser Leu Leu Tyr Leu Leu Thr Ala Leu Pro Gly Ile
1               5                   10                  15

Leu Ser Glu Val Gln Leu Gln Glu Ser Gly Pro Ser Leu Val Lys Pro
            20                  25                  30

Ser Gln Thr Leu Ser Leu Thr Cys Ser Val Thr Gly Asp Ser Ile Thr
        35                  40                  45

Ser Gly Tyr Trp Asn Trp Ile Arg Lys Phe Pro Gly Asn Lys Leu Glu
    50                  55                  60

Tyr Met Gly Tyr Ile Asn Tyr Ser Gly Ser Thr Tyr Tyr Asn Pro Ser
65                  70                  75                  80

Leu Asn Ser Arg Leu Ser Ile Thr Arg Asp Thr Ser Lys Asn Gln Tyr
                85                  90                  95

Ser Leu Gln Leu Ser Ser Val Thr Ala Glu Asp Thr Ala Thr Tyr Tyr
            100                 105                 110

Cys Ala Arg Gly Arg Ala Ile Phe Tyr Tyr Lys Ser Gly Phe Val Tyr
        115                 120                 125

Trp Gly Gln Gly Thr Leu Val Thr Val Ser Ala Ala Lys Thr Thr Ala
    130                 135                 140

Pro Ser Val Tyr Pro Leu Ala Pro Val Cys Gly Gly Thr Thr Gly
145                 150                 155

<210> SEQ ID NO 58
<211> LENGTH: 163
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Met Asp Leu Arg Leu Ser Cys Ala Phe Ile Ile Val Leu Leu Lys Gly
1               5                   10                  15

Val Gln Ser Glu Val Lys Leu Glu Glu Ser Gly Gly Gly Leu Val Gln
            20                  25                  30

Pro Gly Gly Ser Met Lys Leu Ser Cys Val Ala Ser Gly Phe Thr Phe
        35                  40                  45

Ser Ser Tyr Trp Met Ser Trp Val Arg Gln Ser Pro Glu Lys Gly Leu
    50                  55                  60

```
Glu Trp Val Ala Glu Ile Arg Leu Lys Ser Asp Asn Tyr Ala Thr His
 65                  70                  75                  80

Tyr Ala Glu Ser Val Lys Gly Lys Phe Thr Ile Ser Arg Asp Asp Ser
                 85                  90                  95

Lys Ser Arg Leu Tyr Leu Gln Met Asn Ser Leu Arg Ala Glu Asp Thr
            100                 105                 110

Gly Ile Tyr Tyr Cys Arg Leu Val Tyr Gly Asn Tyr Asp Ala Met
        115                 120                 125

Asp Tyr Trp Gly Gln Gly Thr Ser Val Thr Val Ser Ser Arg Ser Gln
    130                 135                 140

Ser Phe Pro Asn Val Phe Pro Leu Val Ser Cys Glu Ser Pro Leu Tyr
145                 150                 155                 160

Asp Lys Asn

<210> SEQ ID NO 59
<211> LENGTH: 147
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Met Thr Phe Gly Leu Ser Leu Ile Phe Leu Val Leu Val Leu Thr Gly
 1               5                  10                  15

Val Gln Cys Glu Val Met Leu Val Glu Ser Gly Gly Gly Leu Val Arg
             20                  25                  30

Pro Gly Gly Ser Leu Lys Leu Ser Cys Thr Ala Ser Gly Phe Thr Phe
        35                  40                  45

Ser Gly Tyr Ala Met Ser Trp Val Arg Gln Thr Pro Glu Lys Arg Leu
    50                  55                  60

Glu Trp Val Ala Thr Ile Asp Ser Gly Gly Tyr Asn Thr Tyr Tyr Pro
 65                  70                  75                  80

Asp Ser Val Lys Gly Arg Thr Phe Thr Leu Ser Arg Asp Asn Ala Arg
                 85                  90                  95

Asn Thr Leu Ser Leu Gln Met Ser Ser Leu Arg Ser Glu Asp Thr Ala
            100                 105                 110

Ile Tyr Tyr Cys Ser Thr Ser Leu Val Glu Phe Phe Asp Tyr Trp Gly
        115                 120                 125

Pro Gly Thr Ala Leu Thr Val Ser Ser Ala Lys Thr Thr Pro Pro Ser
    130                 135                 140

Val Tyr Pro
145

<210> SEQ ID NO 60
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Met Asn Phe Gly Phe Ser Leu Ile Pro Leu Val Leu Val Leu Lys Gly
 1               5                  10                  15

Val Gln Cys Glu Val Lys Leu Val Glu Ser Gly Gly Gly Leu Val Gln
             20                  25                  30
```

Pro Gly Gly Ser Leu Lys Leu Ser Cys Ala Ala Ser Gly Phe Thr Pro
            35                  40                  45

Ser Ser Tyr Ala Met Ser Trp Val Arg Gln Ile Pro Glu Arg Arg Leu
 50                  55                  60

Glu Trp Val Ala Ser Ile Gly Tyr Ser Gly Arg Thr Tyr Tyr Pro Asp
 65                  70                  75                  80

Ser Val Lys Gly Arg Phe Thr Ile Ser Arg Asp Asn Ser Arg Asn Ile
                 85                  90                  95

Leu Tyr Leu Gln Met Ser Ser Leu Gly Ser Glu Asp Thr Ala Met Tyr
                100                 105                 110

Phe Cys Ala Arg Gly Ile Phe His Tyr Thr Ser Thr Ser Tyr Phe Asp
            115                 120                 125

Tyr Trp Gly Gln Gly Thr Thr Leu Thr Val Ser Ser Ala Lys Thr Thr
130                 135                 140

Leu Pro Ser Val Tyr Pro Leu Ala Pro Gly Cys Gly Asp Thr Thr Gly
145                 150                 155                 160

<210> SEQ ID NO 61
<211> LENGTH: 145
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Met Gly Trp Ser Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Lys
                 20                  25                  30

Pro Gly Ala Ser Val Lys Ile Ser Cys Lys Thr Ser Gly His Thr Phe
            35                  40                  45

Thr Glu Tyr Ala Leu His Trp Val Arg Gln Ser His Gly Lys Ser Phe
 50                  55                  60

Glu Trp Ile Gly Gly Ile Asn Pro Asn Asn Gly Gly Ala Thr Tyr Asn
 65                  70                  75                  80

Gln Lys Phe Lys Gly Lys Ala Thr Leu Thr Val Asp Lys Ser Ser Ser
                 85                  90                  95

Thr Pro Phe Met Glu Leu His Ser Leu Thr Phe Glu Asp Ser Ala Val
                100                 105                 110

Tyr Phe Cys Ala Arg Ala Tyr Tyr Ala Met Asp Tyr Trp Gly Gln Gly
            115                 120                 125

Thr Ser Val Thr Val Ser Ser Ala Lys Thr Thr Pro Pro Ser Val Tyr
130                 135                 140

Pro
145

<210> SEQ ID NO 62
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Gln Leu Val Gln Ser Gly Pro Glu Leu Lys Lys Gly Glu Thr
1               5                   10                  15

Val Lys Ile Ser Cys Cys Lys Ala Ser Gly Tyr Thr Phe Thr Tyr Tyr
            20                  25                  30

Gly Met Asn Trp Val Arg Gln Ala Pro Gly Lys Gly Leu Lys Trp Leu
            35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Arg Thr Ala Phe
65                  70                  75                  80

Leu Gln Ile Asn Asn Leu Lys Asn Glu Asp Thr Ala Thr Tyr Phe Cys
                85                  90                  95

Ala Arg Ser Arg Tyr Leu Gly Val Leu Ser Tyr Trp Gly Gln Gly Thr
            100                 105                 110

Leu Val Thr Val Ser
            115

<210> SEQ ID NO 63
<211> LENGTH: 155
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Met Ala Trp Val Trp Thr Leu Leu Phe Leu Met Ala Ala Ala Gln Ser
1               5                   10                  15

Ala Gln Ala Gln Ile His Leu Val Gln Ser Gly Pro Glu Leu Lys Lys
            20                  25                  30

Pro Gly Glu Thr Val Glu Ile Ser Cys Lys Ala Ser Cys Tyr Thr Phe
            35                  40                  45

Thr Asn His Gly Met Asn Trp Val Lys Gln Thr Pro Gly Lys Gly Leu
    50                  55                  60

Lys Trp Met Gly Trp Ile Asn Thr Tyr Thr Gly Gln Ser Ile Tyr Ser
65                  70                  75                  80

Asp Asp Phe Lys Gly Arg Phe Ala Phe Ser Met Glu Thr Ser Ala Thr
                85                  90                  95

Thr Ala Tyr Leu Gln Ile Asn Asn Leu Lys Asp Glu Asp Thr Ala Thr
            100                 105                 110

Tyr Phe Cys Ala Gly Gly Lys Gly His Phe Asp Ser Trp Gly Gln Gly
            115                 120                 125

Thr Thr Leu Thr Val Ser Ser Ala Lys Thr Thr Ala Pro Ser Val Tyr
    130                 135                 140

Pro Leu Ala Pro Val Cys Gly Gly Thr Thr Gly
145                 150                 155

<210> SEQ ID NO 64
<211> LENGTH: 383
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (17)..(106)
<220> FEATURE:
<221> NAME/KEY: CDS
<222> LOCATION: (154)..(183)

<400> SEQUENCE: 64

```
                                                            -continued cttggggata tccacc atg gag aca gac aca ctc ctg cta tgg gta ctg ctg         52
              Met Glu Thr Asp Thr Leu Leu Leu Trp Val Leu Leu
                1               5                   10 ctc tgg gtt cca ggt tcc act ggt gac tat cca tat gat gtt cca gat         100
Leu Trp Val Pro Gly Ser Thr Gly Asp Tyr Pro Tyr Asp Val Pro Asp
        15                  20                  25 tat gct ggggcccagc cggccagatc tcccgggatc cgcggctgca ggtcgac gaa         156
Tyr Ala                                                     Glu
    30 caa aaa ctc atc tca gaa gag gat ctg aatgctgtgg gccaggacac              203
Gln Lys Leu Ile Ser Glu Glu Asp Leu
            35                  40 gcaggaggtc atcgtggtgc cacactcctt gcccttaag gtggtggtga tctcagccat        263
cctggccctg gtggtgctca ccatcatctc ccttatcatc ctcatcatgc tttggcagaa       323
gaagccacgt taggcggccg ctcgagatca gcctcgactg tgccttctag ttgccagcca       383

<210> SEQ ID NO 65
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Met Glu Thr Asp Thr Leu Leu Leu Trp Val Leu Leu Leu Trp Val Pro
1               5                   10                  15

Gly Ser Thr Gly Asp Tyr Pro Tyr Asp Val Pro Asp Tyr Ala
            20                  25                  30

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Glu Gln Lys Leu Ile Ser Glu Glu Asp Leu
1               5                   10
```

CHIMERIC ANTIGEN RECEPTORS AND USES THEREOF

PRIORITY CLAIM

This application is a national stage filing under 35 U.S.C. § 371 of PCT/AU2016/050851, filed Sep. 10, 2016, which claims priority from Australian provisional patent application number 2015903719 filed on 11 Sep. 2015, the contents of each of which are to be taken as incorporated herein by this reference.

SEQUENCE LISTING

The instant application contains a Sequence Listing which has been submitted electronically in ASCII format and is hereby incorporated by reference in its entirety. Said ASCII copy, created on Mar. 30, 2021, is named FPB-00101_SL.txt and is 98,251 bytes in size.

FIELD OF THE INVENTION

The present invention relates to chimeric antigen receptors, T cells expressing chimeric antigen receptors and methods of using chimeric antigen receptors for the prevention and/or treatment of cancer.

BACKGROUND OF THE INVENTION

The immune system has highly evolved and specific mechanisms that protect us from a range of pathologies. Amongst these pathologies is the detection and elimination of unwanted pathogens such as bacterial infections, virally infected cells, and importantly, mutated cells that may cause malignant neoplasia (cancer). The ability for the immune system to prevent the formation and growth of cancers is dependent on the ability of the cells of the immune system to distinguish between a 'healthy' cell and a 'diseased' (e.g. neoplastic or pre-neoplastic) cell. This is achieved by recognition of cell markers (antigens) that are indicative of the transition in a cell from a healthy state to a diseased state.

There have been many attempts to develop immunotherapeutic approaches to treat cancer by manipulating or directing the immune system to target cells expressing cancer cell antigens. Immunotherapeutic approaches have largely centred on either exploiting the humoral immune system by utilising isolated or engineered antibodies or, more recently, the cellular arm of the immune system.

Early attempts to utilise cellular immunotherapy for the treatment of cancer utilised T lymphocytes isolated from tumours and expanded ex vivo. Whilst this approach has provided some initial promise in early investigations, there are many technical challenges associated with this approach. The ability to isolate and expand T cell populations to clinically relevant numbers is technically challenging and the poorly controlled nature of the expansion results in a final T cell population that is distinctly heterogeneous, and may contain only a small number of cancer antigen-specific T cells. As a result, the efficacy of this method is unpredictable and variable.

In order to address some of the shortfalls related to the use of ex vivo expanded tumour-isolated T cells, chimeric antigen receptors (CARs or artificial T cell receptors) began to be developed in the late 1980s. Chimeric antigen receptors are created by linking an extracellular region that is specific for a desired antigen to a signalling region, resulting in an antigen-specific receptor that can induce T cell function.

Transformation of isolated T cells with CARs results in a population of T cells that are specific for a given antigen. As a result, large populations of antigen-specific T cells can be generated and used for immunotherapy.

Initial clinical trials of CAR-transformed T cells specific for tumour associated antigens were promising. However, the efficacy of the CAR-transformed T cells led to significant hypercytokinemia, and ultimately death in some patients. These adverse effects are largely believed to be induced by on-target, but off-tumour activity of the CAR-transformed T cells induced as a result of endogenous expression of the cognate antigen for the CAR on healthy, non-cancerous, cell populations.

It is therefore apparent that there is a need for the development of a CAR that targets a tumour-associated antigen which is selectively expressed by cancerous cells but not endogenously expressed on non-cancerous cells.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

The present invention is predicated in part on the recognition that due to the significant 'on-target' but 'off-tumour' activity of CAR-expressing immune cells, there is a need for the development of a CAR, and a genetically modified cell expressing the same, which targets a marker specifically associated with a range of neoplastic (cancerous) or pre-neoplastic (pre-cancerous) cells. The inventors have recognised that a dysfunctional $P2X_7$ receptor is a suitable marker for targeting with a CAR.

Accordingly, in a first aspect, the present invention provides a chimeric antigen receptor including an antigen-recognition domain and a signalling domain, wherein the antigen-recognition domain recognises a dysfunctional $P2X_7$ receptor.

In some embodiments, the antigen-recognition domain recognises an epitope associated with an adenosine triphosphate (ATP)-binding site of the dysfunctional $P2X_7$ receptor. In some embodiments, the dysfunctional $P2X_7$ receptor has a reduced capacity to bind ATP at the ATP-binding site compared to an ATP-binding capacity of a wild-type (functional) $P2X_7$ receptor. In some embodiments the dysfunctional $P2X_7$ receptor cannot bind ATP at the ATP-binding site.

In some embodiments, the dysfunctional $P2X_7$ receptor has a conformational change that renders the receptor dysfunctional. In some embodiments, the conformational change is a change of an amino acid from the trans-conformation to the cis-conformation. In some embodiments, the amino acid that has changed from a trans-conformation to a cis-conformation is proline at amino acid position 210 of the dysfunctional $P2X_7$ receptor.

In some embodiments, the antigen-recognition domain recognises an epitope that includes the proline at amino acid position 210 of the dysfunctional $P2X_7$ receptor. In some embodiments, the antigen-recognition domain recognises an epitope that includes one or more amino acid residues spanning from glycine at amino acid position 200 to cysteine at amino acid position 216, inclusive, of the dysfunctional $P2X_7$ receptor.

The antigen-recognition domain of the CAR can be any suitable molecule that can interact with and specifically recognise a dysfunctional $P2X_7$ receptor. However, in some embodiments, the antigen-recognition domain includes amino acid sequence homology to the amino acid sequence of an antibody, or a fragment thereof, that binds to the dysfunctional $P2X_7$ receptor. In some embodiments, the antigen-recognition domain includes amino acid sequence homology to the amino acid sequence of a fragment-antigen binding (Fab) portion of an antibody that binds to a dysfunctional $P2X_7$ receptor. In some embodiments, the antibody is a humanised antibody.

In some embodiments, the antigen-recognition domain includes amino acid sequence homology to the amino acid sequence of a single-chain variable fragment (scFv) or a multivalent scFv that binds to a dysfunctional $P2X_7$ receptor. In some embodiments, the multivalent scFv is a di-valent or tri-valent scFv.

In some embodiments, the antigen-recognition domain includes amino acid sequence homology to a single-antibody domain (sdAb) that binds to a dysfunctional $P2X_7$ receptor.

In some embodiments, the antigen-recognition domain includes a binding peptide that includes amino acid sequence homology to one or more CDR regions of an antibody that binds to a dysfunctional $P2X_7$ receptor. In some embodiments, the biding peptide includes amino acid sequence homology to the CDR1, 2 and 3 domains of the $V_H$ and/or $V_L$ chain of an antibody that binds to a dysfunctional $P2X_7$ receptor. In some embodiments, the antigen recognition domain includes one or more amino acid sequences which are at least 50%, 60%, 70%, 80%, 90% or 94% identical to any one of the regions spanning positions 30 to 35, 50 to 67 or 98 to 108 of the sequences set forth in SEQ ID NOS: 10, 32, 33 or 34. In some embodiments, the antigen recognition domain includes one or more of the sequences spanning positions 30 to 35, 50 to 67 or 98 to 108 of the sequences set forth in SEQ ID NOS: 10, 32, 33 or 34. In some embodiments, the antigen recognition domain includes one or more of the sequences set forth in SEQ ID NOS: 10, 32, 33 or 34.

In some embodiments, the signalling domain includes a portion derived from an activation receptor. In some embodiments, the activation receptor is a member of the CD3 co-receptor complex or is an Fc receptor. In some embodiments, the portion derived from the CD3 co-receptor complex is CD3-C. In some embodiments, the portion derived from the Fc receptor is FcεRI or FcγRI.

In some embodiments, the signalling domain includes a portion derived from a co-stimulatory receptor. In some embodiments, the signalling domain includes a portion derived from an activation receptor and a portion derived from a co-stimulatory receptor. In some embodiments, the co-stimulatory receptor is selected from the group consisting of CD27, CD28, CD30, CD40, DAP10, OX40, 4-1BB (CD137) and ICOS.

In a second aspect, the present invention provides a nucleic acid molecule including a nucleotide sequence encoding the chimeric antigen receptor according to the first aspect of the invention.

In a third aspect, the present invention provides a nucleic acid construct that includes a nucleic acid molecule according to the second aspect of the invention. In some embodiments, expression of the nucleic acid molecule is under the control of a transcriptional control sequence. In some embodiments, the transcriptional control sequence may be a constitutive promoter or an inducible promoter.

In some embodiments of the third aspect of the invention, the nucleic acid construct further includes an internal ribosome entry site (IRES) that allows for translation initiation within the mRNA once expressed from the nucleic acid construct.

In some embodiments of the third aspect of the invention, the nucleic acid construct is a vector such as a viral vector, which can be used to transform a T cell to induce expression of the CAR.

In a fourth aspect, the present invention provides a genetically modified cell that includes a CAR according to the first aspect of the invention. In some embodiments, the cell includes two or more different CARs.

In a fifth aspect, the present invention provides a genetically modified cell that includes a nucleic acid molecule according to the second aspect of the invention, or a nucleic acid construct according to the third aspect of the invention, or a genomically integrated form of the construct. In some embodiments, the nucleic acid molecule or the nucleic acid construct encodes two or more different CARs.

In some embodiments of the fourth and fifth aspects of the invention, the two or more different CARs have different signalling domains.

In some embodiments of the fourth and fifth aspects of the invention, the cell includes a first CAR with a signalling domain including a portion derived from an activation receptor and a second CAR with a signalling domain including a portion derived from a co-stimulatory receptor. In some embodiments, the activation receptor is a member of the CD3 co-receptor complex or is an Fc receptor. In some embodiments, the co-stimulatory receptor is selected from the group consisting of CD27, CD28, CD30, CD40, DAP10, OX40, 4-1BB (CD137) and ICOS.

In some embodiments of the fourth and fifth aspects of the invention, the cell is further modified so as to constitutively express co-stimulatory receptors. In some embodiments, the cell is further modified so as to express ligands for the co-stimulatory receptors, thereby facilitating auto-stimulation of the cell.

In some embodiments of the fourth and fifth aspects of the invention, the cell is further modified to secrete cytokines. In some embodiments, the cytokines are selected from the group consisting of IL-2, IL-7, IL-12, IL-15, IL-17 and IL-21, or a combination thereof.

In some embodiments of the fourth and fifth aspects of the invention, the cell is a leukocyte. In some embodiments, the cell is a Peripheral Blood Mononuclear Cell (PBMC), a lymphocyte, a T cell (including a CD4+ T cell or a CD8+ T cell), a natural killer cell, or a natural killer T cell.

In a sixth aspect, the present invention provides a method of killing a cell expressing a dysfunctional $P2X_7$ receptor, the method including exposing the cell expressing a dysfunctional $P2X_7$ receptor to a genetically modified cell having a chimeric antigen receptor, wherein the chimeric antigen receptor is directed against a dysfunctional $P2X_7$ receptor.

In some embodiments of the sixth aspect of the invention, the CAR directly recognises the dysfunctional $P2X_7$ receptor, or recognises the dysfunctional $P2X_7$ receptor via an intermediate. In some embodiments, the intermediate is a probe that binds to a dysfunctional $P2X_7$ receptor and the CAR recognises the probe. In some embodiments, the probe is an antibody or an aptamer. In some embodiments, the probe includes a tag and the CAR recognises the tag.

In a seventh aspect, the present invention provides a method of killing a cell expressing a dysfunctional P2X7, the method including exposing the cell expressing a dysfunctional $P2X_7$ receptor to a genetically modified cell according to the fourth or fifth aspects of the invention.

In some embodiments of the sixth and seventh aspects of the invention, the cell expressing a dysfunctional $P2X_7$ receptor is exposed to the genetically modified cell together with an exogenous cytokine. In some embodiments, the genetically modified cell is a genetically modified cell, autologous to the cell expressing a dysfunctional $P2X_7$ receptor.

In some embodiments of the sixth and seventh aspects of the invention, the cell expressing a dysfunctional $P2X_7$ receptor is a cancer cell. In some embodiments the cancer is selected from the group consisting of; brain cancer, oesophageal cancer, mouth cancer, tongue cancer, thyroid cancer, lung cancer, stomach cancer, pancreatic cancer, kidney cancer, colon cancer, rectal cancer, prostate cancer, bladder cancer, cervical cancer, epithelial cell cancers, skin cancer, leukaemia, lymphoma, myeloma, breast cancer, ovarian cancer, endometrial cancer and testicular cancer. In some embodiments the cancer is selected from the group consisting of; lung cancer, oesophageal cancer, stomach cancer, colon cancer, prostate cancer, bladder cancer, cervical cancer, vaginal cancers, epithelial cell cancers, skin cancer, blood-related cancers, breast cancer, endometrial cancer, uterine cancer and testicular cancer.

In some embodiments of the sixth and seventh aspects of the invention, the cancer is metastatic. In some embodiments, the cancer is stage Ill cancer or is stage IV cancer.

In an eighth aspect, the present invention provides a method of expanding in vitro the genetically modified cell according to the fourth or fifth aspects of the invention, the method including the step of exposing the cell to an antigen for the CAR. In some embodiments, the method includes the further step of exposing the cell to a cytokine.

In a ninth aspect, the present invention provides a method of expanding in vitro the genetically modified cell according to the fourth or fifth aspects of the invention, the method including the step of exposing the cell to an antigen for the CAR and simultaneously exposing the cell to a cytokine.

In some embodiments of the eighth and ninth aspects of the invention, the cytokine is a member of the IL-2 subfamily, the interferon subfamily, the IL-10 subfamily, the IL-1 subfamily, the IL-17 subfamily or the TGF-β subfamily.

In some embodiments of the eighth and ninth aspects of the invention, the cytokine is selected from the group consisting of IFN-γ, IL-2, IL-5, IL-7, IL-8, IL-10, IL-12, IL-13, IL-15, IL-17, IL-18, TNF-α, TGF-β1, TGF-β2, TGF-β3 and GM-CSF, or a combination thereof.

In a tenth aspect, the present invention provides a method of expanding in vitro the genetically modified cell according to the fourth or fifth aspects of the invention, the method including exposing the cell to immobilised anti-CD3 and anti-CD28 antibodies. In some embodiments of the tenth aspect of the invention, the antibodies are immobilised on a beaded substrate (for example on "Human Activator" Dynabeads™). In some embodiments of the tenth aspect of the invention, the antibodies are immobilised on a surface of a tissue culture vessel such as a surface of a culture flask, plate or bioreactor.

In an eleventh aspect, the present invention provides a pharmaceutical composition including a genetically modified cell according to the fourth or fifth aspects of the invention and a pharmaceutically acceptable carrier. In some embodiments, the pharmaceutical composition includes suitable adjuvants which may consist of cytokines. In some embodiments, the pharmaceutical composition may also include an intermediate as described herein.

BRIEF DESCRIPTION OF THE FIGURES

For a further understanding of the aspects and advantages of the present invention, reference should be made to the following detailed description, taken in conjunction with the accompanying drawings.

FIG. 5—shows microscopy images of 293T cells transfected with plasmids required for the construction of lentiviral vectors containing the BLIV-CAR-short hinge construct and 293T cells transduced with supernatant containing the lentiviral vectors.

FIG. 6—shows microscopy images of 293T cells transfected with plasmids required for the construction of lentiviral vectors containing the BLIV-CAR-long hinge construct and 293T cells transduced with supernatant containing the lentiviral vectors.

FIG. 10—Alignment of the PEP2-2-1-1, PEP2-472-2 and PEP2-2-12 binding peptides with antibodies directed against the nf-$P2X_7$ receptor. FIG. 10 discloses SEQ ID NOS 55-58, 33, 32, 34, and 59-63, respectively, in order of appearance.

FIG. 17—Illustration of the backbone of the fusion protein for generation of non-functional and functional $P2X_7$ receptors. FIG. 17 discloses SEQ ID NOS 64-66, respectively, in order of appearance.

FIG. 22—Graph illustrating the killing of nfP2X$_7$ expressing HEK target cells and 231 breast cancer cell by T cells expressing PEP2-2-1-1, PEP2-472-2 CARs

DETAILED DESCRIPTION OF THE INVENTION

Figure 1:
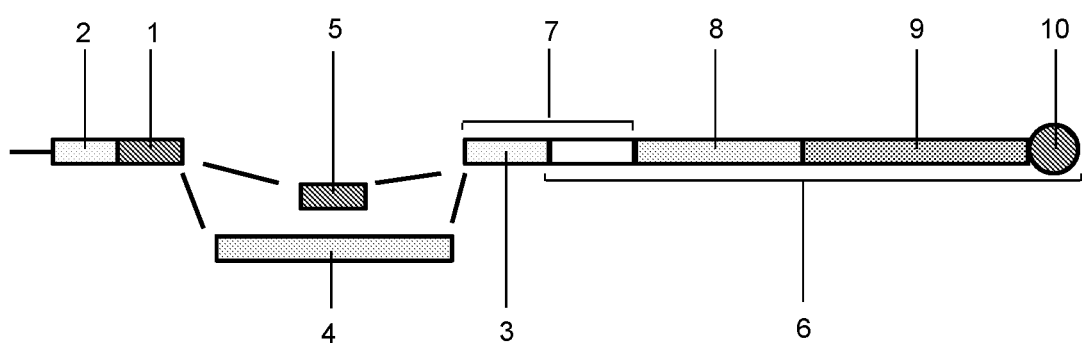
FIG. 1—a schematic showing the arrangement of an anti-non-functional (nf) $P2X_7$ receptor chimeric antigen receptor (CAR) according to an embodiment of the present invention.

The nucleotide and polypeptide sequences referred to herein are represented by a sequence identifier number (SEQ ID NO:). A summary of the sequence identifiers is provided in Table 1. A sequence listing is also provided at the end of the specification.

TABLE 1

Summary of Sequence Identifiers

| Sequence Identifier | Sequence |
|---|---|
| SEQ ID NO: 1 | Human P2X$_7$ receptor mRNA sequence |
| SEQ ID NO: 2 | Human P2X$_7$ receptor coding (cDNA) sequence |
| SEQ ID NO: 3 | Human P2X$_7$ receptor amino acid sequence |
| SEQ ID NO: 4 | CD3ζ chain amino acid sequence |
| SEQ ID NO: 5 | CD3ε chain amino acid sequence |
| SEQ ID NO: 6 | CD3γ chain amino acid sequence |
| SEQ ID NO: 7 | CD3δ chain amino acid sequence |
| SEQ ID NO: 8 | FcεR1 amino acid sequence |
| SEQ ID NO: 9 | FcγRI amino acid sequence |
| SEQ ID NO: 10 | PEP2-2-3 amino acid sequence |
| SEQ ID NO: 11 | PEP2-2-3 nucleotide sequence |
| SEQ ID NO: 12 | CD8a signalling amino acid sequence |
| SEQ ID NO: 12 | CD8a signalling nucleotide sequence |
| SEQ ID NO: 14 | Long hinge amino acid sequence |
| SEQ ID NO: 15 | Long hinge nucleotide sequence |
| SEQ ID NO: 16 | Short hinge amino acid sequence |
| SEQ ID NO: 17 | Short hinge nucleotide sequence |
| SEQ ID NO: 18 | Amino acid sequence of a portion of the CD28 co-stimulatory receptor |
| SEQ ID NO: 19 | Nucleotide sequence coding for SEQ ID NO: : 18 |
| SEQ ID NO: 20 | Amino acid sequence of a portion of the OX40 co-stimulatory receptor |
| SEQ ID NO: 21 | Nucleotide sequence coding for SEQ ID NO: : 20 |
| SEQ ID NO: 22 | Amino acid sequence of a portion of the CD3 zeta co-receptor complex |
| SEQ ID NO: 23 | Nucleotide sequence coding for SEQ ID NO: : 22 |
| SEQ ID NO: 24 | P2A amino acid sequence |
| SEQ ID NO: 25 | P2A nucleotide sequence |
| SEQ ID NO: 26 | PEP2-2-3 binding peptide CAR amino acid sequence - long hinge |
| SEQ ID NO: 27 | PEP2-2-3 binding peptide CAR amino acid sequence - short hinge |
| SEQ ID NO: 28 | PEP2-2-3 binding peptide CAR nucleotide sequence - long hinge |
| SEQ ID NO: 29 | PEP2-2-3 binding peptide CAR nucleotide sequence - short hinge |
| SEQ ID NO: 30 | Human CD8 leader amino acid sequence |
| SEQ ID NO: 31 | Human CD8 nucleotide sequence |
| SEQ ID NO: 32 | Amino acid sequence of PEP2-2-1-1 binding peptide |
| SEQ ID NO: 33 | Amino acid sequence of PEP2-472-2 binding peptide |
| SEQ ID NO: 34 | Amino acid sequence of PEP2-2-12 binding peptide |
| SEQ ID NO: 35 | Nucleotide sequence of PEP2-2-1-1 CAR |
| SEQ ID NO: 36 | Nucleotide sequence of PEP2-472-2 CAR |
| SEQ ID NO: 37 | Nucleotide sequence of PEP2-2-12 CAR |
| SEQ ID NO: 38 | pCHD-CMV-For primer |
| SEQ ID NO: 39 | pCHD-coGFP-Rev primer |
| SEQ ID NO: 40 | 2-2-1-1-Rev primer |
| SEQ ID NO: 41 | 2-2-1-1-For primer |
| SEQ ID NO: 42 | 2-472-2-Rev primer |
| SEQ ID NO: 43 | 2-472-2-For primer |
| SEQ ID NO: 44 | 2-12-2-Rev primer |
| SEQ ID NO: 45 | Com-For-1 primer |
| SEQ ID NO: 46 | Com-For-2 primer |
| SEQ ID NO: 47 | EXD2_K193A gene block |
| SEQ ID NO: 48 | EXD2_WT gene block |
| SEQ ID NO: 49 | EXD-F1 primer |
| SEQ ID NO: 50 | EXD2-R1 primer |
| SEQ ID NO: 51 | EXD2-F1 primer |
| SEQ ID NO: 52 | Amino acid sequence of PEP2-2-1-1 CAR |
| SEQ ID NO: 53 | Amino acid sequence of PEP2-472-2 CAR |
| SEQ ID NO: 54 | Amino acid sequence of PEP2-2-12 CAR |

The inventors have recognized that due to the significant 'on-target' but 'off-tumour' activity of chimeric antigen receptor (CAR) expressing immune cells, there is a need for the development of a CAR, and a genetically modified cell expressing the same, which targets a marker specifically associated with neoplastic (cancerous) or pre-neoplastic (pre-cancerous) cells. The inventors have recognised that a dysfunctional P2X$_7$ receptor is a suitable marker for targeting with a CAR expressing immune cell, in a range of cancers.

Accordingly, in a first aspect, the present invention provides a chimeric antigen receptor (CAR) which includes an antigen-recognition domain and a signalling domain, wherein the antigen-recognition domain recognises a dysfunctional P2X$_7$ receptor.

Chimeric antigen receptors are artificially constructed proteins that upon expression on the surface of a cell can induce an antigen-specific cellular response. A CAR includes at least two domains; the first domain being an antigen-recognition domain that specifically recognises an antigen, or more specifically an epitope portion, or portions, of an antigen; and the second domain being a signalling domain that is capable of inducing, or participating in the induction, of an intracellular signalling pathway.

The combination of these two domains determines the antigen specificity of the CAR and the ability of the CAR to induce a desired cellular response, the latter of which is also dependent on the host cell of the CAR. For example, the activation of a CAR expressed in a T-helper cell and having a signalling domain comprising a CD3 activation domain, may, once activated by encountering its cognate antigen, induce the CD4+T-helper cell to secrete a range of cytokines. In a further example, the same CAR when expressed in a CD8+ cytotoxic T cell, once activated by a cell expressing the cognate antigen, may induce the release of cytotoxins that ultimately lead to the induction of apoptosis of the antigen-expressing cell.

In addition to the antigen-recognition domain and the signalling domain a CAR may further include additional components, or portions. For example, the CAR may include a transmembrane domain which may comprise a portion of, or may be associated with, the signalling domain of the CAR. The transmembrane domain is typically one or more hydrophobic helices, which spans the lipid bilayer of a cell and embeds the CAR within the cell membrane. The transmembrane domain of the CAR can be one determinant in the expression pattern of the CAR when associated with a cell. For example, using a transmembrane domain associated with a CD3 co-receptor can permit expression of the CAR in naïve T cells, whilst use of a transmembrane domain from a CD4 co-receptor may direct expression of a CAR in T-helper cells but not cytotoxic T cells.

A further component or portion of a CAR may be a linker domain. The linker domain (also known as the spacer or hinge domain) may span from the extracellular side of the transmembrane domain to the antigen-recognition domain, thereby linking the antigen-recognition domain to the transmembrane domain. Whilst in some cases a linker domain is not required for a functional CAR (i.e. the antigen-recognition domain can be connected directly to the transmembrane domain) in some circumstances the use of a linker domain allows for greater efficacy of the CAR. The linker domain can have a variety of functions including allowing flexibility of the CAR to permit the necessary orientation of the antigen-recognition domain of the CAR for binding to an antigen. Consequently, the linker domain can be any amino acid sequence that performs this function. One non-limiting example of a linker domain is a domain having amino acid sequence homology to the hinge region of an IgG antibody, such as the IgG1 hinge region. Alternative examples include amino acid sequences having sequence homology to the $CH_2CH_3$ region of an antibody or portions of the CD3 co-receptor complex, the CD4 co-receptor or the CD8 co-receptor.

The P2X$_7$ receptor (purinergic receptor P2X, ligand-gated ion channel, 7) is an ATP-gated ion channel that is expressed in a number of species including humans. The receptor is encoded by a gene, the official symbol of which is represented by P2RX7. The gene has also been referred to as P2X purinoceptor 7, ATP receptor, P2Z receptor, P2X7 receptor, and purinergic receptor P2X7 variant A. For the purposes of the present disclosure, the gene and encoded receptor will be referred to herein as P2X7 and P2X$_7$, respectively.

The mRNA, coding (cDNA), and amino acid sequences of the human P2X7 gene are set out in SEQ ID NOs: 1 to 3, respectively. The mRNA and amino acid sequences of the human P2X7 gene are also represented by GenBank Accession Numbers NM_002562.5 and NP_002553.3, respectively. The P2X7 gene is conserved in chimpanzee, Rhesus monkey, dog, cow, mouse, rat, pig, chicken, zebrafish, and frog. Further details of the P2X7 gene in human and other species may be accessed from the GenBank database at the National Centre for Biotechnology Information (NCBI) (www.ncbi.nlm.nih.gov). For example, the Gene ID number for human P2X7 is 5027, for chimpanzee is 452318, for monkey is 699455, for dog is 448778, for cow is 286814, for mouse is 18439, for zebrafish is 387298, and for frog is 398286. Furthermore, at least 73 organisms have orthologs with the human P2X7 gene.

Further details regarding the P2X7 gene in human and other species can also be found at the UniGene portal of the NCBI (for example see UniGene Hs. 729169 for human P2X$_7$-http://www.ncbi.nlm.nih.gov/UniGene/
clust.cgi?UGID=4540770&TAXID=9606&SEARCH).
Alternatively, details of the nucleotide and amino acid sequences for the P2X7 gene can be accessed from the UniProt database (www.uniprot.org) wherein the UniProt ID for the human P2X7 gene is Q99572. The contents of the GenBank and UniProt records are incorporated herein by reference.

The P2X$_7$ receptor is formed from three protein subunits (monomers), wherein in the native receptor in humans at least one of the monomers has an amino acid sequence set forth in SEQ ID NO: 3. It is to be understood that a "P2X$_7$ receptor" as referred to herein also includes naturally occurring variations of the receptor including splice variants, naturally occurring truncated forms and allelic variants of the receptor. A P2X$_7$ receptor may also include subunits that have a modified amino acid sequence, for example those including truncations, amino acid deletions or modifications of the amino acid set forth in SEQ ID NO: 3.

A "variant" of the P2X7 gene or encoded protein may exhibit a nucleic acid or an amino acid sequence, respectively, that is at least 80% identical, at least 90% identical, at least 95% identical, at least 98% identical, at least 99% identical, or at least 99.9% identical to a native P2X$_7$ receptor, for example.

The P2X$_7$ receptor is activated by the binding of ATP to the ATP-binding site of the receptor. This leads to the rapid opening (within milliseconds) of a channel that selectively allows for movement of small cations across the membrane. After a short period of time (within seconds) a large pore is formed in the membrane of a cell that allows for permeation of the cell membrane by molecules up to 900 Da in size. This pore formation ultimately leads to depolarization of the cell and in many cases cytotoxicity and cell death. This role leads to a belief that the P2X$_7$ receptor is involved in apoptosis in a variety of cell types.

Like other molecules involved in apoptosis, such a Bcl2 and Bax, a decrease or loss in function of the P2X$_7$ receptor can lead to a cell that is comparatively resistant to induced apoptosis. In many cases this resistance to apoptosis is critical in the transition of a normal 'healthy' cell to a mutated pre-cancerous or cancerous cell. Consequently, the ability to target cells that have a decreased function, or a loss of function, of the P2X$_7$ receptor provides a promising target for cancer therapy.

Accordingly, in the first aspect of the invention the CAR recognises a dysfunctional P2X$_7$ receptor. As used throughout the specification the term "dysfunctional" with reference to the P2X$_7$ receptor includes a decrease in function of the receptor with respect to its comparative function in a normal non-tumour cell. In some embodiments, the function of P2X$_7$ receptor may be decreased by at least 1%, 5%, 10%, 20%, 30%, 40%, 50%, 60%, 70%, 80%, 90% or greater than 99%. In some embodiments, the term "dysfunctional" may include a P2X$_7$ receptor that is non-functional. That is to say that the P2X$_7$ receptor is unable to be induced to permit permeability of cations and other molecules across the cell membrane.

Any change in the wild-type or native form of the P2X$_7$ receptor that leads to a dysfunctional receptor is encompassed herein. For example, the dysfunctional receptor may be the result of a mutation or alteration in one or more amino acids of the receptor that are associated with ATP binding to the receptor. In effect, the P2X$_7$ receptor is dysfunctional as it has a reduced capacity to, or cannot, bind ATP at the ATP-binding site. In this instance, the antigen-recognition domain of the chimeric antigen receptor will recognise an epitope of the dysfunctional P2X$_7$ receptor associated with the ATP-binding site. Consequently, in some embodiments of the first aspect of the invention, the antigen-recognition domain of the chimeric antigen receptor recognises an epitope of the dysfunctional P2X$_7$ receptor associated with the ATP-binding site. In some embodiments, the dysfunctional P2X$_7$ receptor has a reduced capacity to bind ATP compared to an ATP-binding capacity of a wild-type (functional) P2X$_7$ receptor. In some embodiments the dysfunctional P2X$_7$ receptor cannot bind ATP.

An alteration in one or more amino acids of the P2X$_7$ receptor may include a conformational change in one or more amino acids of the receptor. Therefore, in some embodiments of the first aspect of the invention the chimeric antigen receptor binds to a dysfunctional P2X$_7$ receptor having a conformational change that renders the receptor dysfunctional. Specifically, this conformational change may be a change in one or more amino acids of the P2X$_7$ receptor from a trans-conformation to a cis-conformation. In some embodiments, a proline at position 210 of the P2X$_7$ receptor changes from a trans-conformation to a cis-conformation. In this instance, the antigen-recognition domain of the CAR may recognise an epitope that includes proline at amino acid position 210 of the P2X$_7$ receptor. In some embodiments of the first aspect of the present invention, the antigen-recognition domain recognises an epitope that includes one or more amino acids spanning from glycine at amino acid position 200 to cysteine at amino acid position 216 (inclusive) of the dysfunctional P2X$_7$ receptor. In some embodiments of the first aspect of the present invention, the antigen-recognition domain recognises an epitope that includes the proline at position 210 of the dysfunctional P2X$_7$ receptor, and one or more of the amino acid residues spanning from glycine at amino acid position 200 to cysteine at amino acid position 216 (inclusive) of the dysfunctional P2X$_7$ receptor.

Whilst not wanting to be bound by theory, as a result of the conformational change of the proline at position 210 of the P2X$_7$ receptor, the three-dimensional structure of the receptor may be altered. This alteration in the three-dimensional structure may allow the antigen-recognition domain of the CAR to bind to amino acids, or epitopes, previously inaccessible in the native three-dimensional structure of the P2X$_7$ receptor. Therefore, in some embodiments the CAR recognises one or more epitopes of the P2X$_7$ receptor exposed to the antigen-recognition domain as a result of a trans- to cis-conformational change of the proline at position 210 of SEQ ID NO: 3. These epitopes may include one or more of the amino acids at position 200 to 210, or positions 297 to 306, inclusive, of the P2X$_7$ receptor. Accordingly, in some embodiments of the first aspect of the present invention, the antigen-recognition domain recognises an epitope that includes one or more of the amino acids at positions 200 to 210 and/or 297 to 306 of the P2X$_7$ receptor.

As used throughout the specification the term "recognises" relates to the ability of the antigen-recognition domain to associate with a dysfunctional P2X$_7$ receptor, a portion thereof, or an epitope thereof. In some embodiments, the antigen-recognition domain may directly bind to the dysfunctional P2X$_7$ receptor, or an epitope thereof. In other embodiments, the antigen-recognition domain may bind to a processed form of the dysfunctional P2X$_7$ receptor. As used in this context the term "processed form" relates to forms of the P2X$_7$ receptor which have been truncated or digested as a result of intracellular processing. Consequently, the recognition of the "processed form" of the dysfunctional P2X$_7$ receptor may be as a result of being presented in association with a major histocompatibility complex (MHC).

The antigen-recognition domain can be any suitable domain that can recognise a dysfunctional P2X$_7$ receptor, or epitope thereof. As used throughout the specification the term "antigen-recognition domain" refers to the portion of the CAR that provides the specificity of the CAR for the dysfunctional P2X$_7$ receptor. The antigen-recognition domain may be all of, or may merely be part of, the extracellular region of the CAR. Suitable antigen-recognition domains, include, but are not limited to, polypeptides having sequence homology to the antigen-binding site of an antibody, or fragment thereof, that bind to a dysfunctional P2X$_7$ receptor. Therefore, in some embodiments of the first aspect of the invention, the antigen-recognition domain includes an amino acid sequence having homology to an antibody, or a fragment thereof, that binds to a dysfunctional P2X$_7$ receptor. In some embodiments, a portion of the antigen-recognition domain includes an amino acid sequence having homology to an antibody, or a fragment thereof, that binds to the dysfunctional P2X$_7$ receptor. The source homologous antibody sequence can be any suitable sequence of an antibody that has an affinity for the P2X$_7$ receptor. For example the sequence can share sequence homology with an antibody originating from one or more of the following species; human, non-human primate, mouse, rat, rabbit, sheep, goat, ferret, canine, chicken, feline, guinea pig, hamster, horse, cow, or pig. The antigen-recognition domain may share sequence homology with the sequence of a monoclonal antibody produced from a hybridoma cell line. When the originating species of the homologous antibody sequence is not human, the antibody is preferably a humanised antibody. The homologous antibody sequence may also be from a non-mammalian animal species such as a cartilaginous fish (e.g. shark IgNAR antibodies—see WO2012/073048). Alternatively, the antigen binding domain may include a modified protein scaffolds that provide functionality similar to shark antibodies, such as i-bodies which have binding moieties based on shark IgNAR antibodies (see WO2005/118629). Additionally, the antigen-recognition domain could be, could be derived from, or could share sequence homology with any other suitable binding molecule or peptide that can selectively interact with a dysfunctional $P2X_7$ receptor with an affinity sufficient to activate the CAR signalling domain. Methods are known in the art for the identification of antigen-binding proteins such as, inter alia, panning phage display libraries, protein affinity chromatography, co-immunoprecipitation and yeast two-hybrid systems (see Srinivasa Rao, V. et al. Int J Proteomics, 2014; article ID 147648).

In some embodiments the antigen-recognition domain of the CAR includes amino acid sequence homology to the amino acid sequence of a fragment-antigen binding (Fab) portion of an antibody that binds to a dysfunctional $P2X_7$ receptor. As will be understood in the art, a Fab portion of an antibody in composed of one constant region and one variable region of each of the heavy and light chains of an antibody. The Fab is the antigen determinant region of the antibody and can be generated by enzymatically cleaving the Fc region from an antibody.

In some embodiments of the first aspect of the invention, the antigen-recognition domain includes amino acid sequence homology to the amino acid sequence of a single-chain variable fragment (scFv) that binds to a dysfunctional $P2X_7$ receptor. As would be understood in the art, a scFv is a fusion protein comprising two portions that may share homology with, or may be identical to, the variable-heavy (VH) and variable-light (VL) chains of an antibody, with the two portions connected together with a linker peptide. For example, the scFv may include VH and VL amino acid sequences that are derived from an antibody that recognises a dysfunctional $P2X_7$ receptor. In this context it will be appreciated that the term "derived from" is not a reference to the source of the polypeptides per se, but rather refers to the derivation of the amino acid sequence that constitute a portion of the antigen-binding region. Consequently, the term "derived from" includes synthetically, artificially or otherwise created polypeptides that share sequence identity to an antibody that binds to the dysfunctional $P2X_7$ receptor.

In some embodiments of the first aspect of the invention, the antigen-recognition domain includes amino acid sequence homology to the amino acid sequence of a multi-valent scFv that binds to a dysfunctional $P2X_7$ receptor. In some embodiments, the multivalent scFv is a di-valent or tri-valent scFv.

In some embodiments of the first aspect of the invention, the antigen-recognition domain has the amino acid sequence of a single-antibody domain (sdAb) that binds to a dysfunctional $P2X_7$ receptor.

In some embodiments, the antigen-recognition domain includes the amino acid sequence set forth in SEQ ID NO: 10, SEQ ID NO: 32, SEQ ID NO: 33 or SEQ ID NO: 34 or a functional variant thereof.

In some embodiments, the antigen-recognition domain includes a binding peptide that includes amino acid sequence homology with one or more CDR regions of an antibody that binds to a dysfunctional $P2X_7$ receptor. In some embodiments, the biding peptide includes one or more regions having sequence homology with the CDR1, 2 and 3 domains of the $V_H$ and/or $V_L$ chain of an antibody that binds to a dysfunctional $P2X_7$ receptor. In some embodiments, the antigen recognition domain includes one or more sequences which are at least 50%, 60%, 70%, 80%, 90% or 94% identical to any one of the CDR regions spanning positions 30 to 35, 50 to 67 or 98 to 108 of the sequences set forth in SEQ ID NOS: 10, 32, 33 or 34. In some embodiments, the antigen recognition domain includes one or more of the sequences spanning positions 30 to 35, 50 to 67 or 98 to 108 of the sequences set forth in SEQ ID NOS: 10, 32, 33 or 34. The sequences interspacing the CDR regions of the antigen binding peptides set forth in SEQ ID NOS: 10, 32, 33 or 34 can be any suitable sequence that permits the appropriate formation and conformation of the CDR regions. In some embodiments, the antigen recognition domain includes a sequence 50%, 60%, 70%, 80% or 90%, 95% or 99% identical to one of the sequences set forth in SEQ ID NOS: 10, 32, 33 or 34.

Antibodies directed against dysfunctional $P2X_7$ receptors, from which suitable amino acid sequences may be derived, and methods for producing such antibodies, have been described in the art (for example WO2001/020155, WO2003/020762, WO2008/043145, WO2008/043146, WO2009/033233, WO2011/020155 and WO2011/075789). Methods for generating polyclonal and monoclonal antibodies for specific epitopes (such as those set forth previously) would be known to a person skilled in the art. By way of summary, a desired epitope (such as a segment of the dysfunctional $P2X_7$ receptor including the proline at position 210) is injected into a suitable host animal in the presence of an appropriate immunogenic carrier protein and an adjuvant. Serum is then collected from the immunized animal and the antibody can be isolated based on its antibody class or its antigen specificity. Following assessment of the suitability and specificity of the purified antibody, the antibody can be further processed to isolate antigen-binding fragments, or sequenced to identify the relevant VH and VL domains. Suitable epitopes for the production of antibodies directed against the dysfunctional $P2X_7$ receptor are known in the art (see WO2008/043146, WO2010/000041 and WO2009/033233 as examples).

The signalling domain of the CAR can be any suitable domain that is capable of inducing, or participating in the induction of, an intracellular signalling cascade upon activation of the CAR as a result of recognition of an antigen by the antigen-recognition domain of the CAR. The signalling domain of a CAR will be specifically chosen depending on the cellular outcome desired following activation of the CAR. Whilst there are many possible signalling domains, when used in immunotherapy and cancer therapy the signalling domains can be grouped into two general categories based on the receptor from which they are derived, namely activation receptors and co-stimulatory receptors (see further details below). Therefore, in some embodiments of the first aspect of the invention, the signalling domain includes a portion derived from an activation receptor. In some embodiments, the signalling domain includes a portion derived from a co-stimulatory receptor As used throughout the specification the term "portion", when used with respect to an activation receptor or co-stimulatory receptor, relates to any segment of the receptor that includes a sequence responsible for, or involved in, the initiation/induction of an intracellular signalling cascade following interaction of the receptor with its cognate antigen or ligand. An example of the initiation/induction of an intracellular signalling cascade for the T cell receptor (TCR) via CD3 is outlined below.

Whilst not wishing to be bound by theory, the extracellular portion of the TCR largely comprises heterodimers of either the clonotypic TCRα and TCRβ chains (the TCRα/β receptor) or the TCRγ and TCRδ chains (the TCRγδ receptor). These TCR heterodimers generally lack inherent signalling transduction capabilities and therefore they are non-covalently associated with multiple signal transducing subunits of CD3 (primarily CD3-zeta, -gamma, -delta, and -epsilon). Each of the gamma, delta, and epsilon chains of CD3 has an intracellular (cytoplasmic) portion that includes a single Immune-receptor-Tyrosine-based-Activation-Motif (ITAM), whilst the CD3-zeta chain includes three tandem ITAMs. Upon engagement of the TCR by its cognate antigen in the presence of MHC, and the association of a requisite co-receptor such as CD4 or CD8, signalling is initiated which results in a tyrosine kinase (namely Lck) phosphorylating the two tyrosine residues within the intracellular ITAM(s) of the CD3 chains. Subsequently, a second tyrosine kinase (ZAP-70—itself activated by Lck phosphorylation) is recruited to biphosphorylate the ITAMs. As a result, several downstream target proteins are activated which eventually leads to intracellular conformational changes, calcium mobilisation, and actin cytoskeleton re-arrangement that when combined ultimately lead to activation of transcription factors and induction of a T cell immune response.

As used throughout the specification the term "activation receptor" relates to receptors, or co-receptors that form a component of, or are involved in the formation of, the T cell receptor (TCR) complex, or receptors involved in the specific activation of immune cells as a result of recognition of an antigenic or other immunogenic stimuli.

Non-limiting examples of such activation receptors include components of the T cell receptor-CD3 complex (CD3-zeta, -gamma, -delta, and -epsilon), the CD4 co-receptor, the CD8 co-receptor, FC receptors or Natural Killer (NK) cell associated activation receptors such a LY-49 (KLRA1), natural cytotoxicity receptors (NCR, preferably NKp46, NKp44, NKp30 or NKG2 or the CD94/NKG2 heterodimer). Consequently, in some embodiments of the first aspect of the present invention, the signalling domain includes a portion derived from any one or more of a member of the CD3 co-receptor complex (preferably the CD3-ζ chain or a portion thereof), the CD4 co-receptor, the CD8 co-receptor, a Fc Receptor (FcR) (preferably the FcεRI or FcγRI) or NK associated receptors such a LY-49.

The specific intracellular signal transduction portion of each of the CD3 chains are known in the art. By way of example, the intracellular cytoplasmic region of the CD3ζ chain spans from amino acid 52 to amino acid 164 of the sequence set forth in SEQ ID NO: 4, with the three ITAM regions spanning amino acids 61 to 89, 100 to 128 and 131 to 159 of SEQ ID NO: 4. Furthermore, the intracellular portion of the CD3ε chain spans amino acids 153 to 207 of the sequence set forth in SEQ ID NO: 5, with the single ITAM region spanning amino acids 178 to 205 of SEQ ID NO: 5. The intracellular portion of CD3γ chain spans amino acids 138 to 182 of the sequence set forth in SEQ ID NO: 6 with the single ITAM region spanning amino acids amino acids 149 to 177 of SEQ ID NO: 6. The intracellular portion of CD3δ spans amino acids 127 to 171 of the sequence set forth in SEQ ID NO: 7 with the single ITAM region spanning amino acids 138 to 166 of SEQ ID NO: 7.

In some embodiments of the first aspect of the present invention, the signalling domain includes a portion derived from any one of CD3 (preferably the CD3-ζ chain or a portion thereof) or an FC receptor (preferably the FcεRI or FcγRI). In some embodiments, the portion of the CD3-ζ co-receptor complex includes the amino acid sequence set forth in SEQ ID NO: 22, or a functional variant thereof.

The intracellular portions of the FC receptors are known in the art. For example, the intracellular portions of the FcεR1 span amino acids 1 to 59, 118 to 130 and 201 to 244 of the sequence set forth in SEQ ID NO: 8. Furthermore, the intracellular portion of FcγRI spans the amino acids 314 to 374 of the sequence set forth in SEQ ID NO: 9.

Various combinations of portions of activation receptors can be utilized to form the transmembrane (TM) and intracellular (IC) portions of the CAR for example the CD3 TM and CD3 IC (Landmeier S. et al. Cancer Res. 2007; 67:8335-43; Guest R D. et al., J Immunother. 2005, 28:203-11; Hombach A A. et al. J Immunol. 2007; 178: 4650-7), the CD4 TM and CD3 IC (James S E. et al. J Immunol. 2008; 180:7028-38), the CD8 TM and CD3ζ IC (Patel S D. et al. Gene Ther. 1999; 6: 412-9), and the FcεRIγ™ and the FcεRIγ IC (Haynes N M. et al. J Immunol. 2001; 166: 182-7; Annenkov A E. et al. J Immunol. 1998; 161: 6604-13).

As used throughout the specification the term "co-stimulatory receptor" relates to receptors or co-receptors that assist in the activation of an immune cell upon antigen specific inducement of an activation receptor. As will be understood, co-stimulatory receptors do not require the presence of antigen and are not antigen specific, but are typically one of two signals, the other being an activation signal, which is required for the induction of an immune cellular response. In the context of an immune response a co-stimulation receptor is typically activated by the presence of its expressed ligand on the surface of an antigen-presenting cell (APC) such as a dendritic cell or macrophage. With specific regard to T cells, co-stimulation is necessary to lead to cellular activation, proliferation, differentiation and survival (all of which are generally referred to under the umbrella of T cell activation), whilst presentation of an antigen to a T cell in the absence of co-stimulation can lead to anergy, clonal deletion and/or the development of antigen specific tolerance. Importantly, co-stimulatory molecules can inform the T cell response to a simultaneously encountered antigen. Generally, an antigen encountered in the context of a 'positive' co-stimulatory molecule will lead to activation of the T cell and a cellular immune response aimed at eliminating cells expressing that antigen. Whilst an antigen encountered in the context of a 'negative' co-receptor will lead to an induced state of tolerance to the co-encountered antigen.

Non-limiting examples of T cell co-stimulatory receptors include CD27, CD28, CD30, CD40, DAP10, OX40, 4-1BB (CD137), ICOS. Specifically, CD27, CD28, CD30, CD40, DAP10, OX40, 4-1 BB (CD137), and ICOS all represent 'positive' co-stimulatory molecules that enhance activation of a T cell response. Accordingly, in some embodiments of the first aspect of the present invention, the signalling domain includes a portion derived from any one or more of CD27, CD28, CD30, CD40, DAP10, OX40, 4-1BB (CD137) and ICOS.

In some embodiments of the first aspect of the present invention, the signalling domain includes a portion derived from the CD28, OX40 or 4-1BB co-stimulatory receptors. In some embodiments, the signalling domain includes a portion of the CD28 co-stimulatory receptor. In some embodiments, the signalling domain includes a portion of the OX40 co-stimulatory receptor. In some embodiments, the portion of the OX40 co-stimulatory receptor includes the amino acid sequence set forth in SEQ ID NO: 20, or a functional variant thereof.

Various combinations of portions of co-stimulatory receptors can be utilized to form the transmembrane (TM) and intracellular (IC) portions of the CAR. For example the CD8 TM and DAP10 IC or CD8 TM and 4-1 BB IC (Marin V. et al. Exp Hematol. 2007; 35:1388-97), the CD28 TM and the CD28 IC (Wilkie S. et al. J Immunol. 2008; 180: 4901-9; Maher J. et al. Nat Biotechnol. 2002; 20: 70-5), and the CD8 TM and the CD28 IC (Marin V. et al. Exp Hematol. 2007; 35: 1388-97).

Sequence information for the above-referenced activation and co-stimulatory receptors is readily accessible in a variety of databases. For example, embodiments of human amino acid, gene and mRNA sequences for these receptors is provided in Table 2.

TABLE 2

Summary of Activation and Co-stimulation Receptor Sequence Information

| Receptor Name | Uniprot Ref No. | NCBI Gene ID No. | GeneBank mRNA Ref No. |
| --- | --- | --- | --- |
| CD3-zeta | P20963 | 919 | GI:166362721 |
| CD3-gamma | P09693 | 917 | GI:166362738 |
| CD3-delta | P04234 | 915 | GI:98985799 |
| CD3-epsilon | P07766 | 916 | GI:166362733 |
| CD4 | P0173 | 920 | GI:303522473 |
| CD8 alpha | P01732 | 925 | GI:225007534 |
| CD8 beta | P01966 | 926 | GI:296010927 |
| FcγRI | P12314 | 2209 | GI:31331 |
| FcεR1 | Q01362 | 2206 | GI:219881 |
| Ly-49 (KLRAI) | Q7Z556 | 10748 | GI:33114184 |
| NKp46 | O76036 | 9437 | GI:3647268 |
| NKp44 | O95944 | 9436 | GI:4493701 |
| NKp30 | O14931 | 259197 | GI:5823969 |
| CD94 | Q13241 | 3824 | GI:1098616 |
| CD27 | P26842 | 939 | GI:180084 |
| CD28 | P10747 | 940 | GI:338444 |
| CD30 | P28908 | 943 | GI:180095 |
| CD40 | P25942 | 958 | GI:29850 |
| DAP10 | Q9UBK5 | 10870 | GI:5738198 |
| OX40 | P43489 | 7293 | GI:472957 |
| 4-1BB (CD137) | Q07011 | 3604 | GI:571320 |
| ICOS | Q9Y6W8 | 29851 | GI:9968295 |
| CTLA-4 | P16410 | 1493 | GI:291928 |
| PD-1 | Q15116 | 5133 | GI:2149002 |

Whilst Table 2 is provided with reference to human activation and co-stimulatory receptors, it would be understood by a person skilled in the art that homologous and orthologous versions of each receptor are present in the majority of mammalian and vertebrate species. Therefore, the above-referenced sequences are only provided as non-limiting examples of receptor sequences that may be included in a CAR of the first aspect of the present invention and homologous and orthologous sequences from any desired species may be used to generate a CAR that is suitable for the given species.

In some embodiments of the first aspect of the invention, the signalling domain includes a portion derived from an activation receptor and a portion derived from a co-stimulatory receptor. Whilst not wishing to be bound by theory, in this context the recognition of an antigen by the antigen-recognition domain of the CAR will simultaneously induce both an intracellular activation signal and an intracellular co-stimulatory signal. Consequently, this will simulate the presentation of an antigen by an APC expressing co-stimulatory ligand. Alternatively, the CAR could have a signalling domain that includes a portion derived from either an activation receptor or a co-stimulatory receptor. In this alternative form, the CAR will only induce either an activating intracellular signalling cascade or a co-stimulatory intracellular signalling cascade.

In some embodiments of the first aspect of the invention, the CAR will have a signalling domain that includes a portion derived from a single activation receptor and portions derived from multiple co-stimulatory receptors. In some embodiments, the CAR will have a signalling domain that includes portions derived from multiple activation receptors and a portion derived from a single co-stimulatory receptor. In some embodiments, the CAR will have a signalling domain that includes portions derived from multiple activation receptors and portions derived from multiple co-stimulatory receptors. In some embodiments, the CAR will have a signalling domain that includes a portion derived from a single activation receptor and portions derived from two co-stimulatory receptors. In some embodiments, the CAR will have a signalling domain that includes a portion derived from a single activation receptor and portions derived from three co-stimulatory receptors. In some embodiments, the CAR will have a signalling domain that includes portions derived from two activation receptors, and a portion derived from one co-stimulatory receptor. In some embodiments, the CAR will have a signalling domain that includes portions derived from two activation receptors and portions derived from two co-stimulatory receptors. As will be understood there are further variations of the number of activation receptors and co-stimulatory receptors from which the signalling domain can be derived from, and the above examples are not considered to be limiting on the possible combinations included herein.

In some embodiments of the first aspect of the invention, the chimeric antigen receptor includes the amino acid sequence set forth in SEQ ID NO: 26, SEQ ID NO: 27, SEQ ID NO: 52, SEQ ID NO: 53 or SEQ ID NO: 54, or a functional variant of SEQ ID NO: 26, SEQ ID NO: 27, SEQ ID NO: 52, SEQ ID NO: 53 or SEQ ID NO: 54. In some embodiments, the functional variant includes an amino acid sequence which is at least 80% identical to SEQ ID NO: 26, SEQ ID NO: 27, SEQ ID NO: 52, SEQ ID NO: 53 or SEQ ID NO: 54.

As indicated above, the present invention includes a functional variant of any one of SEQ ID NO: 10, SEQ ID NO: 18, SEQ ID NO: 20, SEQ ID NO: 22, SEQ ID NO: 26, SEQ ID NO: 27, SEQ ID NO: 32, SEQ ID NO: 33, SEQ ID NO: 34, SEQ ID NO: 52, SEQ ID NO: 53 or SEQ ID NO: 54. In the context of the present invention, a "functional variant" may include any amino acid sequence provided it maintains the function of any one of SEQ ID NO: 10, SEQ ID NO: 18, SEQ ID NO: 20, SEQ ID NO: 22, SEQ ID NO: 26, SEQ ID NO: 27, SEQ ID NO: 32, SEQ ID NO: 33, SEQ ID NO: 34, SEQ ID NO: 52, SEQ ID NO: 53 or SEQ ID NO: 54.

As such, the functional variant may, for example, have one or more amino acid insertions, deletions or substitutions relative to one of SEQ ID NO: 10, SEQ ID NO: 18, SEQ ID NO: 20, SEQ ID NO: 22, SEQ ID NO: 26, SEQ ID NO: 27, SEQ ID NO: 32, SEQ ID NO: 33, SEQ ID NO: 34, SEQ ID NO: 52, SEQ ID NO: 53 or SEQ ID NO: 54; a mutant form or allelic variant of one of SEQ ID NO: 10, SEQ ID NO: 18, SEQ ID NO: 20, SEQ ID NO: 22, SEQ ID NO: 26, SEQ ID NO: 27, SEQ ID NO: 32, SEQ ID NO: 33, SEQ ID NO: 34, SEQ ID NO: 52, SEQ ID NO: 53 or SEQ ID NO: 54; an ortholog of one of SEQ ID NO: 10, SEQ ID NO: 18, SEQ ID NO: 20, SEQ ID NO: 22, SEQ ID NO: 26, SEQ ID NO: 27, SEQ ID NO: 32, SEQ ID NO: 33, SEQ ID NO: 34, SEQ ID NO: 52, SEQ ID NO: 53 or SEQ ID NO: 54; a homeologue of one of SEQ ID NO: 10, SEQ ID NO: 18, SEQ ID NO: 20, SEQ ID NO: 22, SEQ ID NO: 26, SEQ ID NO: 27, SEQ ID NO: 32, SEQ ID NO: 33, SEQ ID NO: 34, SEQ ID NO: 52, SEQ ID NO: 53 or SEQ ID NO: 54; an analog of one of SEQ ID NO: 10, SEQ ID NO: 18, SEQ ID NO: 20, SEQ ID NO: 22, SEQ ID NO: 26, SEQ ID NO: 27, SEQ ID NO: 32, SEQ ID NO: 33, SEQ ID NO: 34, SEQ ID NO: 52, SEQ ID NO: 53 or SEQ ID NO: 54; and the like, provided the functional variant maintains the function of any one of SEQ ID NO: 10, SEQ ID NO: 18, SEQ ID NO: 20, SEQ ID NO: 22, SEQ ID NO: 26, SEQ ID NO: 27, SEQ ID NO: 32, SEQ ID NO: 33, SEQ ID NO: 34, SEQ ID NO: 52, SEQ ID NO: 53 or SEQ ID NO: 54.

For example with respect to SEQ ID NO: 26, SEQ ID NO: 27, SEQ ID NO: 52, SEQ ID NO: 53 or SEQ ID NO: 54 the function of a chimeric antigen receptor comprising SEQ ID NO: 26, SEQ ID NO: 27, SEQ ID NO: 52, SEQ ID NO: 53 or SEQ ID NO: 54 is to recognise a dysfunctional P2X$_7$ receptor without significant recognition of the functional P2X$_7$ receptor, and induce an intracellular signal which results in the activation of a T cell expressing the CAR. As would be understood by a person skilled in the art, variation to portions of the amino acid sequence of the chimeric antigen receptor set forth in SEQ ID NO: 26, SEQ ID NO: 27, SEQ ID NO: 52, SEQ ID NO: 53 or SEQ ID NO: 54 may be made without significant alteration of the recognition of the dysfunctional P2X$_7$ receptor and/or activation of a T cell expressing the CAR. Such variations may include, but are not limited to, variations in the hinge region of the chimeric antigen receptor, variations in the transmembrane domain, and variations in the portions of the activation receptors and/or co-stimulatory receptors that comprise the intracellular domain of the chimeric antigen receptor.

As indicated above, the functional variant may comprise individual amino acid substitutions, deletions or insertions relative to one of SEQ ID NO: 10, SEQ ID NO: 18, SEQ ID NO: 20, SEQ ID NO: 22, SEQ ID NO: 26, SEQ ID NO: 27, SEQ ID NO: 32, SEQ ID NO: 33, SEQ ID NO: 34, SEQ ID NO: 52, SEQ ID NO: 53 or SEQ ID NO: 54. For example, a person skilled in the art will recognise that any amino acid can be substituted with a chemically (functionally) similar amino acid and retain function of the polypeptide. Such conservative amino acid substitutions are well known in the art. The following groups in Table 3 each contain amino acids that are conservative substitutions for one another.

TABLE 3

Exemplary amino acid conservative substitutions

| Original Residue | Exemplary Substitutions |
| --- | --- |
| Ala (A) | Val (V), Leu (L), Ile (I), Gly (G) |
| Arg (R) | Lys (K) |
| Asn (N) | Gln (Q), His (H) |
| Asp (D) | Glu (E) |
| Cys (C) | Ser (S) |
| Gln (Q) | Asn (N), His (H) |
| Glu (E) | Asp (D) |
| Gly (G) | Pro (P), Ala (A) |
| His (H) | Asn (N), Gln (Q) |
| Ile (I) | Leu (L), Val (V), Ala (A) |
| Leu (L) | Ile (I), Val (V), Met (M), Ala (A), Phe (F) |
| Lys (K) | Arg (R) |
| Met (M) | Leu (L), Phe (F) |
| Phe (F) | Leu (L), Val (V), Alal (A) |
| Pro (P) | Gly (G) |
| Ser (S) | Thr (T) |
| Thr (T) | Ser (S) |
| Trp (W) | Tyr (Y) |

TABLE 3-continued

Exemplary amino acid conservative substitutions

| Original Residue | Exemplary Substitutions |
| --- | --- |
| Tyr (Y) | Trp (W), Phe (F) |
| Val (V) | Ile (I), Leu (L), Met (M), Phe (F), Ala (A) |

Furthermore, if desired, unnatural amino acids or chemical amino acid analogues can be introduced as a substitution or addition into a polypeptide encompassed herein. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

As set out above, a functional variant of any one of SEQ ID NO: 10, SEQ ID NO: 18, SEQ ID NO: 20, SEQ ID NO: 22, SEQ ID NO: 26, SEQ ID NO: 27, SEQ ID NO: 32, SEQ ID NO: 33, SEQ ID NO: 34, SEQ ID NO: 52, SEQ ID NO: 53 or SEQ ID NO: 54 may comprise an amino acid sequence which is at least 80% identical to any one of SEQ ID NO: 10, SEQ ID NO: 18, SEQ ID NO: 20, SEQ ID NO: 22, SEQ ID NO: 26, SEQ ID NO: 27, SEQ ID NO: 32, SEQ ID NO: 33, SEQ ID NO: 34, SEQ ID NO: 52, SEQ ID NO: 53 or SEQ ID NO: 54. In other embodiments, a functional variant may comprise at least 85% amino acid sequence identity, at least 90% amino acid sequence identity, at least 91% amino acid sequence identity, at least 92% amino acid sequence identity, at least 93% amino acid sequence identity, at least 94% amino acid sequence identity, at least 95% amino acid sequence identity, at least 96% amino acid sequence identity, at least 97% amino acid sequence identity, at least 98% amino acid sequence identity, at least 99% amino acid sequence identity, or at least 99.1%, 99.2%, 99.3%, 99.4%, 99.5%, 99.6%, 99.7%, 99.8%, or 99.9% amino acid sequence identity to any one of SEQ ID NO: 10, SEQ ID NO: 18, SEQ ID NO: 20, SEQ ID NO: 22, SEQ ID NO: 26, SEQ ID NO: 27, SEQ ID NO: 32, SEQ ID NO: 33, SEQ ID NO: 34, SEQ ID NO: 52, SEQ ID NO: 53 or SEQ ID NO: 54.

When comparing amino acid sequences, the sequences should be compared over a comparison window which is determined by the length of the polypeptide. For example, a comparison window of at least 20 amino acid residues, at least 50 amino acid residues, at least 75 amino acid residues, at least 100 amino acid residues, at least 200 amino acid residues, at least 300 amino acid residues, at least 400 amino acid residues, at least 500 amino acid residues, at least 600 amino acid residues, or over the full length of any one of SEQ ID NO: 10, SEQ ID NO: 18, SEQ ID NO: 20, SEQ ID NO: 22, SEQ ID NO: 26, SEQ ID NO: 27, SEQ ID NO: 32, SEQ ID NO: 33, SEQ ID NO: 34, SEQ ID NO: 52, SEQ ID NO: 53 or SEQ ID NO: 54 is envisaged. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerised implementations of algorithms such as the BLAST family of programs as, for example, disclosed by Altschul et al., 1997, *Nucl. Acids Res.* 25: 3389-3402. Global alignment programs may also be used to align similar sequences of roughly equal size. Examples of global alignment programs include NEEDLE (available at www.ebi-.ac.uk/Tools/psa/emboss_needle/) which is part of the EMBOSS package (Rice P et al., 2000, *Trends Genet.*, 16: 276-277), and the GGSEARCH program (available at fasta-.bioch.virginia.edu/fasta_www2/fasta_www.cgi?rm=compare&pgm=gnw) which is part of the FASTA package (Pearson W and Lipman D, 1988, *Proc. Natl. Acad. Sci. USA*, 85: 2444-2448). Both of these programs are based on the Needleman-Wunsch algorithm which is used to find the optimum alignment (including gaps) of two sequences along their entire length. A detailed discussion of sequence analysis can also be found in Unit 19.3 of Ausubel et al ("Current Protocols in Molecular Biology" John Wiley & Sons Inc, 1994-1998, Chapter 15, 1998).

In a second aspect, the present invention provides a nucleic acid molecule including a nucleotide sequence encoding the chimeric antigen receptor according to the first aspect of the invention. In some embodiments, the nucleic acid molecule is a non-naturally occurring nucleic acid molecule.

In some embodiments of the second aspect of the invention, the nucleic acid molecule includes a nucleotide sequence which encodes the amino acid sequence set forth in SEQ ID NO: 26, SEQ ID NO: 27, SEQ ID NO: 52, SEQ ID NO: 53 or SEQ ID NO: 54, or encodes a functional variant of SEQ ID NO: 26, SEQ ID NO: 27, SEQ ID NO: 52, SEQ ID NO: 53 or SEQ ID NO: 54. In some embodiments, the functional variant includes an amino acid sequence which is at least 80% identical to SEQ ID NO: 26, SEQ ID NO: 27, SEQ ID NO: 52, SEQ ID NO: 53 or SEQ ID NO: 54.

The nucleic acid molecule may comprise any polyribonucleotide or polydeoxyribonucleotide, which may be unmodified, or modified, RNA or DNA. For example, the nucleic acid molecule may include single- and/or double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the nucleic acid molecule may comprise triple-stranded regions comprising RNA or DNA or both RNA and DNA. The nucleic acid molecule may also comprise one or more modified bases or DNA or RNA backbones modified for stability or for other reasons. A variety of modifications can be made to DNA and RNA; thus the term "nucleic acid molecule" embraces chemically, enzymatically, or metabolically modified forms.

In some embodiments of the second aspect of the invention, the nucleic acid molecule includes the nucleotide sequence set forth in SEQ ID NO: 28, SEQ ID NO: 29, SEQ ID NO: 35, SEQ ID NO: 36 or SEQ ID NO: 37.

It would be understood by a person skilled in the art that any nucleotide sequence which encodes a chimeric antigen receptor having the amino acid sequence set forth in SEQ ID NO: 26, SEQ ID NO: 27, SEQ ID NO: 35, SEQ ID NO: 36 or SEQ ID NO: 37, or a functional variant of SEQ ID NO: 26, SEQ ID NO: 27, SEQ ID NO: 35, SEQ ID NO: 36 or SEQ ID NO: 37, is contemplated by the present invention. For example, variants of SEQ ID NO: 28, SEQ ID NO: 29, SEQ ID NO: 35, SEQ ID NO: 36 or SEQ ID NO: 37 are contemplated which comprise one or more different nucleic acids to SEQ ID NO: 28, SEQ ID NO: 29, SEQ ID NO: 35, SEQ ID NO: 36 or SEQ ID NO: 37 but which still encode identical amino acid sequences. Because of the degeneracy of the genetic code, a large number of nucleic acids can encode any given protein. For instance, the codons GCA, GCC, GCG and GCU all encode the amino acid alanine. Therefore, at every position in SEQ ID NO: 28, SEQ ID NO: 29, SEQ ID NO: 35, SEQ ID NO: 36 or SEQ ID NO: 37 where an alanine is specified by a codon, the codon can be altered to any of the corresponding codons described without altering the encoded polypeptide. Accordingly, every nucleotide sequence herein which encodes a chimeric antigen receptor having the amino acid sequence set forth in SEQ ID NO: 26, SEQ ID NO: 27, SEQ ID NO: 35, SEQ ID NO: 36 or SEQ ID NO: 37, or a functional variant of SEQ ID NO: 26, SEQ ID NO: 27, SEQ ID NO: 35, SEQ ID NO: 36 or SEQ ID NO: 37 also describes every possible silent variation of the nucleotide sequence. One of skill will recognise that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleotide sequence that encodes a polypeptide is implicit in each described sequence.

In a third aspect, the present invention provides a nucleic acid construct including a nucleic acid molecule according to the second aspect of the invention. The nucleic acid construct may further comprise one or more of: an origin of replication for one or more hosts; a selectable marker gene which is active in one or more hosts; and/or one or more transcriptional control sequences.

As used herein, the term "selectable marker gene" includes any gene that confers a phenotype on a cell in which it is expressed, to facilitate the identification and/or selection of cells which are transfected or transformed with the construct.

"Selectable marker genes" include any nucleotide sequences which, when expressed by a cell transformed with the construct, confer a phenotype on the cell that facilitates the identification and/or selection of these transformed cells. A range of nucleotide sequences encoding suitable selectable markers are known in the art (for example Mortesen, R M. and Kingston R E. Curr Protoc Mol Biol, 2009; Unit 9.5). Exemplary nucleotide sequences that encode selectable markers include: Adenosine deaminase (ADA) gene; Cytosine deaminase (CDA) gene; Dihydrofolate reductase (DHFR) gene; Histidinol dehydrogenase (hisD) gene; Puromycin-N-acetyl transferase (PAC) gene; Thymidine kinase (TK) gene; Xanthine-guanine phosphoribosyltransferase (XGPRT) gene or antibiotic resistance genes such as ampicillin-resistance genes, puromycin-resistance genes, Bleomycin-resistance genes, hygromycin-resistance genes, kanamycin-resistance genes and ampicillin-resistance gene; fluorescent reporter genes such as the green, red, yellow or blue fluorescent protein-encoding genes; and luminescence-based reporter genes such as the luciferase gene, amongst others which permit optical selection of cells using techniques such as Fluorescence-Activated Cell Sorting (FACS).

Furthermore, it should be noted that the selectable marker gene may be a distinct open reading frame in the construct or may be expressed as a fusion protein with another polypeptide (e.g. the CAR).

As set out above, the nucleic acid construct may also comprise one or more transcriptional control sequences. The term "transcriptional control sequence" should be understood to include any nucleic acid sequence which effects the transcription of an operably connected nucleic acid. A transcriptional control sequence may include, for example, a leader, polyadenylation sequence, promoter, enhancer or upstream activating sequence, and transcription terminator. Typically, a transcriptional control sequence at least includes a promoter. The term "promoter" as used herein, describes any nucleic acid which confers, activates or enhances expression of a nucleic acid in a cell.

In some embodiments, at least one transcriptional control sequence is operably connected to the nucleic acid molecule of the second aspect of the invention. For the purposes of the present specification, a transcriptional control sequence is regarded as "operably connected" to a given nucleic acid molecule when the transcriptional control sequence is able to promote, inhibit or otherwise modulate the transcription of the nucleic acid molecule. Therefore, in some embodiments, the nucleic acid molecule is under the control of a transcription control sequence, such as a constitutive promoter or an inducible promoter.

The "nucleic acid construct" may be in any suitable form, such as in the form of a plasmid, phage, transposon, cosmid, chromosome, vector, etc., which is capable of replication when associated with the proper control elements and which can transfer gene sequences, contained within the construct, between cells. Thus, the term includes cloning and expression vehicles, as well as viral vectors. In some embodiments, the nucleic acid construct is a vector. In some embodiments the vector is a viral vector.

A promoter may regulate the expression of an operably connected nucleic acid molecule constitutively, or differentially, with respect to the cell, tissue, or organ at which expression occurs. As such, the promoter may include, for example, a constitutive promoter, or an inducible promoter. A "constitutive promoter" is a promoter that is active under most environmental and physiological conditions. An "inducible promoter" is a promoter that is active under specific environmental or physiological conditions. The present invention contemplates the use of any promoter which is active in a cell of interest. As such, a wide array of promoters would be readily ascertained by one of ordinary skill in the art.

Mammalian constitutive promoters may include, but are not limited to, Simian virus 40 (SV40), cytomegalovirus (CMV), β-actin, Ubiquitin C (UBC), elongation factor-1 alpha (EF1A), phosphoglycerate kinase (PGK) and CMV early enhancer/chicken β actin (CAGG).

Inducible promoters may include, but are not limited to, chemically inducible promoters and physically inducible promoters. Chemically inducible promoters include promoters which have activity that is regulated by chemical compounds such as alcohols, antibiotics, steroids, metal ions or other compounds. Examples of chemically inducible promoters include: tetracycline regulated promoters (e.g. see U.S. Pat. Nos. 5,851,796 and 5,464,758); steroid responsive promoters such as glucocorticoid receptor promoters (e.g. see U.S. Pat. No. 5,512,483), ecdysone receptor promoters (e.g. see U.S. Pat. No. 6,379,945) and the like; and metal-responsive promoters such as metallothionein promoters (e.g. see U.S. Pat. Nos. 4,940,661, 4,579,821 and 4,601,978) amongst others.

As mentioned above, the control sequences may also include a terminator. The term "terminator" refers to a DNA sequence at the end of a transcriptional unit which signals termination of transcription. Terminators are 3-non-translated DNA sequences generally containing a polyadenylation signal, which facilitate the addition of polyadenylate sequences to the 3-end of a primary transcript. As with promoter sequences, the terminator may be any terminator sequence which is operable in the cells, tissues or organs in which it is intended to be used. Suitable terminators would be known to a person skilled in the art.

As will be understood, the nucleic acid construct of the third aspect of the invention can further include additional sequences, for example sequences that permit enhanced expression, cytoplasmic or membrane transportation, and location signals. Specific non-limiting examples include an Internal Ribosome Entry Site (IRES).

The present invention extends to all genetic constructs essentially as described herein. These constructs may further include nucleotide sequences intended for the maintenance and/or replication of the genetic construct in eukaryotes and/or the integration of the genetic construct or a part thereof into the genome of a eukaryotic cell.

Methods are known in the art for the deliberate introduction (transfection/transduction) of exogenous genetic material, such as the nucleic acid construct of the third aspect of the present invention, into eukaryotic cells. As will be understood the method best suited for introducing the nucleic acid construct into the desired host cell is dependent on many factors, such as the size of the nucleic acid construct, the type of host cell the desired rate of efficiency of the transfection/transduction and the final desired, or required, viability of the transfected/transduced cells. Non-limiting examples of such methods include; chemical transfection with chemicals such as cationic polymers, calcium phosphate, or structures such as liposomes and dendrimers; non-chemical methods such as electroporation, sonoporations, heat-shock or optical transfection; particle-based methods such as 'gene gun' delivery, magnetofection, or impalefection or viral transduction.

The nucleic acid construct will be selected depending on the desired method of transfection/transduction. In some embodiments of the third aspect of the invention, the nucleic acid construct is a viral vector, and the method for introducing the nucleic acid construct into a host cell is viral transduction. Methods are known in the art for utilising viral transduction to elicit expression of a CAR in a PBMC (Parker, L L. et al. Hum Gene Ther. 2000; 11: 2377-87) and more generally utilising retroviral systems for transduction of mammalian cells (Cepko, C. and Pear, W. Curr Protoc Mol Biol. 2001, unit 9.9). In other embodiments, the nucleic acid construct is a plasmid, a cosmid, an artificial chromosome or the like, and can be transfected into the cell by any suitable method known in the art.

In a fourth aspect the present invention provides a genetically modified cell that includes the chimeric antigen receptor according to the first aspect of the invention.

In some embodiments of the fourth aspect of the invention, the genetically modified cell includes two or more different CARs.

In a fifth aspect the invention provides a genetically modified cell that includes the nucleic acid molecule according to the second aspect of the invention, or includes the nucleic acid construct according to the third aspect of the invention, or a genomically integrated form of the nucleic acid construct.

In some embodiments of the fifth aspect of the invention, the genetically modified cell includes a nucleic acid molecule, or a nucleic acid construct, that encodes for two or more different CARs. In some embodiments of the fifth aspect of the invention, the genetically modified cell includes two or more nucleic acid molecules, or two or more nucleic acid constructs, each of which encodes for a different CAR.

As referred to herein, a "genetically modified cell" includes any cell comprising a non-naturally occurring and/or introduced nucleic acid molecule or nucleic acid construct encompassed by the present invention. The introduced nucleic acid molecule or nucleic acid construct may be maintained in the cell as a discreet DNA molecule, or it may be integrated into the genomic DNA of the cell.

Genomic DNA of a cell should be understood in its broadest context to include any and all endogenous DNA that makes up the genetic complement of a cell. As such, the genomic DNA of a cell should be understood to include chromosomes, mitochondrial DNA and the like. As such, the term "genomically integrated" contemplates chromosomal integration, mitochondrial DNA integration, and the like. The "genomically integrated form" of the construct may be all or part of the construct. However, in some embodiments the genomically integrated form of the construct at least includes the nucleic acid molecule of the second aspect of the invention.

As used herein, the term "different CARs" or "different chimeric antigen receptors" refers to any two or more CARs that have either non-identical antigen-recognition and/or non-identical signalling domains. In one example, "different CARs" includes two CARs with the same antigen-recognition domains (e.g. both CARs may recognise a dysfunctional $P2X_7$ receptor), but have different signalling domains, such as one CAR having a signalling domain with a portion of an activation receptor and the other CAR having a signalling domain with a portion of an co-stimulatory receptor. As will be understood, at least one of the two or more CARs within this embodiment will have an antigen-recognition domain that recognises the dysfunctional $P2X_7$ receptor and the other CAR(s) may take any suitable form and may be directed against any suitable antigen.

Accordingly, in some embodiments of the fourth and fifth aspects of the invention the two or more different CARs have different signalling domains, and may have identical, or different, antigen-recognition domains. Specifically, the genetically modified cell according to the fourth or fifth aspects of the invention may include a first chimeric antigen receptor with a signalling domain that includes a portion derived from an activation receptor and a second chimeric antigen receptor with a signalling domain including a portion derived from a co-stimulatory receptor.

In some embodiments of the fourth or fifth aspects of the invention, the activation receptor (from which a portion of signalling domain is derived) is the CD3 co-receptor complex or is an Fc receptor.

In some embodiments of the fourth or fifth aspects of the invention, the co-stimulatory receptor (from which a portion of signalling domain is derived) is selected from the group consisting of CD27, CD28, CD-30, CD40, DAP10, OX40, 4-1BB (CD137) and ICOS.

In some embodiments of the fourth or fifth aspects of the invention, the co-stimulatory receptor (from which a portion of signalling domain is derived) is selected from the group consisting of CD28, OX40 or 4-1BB.

In some embodiments of the fourth and fifth aspects of the invention, the genetically modified cell is further modified to constitutively express co-stimulatory receptors.

As described above, a cellular immune response is typically only induced when an activation signal (typically in response to an antigen) and a co-stimulation signal are simultaneously experienced. Therefore, by having a genetically modified cell in accordance with some of the above embodiments, which includes two or more CARs that in combination provide both an intracellular activation signal and an intracellular co-stimulation signal, ensures that a sufficient immune response can be induce in response to the recognition by the CAR(s) of their cognate antigen. Alternatively, the genetically modified cell may include only one CAR, which has an antigen-recognition domain that recognises a dysfunctional $P2X_7$ receptor, and may constitutively express co-stimulatory receptors, thereby increasing the likelihood of co-stimulation being provided simultaneously when the CAR is activated. Alternatively, the genetically modified cell may be further modified to constitutively express both co-stimulatory receptor(s) and its/their ligand(s). In this way the cell is continuously experiencing co-stimulation and only needs the activation of a CAR, with a signalling domain including a portion from an activation receptor, for immune activation of the cell.

Therefore in some embodiments of the fourth or fifth aspects of the invention, the genetically modified cell is further modified so as to constitutively express co-stimulatory receptors. In further embodiments, the genetically modified cell is further modified so as to express ligands for the co-stimulatory receptors, thereby facilitating auto-stimulation of the cell. Examples of CAR-expressing T cells that also express both co-stimulatory receptors and their cognate ligands (so as to induce auto-stimulation) are known in the art and include, inter alia, those disclosed in Stephen M T. et al. Nat Med, 2007; 13: 1440-9.

The potency of a genetically modified cell including a CAR can be enhanced by further modifying the cell so as to secrete cytokines, preferably proinflammatory or proproliferative cytokines. This secretion of cytokines provide both autocrine support for the cell expressing the CAR, and alters the local environment surrounding the CAR-expressing cell such that other cells of the immune system are recruited and activated. Consequently, in some embodiments of the fourth or fifth aspects of the invention the genetically modified cell is further modified to secret cytokines. This secretion may be constitutive, or may be inducible upon recognition of a CAR of its cognate antigen of ligand.

Whilst any one or more cytokines can be selected depending on the desired immune response, preferable cytokines include IL-2, IL-7, IL-12, IL-15, IL-17 and IL-21, or a combination thereof.

The genetically modified cell of the fourth or fifth aspects of the invention can be any suitable immune cell, or can be a homogeneous or a heterogeneous cell population. In some embodiments, the cell is a leukocyte, a Peripheral Blood Mononuclear Cell (PBMC), a lymphocyte, a T cell, a CD4+ T cell, a CD8+ T cell, a natural killer cell or a natural killer T cell.

In a sixth aspect, the present invention provides a method of killing a cell expressing a dysfunctional $P2X_7$ receptor, the method including exposing the cell expressing a dysfunctional $P2X_7$ receptor to a genetically modified cell having a chimeric antigen receptor, wherein the chimeric antigen receptor is directed against the dysfunctional $P2X_7$ receptor.

Therefore, in some embodiments of the sixth aspect of the invention, the CAR directly recognises the dysfunctional $P2X_7$ receptor. In other embodiments, the CAR indirectly recognises the dysfunctional $P2X_7$ receptor.

As used herein the term "directly recognises" includes direct binding of the antigen-recognition domain of the CAR to the dysfunctional $P2X_7$ receptor, or an epitope thereof, when the receptor is present in its natural form. In another non-limiting example, the antigen-recognition domain may directly bind to a processed form of the dysfunctional P2X$_7$ receptor, which may be presented by antigen presenting molecules such as the major histocompatibility complex (MHC).

As an alternative to the CAR directly recognising a cell having a dysfunctional P2X$_7$ receptor, the CAR may be directed against a cell having a dysfunctional P2X$_7$ receptor by an indirect means.

Consequently, in some embodiments of the sixth aspect of the invention, the chimeric antigen receptor recognises the dysfunctional P2X$_7$ receptor via an intermediate. An intermediate may be a molecule such as a probe that binds or interacts directly with the dysfunctional P2X$_7$ receptor. Non-limiting examples of such probes include antibodies, a Fab of an antibody, a scFv, a soluble engineered TCR or an aptamer. The CAR may be able to directly recognise the probe or the probe may have a tag that is recognised by the CAR. In either regard the probe provides the specificity for the target cell (namely a cell having a dysfunctional P2X$_7$ receptor) whilst the genetically modified cell having the CAR provides the efficacy and directs an immune response against the target cell. Alternatively, the intermediate could be a cell endogenous marker which is associated with, or its expression is correlated to, the dysfunctional P2X$_7$ receptor. The dysregulation of the marker may be a cause of or a result of the dysfunction of the P2X$_7$ receptor.

In some embodiments of the sixth aspect of the invention, the method of killing a cell having a dysfunctional P2X$_7$ receptor further includes the step of exposing the cell having a dysfunctional P2X$_7$ receptor to an intermediate.

In some embodiments of the sixth aspect of the invention, the intermediate is a probe that binds to a dysfunctional P2X$_7$ receptor and the chimeric antigen receptor recognises the probe. Preferably the probe is an antibody or an aptamer.

The term "aptamer" as used throughout the specification refers to any oligonucleic acid, polynucleic acid, peptide or polypeptide which specifically binds to, or preferentially forms a complex with, a target (specifically a dysfunctional P2X$_7$ receptor).

In some embodiments of the sixth aspect of the invention, the probe includes a tag and the chimeric antigen receptor recognises the tag. Examples of a CAR that recognise cells by way of an intermediate are known in the art, for example European patent application EP 2651442.

In some embodiments of the sixth aspect of the invention, the cell having a dysfunctional P2X$_7$ receptor is within the body of a subject. In some embodiments, the subject is a human. In some embodiments, the method further includes exposing the cell expressing a dysfunctional P2X$_7$ receptor to a genetically modified together with an exogenous cytokine.

In some embodiments of the sixth aspect of the invention, the genetically modified cell is a genetically modified cell autologous to the cell expressing a dysfunctional P2X$_7$ receptor from the subject.

In some embodiments of the sixth aspect of the invention, the cell expressing a dysfunctional P2X$_7$ receptor is within the body of a subject. In some embodiments of the sixth aspect of the invention, the cell expressing a dysfunctional P2X$_7$ receptor is a cancer cell.

In some embodiments of the sixth aspect, the present invention provides a method of treating or preventing cancer in a subject, the method including providing a subject with a genetically modified cell having a chimeric antigen receptor, wherein the chimeric antigen receptor is directed against a target cell having a dysfunctional P2X$_7$ receptor.

The terms "treat", "treating" or "treatment," as used herein are to be understood to include within their scope one or more of the following outcomes: (i) inhibiting to some extent the growth of a primary tumour in a subject, including, slowing down and complete growth arrest, and including reducing the growth of the primary tumour after resection; (ii) inhibiting to some extent the growth and formation of one or more secondary tumours in a subject; (iii) reducing the number of tumour cells in a subject; (iv) reducing the size of a tumour in the subject; (v) inhibiting (i.e. reduction, slowing down or complete stopping) of tumour cell infiltration into peripheral organs; (vi) inhibiting (i.e. reduction, slowing down or complete stopping) of metastasis; (vii) improving the life expectancy of a subject as compared to the untreated state; (viii) improving the quality of life of a subject as compared to the untreated state; (ix) alleviating, abating or ameliorating at least one symptom of cancer in a subject; (x) causing regression or remission of cancer in a subject; (xi) relieving a condition in a subject that is caused by cancer; and (xii) stopping symptoms in a subject that are associated with cancer.

The terms "prevent" or "preventing" as used herein are to be understood to include within their scope inhibiting the formation of a primary tumour in a subject, inhibiting the formation of one or more secondary tumours in a subject, or reducing or eliminating the recurrence of cancer in a subject in remission.

The term "inhibiting" as used herein is taken to mean a decrease or reduction in the growth of a cancer, cancerous cell or tumour when compared to the growth in a control, such as an untreated cell or subject. In some embodiments, growth may be decreased or reduced by at least 10%, 20%, 30%, 40%, 50%, 60%, 70%, 80%, 90%, or 100%, relative to an untreated control.

Inhibition of the growth of a cancer, tumour or cancerous cell may be assessed by a range of methods known in the art. For example, for a cancerous cell in vitro, the growth of the cell may be determined by a suitable proliferation assay, or by method which assess the extent of incorporation of tritiated thymidine into cellular DNA over a given period of time. For a tumour or cancerous cell present in vivo, the growth of the tumour or cell may be determined for example by a suitable imaging method known in the art.

The term "subject" as used herein refers to any animal capable of suffering from cancer. Particular subjects of interest are human beings, and scientifically relevant species such as mice, rats, ferrets, guinea pigs, hamsters, non-human primates, dogs, pigs and sheep, or economically relevant animals such as horses, dogs, cats and cattle. In a preferred embodiment of the sixth aspect of the invention, the subject is a human.

A reference to "providing a subject with" relates to administering to the subject the genetically modified cell. Alternatively, the genetically modified cell may be generated within the subject. For example, the genetically modified cell may be generated in vivo such that the subject has an endogenous population of genetically modified cells. Suitable means for such in vivo generation are known in the art and include gene therapy of a subject.

As used throughout the specification a reference to a CAR being "directed" against a target cell having a dysfunctional P2X$_7$ receptor contemplates the selective targeting of an immune response toward a cell based on the cell having a dysfunctional P2X$_7$ receptor. Importantly, such targeting is not limited to direct recognition of the dysfunctional P2X$_7$ receptor by a CAR. That is to say that the CAR itself does not have to directly recognise or bind to the dysfunctional P2X$_7$ receptor but merely has to be able to selectively recognise and be activated by a cell that expresses a dysfunctional P2X$_7$ receptor.

Therefore, in some embodiments of the sixth aspect of the invention, the CAR directly recognises the dysfunctional P2X$_7$ receptor. In other embodiments, the CAR indirectly recognises the dysfunctional P2X$_7$ receptor.

As used herein the term "directly recognises" includes direct binding of the antigen-recognition domain of the CAR to the dysfunctional P2X$_7$ receptor, or an epitope thereof, when the receptor is present in its natural form. In another non-limiting example, the antigen-recognition domain may directly bind to a processed form of the dysfunctional P2X$_7$ receptor, which may be presented by antigen presenting molecules such as the major histocompatibility complex (MHC).

As an alternative to the CAR directly recognising a cell having a dysfunctional P2X$_7$ receptor, the CAR may be directed against a target cell having a dysfunctional P2X$_7$ receptor by an indirect means.

Consequently, in some embodiments of the sixth aspect of the invention, the chimeric antigen receptor recognises the dysfunctional P2X$_7$ receptor via an intermediate. An intermediate may be a molecule such as a probe that binds or interacts directly with the dysfunctional P2X$_7$ receptor. Non-limiting examples of such probes include antibodies, a Fab of an antibody, a scFv, a soluble engineered TCR or an aptamer. The CAR may be able to directly recognise the probe or the probe may have a tag that is recognised by the CAR. In either regard the probe provides the specificity for the target cell (namely a cell having a dysfunctional P2X$_7$ receptor) whilst the genetically modified cell having the CAR provides the efficacy and directs an immune response against the target cell. Alternatively, the intermediate could be a cell endogenous marker which is associated with, or its expression is correlated to, the dysfunctional P2X$_7$ receptor. The dysregulation of the marker may be a cause of or a result of the dysfunction of the P2X$_7$ receptor.

In some embodiments of the sixth aspect of the invention, the method of treating or preventing cancer in a subject further includes the step of providing the subject with an intermediate.

In some embodiments of the sixth aspect of the invention, the intermediate is a probe that binds to a dysfunctional P2X$_7$ receptor and the chimeric antigen receptor recognises the probe. Preferably the probe is an antibody or an aptamer.

The term "aptamer" as used throughout the specification refers to any oligonucleic acid, polynucleic acid, peptide or polypeptide which specifically binds to, or preferentially forms a complex with, a target (specifically a dysfunctional P2X$_7$ receptor).

In some embodiments of the sixth aspect of the invention, the probe includes a tag and the chimeric antigen receptor recognises the tag. Examples of a CAR that recognise cells by way of an intermediate are known in the art, for example European patent application EP 2651442.

In a seventh aspect, the present invention provides a method of treating or preventing cancer in a subject, the method including administering to the subject a genetically modified cell according to a fourth or fifth aspect of the invention.

Whilst the provision of a genetically modified cell expressing a CAR directed against a target cell having a dysfunctional P2X$_7$ receptor may be sufficient to provide effective immunotherapy against precancerous or cancerous cells, the provision of adjuvants together with the genetically modified cells may further enhance the induction of the immune response and may augment the immunotherapy. Cytokines, preferably proinflammatory cytokines, are particularly suitable adjuvants for provision to a subject together with genetically modified cells having CARs.

Therefore, in some embodiments of the sixth and seventh aspects of the invention, the genetically modified cell is administered to the subject together with a cytokine. It is to be understood that as used throughout the specification the term "together with" includes the genetically modified cell being administered simultaneously with a cytokine or administered in combination with a cytokine. Consequently, when administered in combination with a cytokine this may be considered to include a combination therapy whereby a subject's immunotherapy includes both treatment with a cytokine and treatment with a genetically modified cell having a CAR directed against a target cell expressing a dysfunctional P2X$_7$ receptor. In some forms, the cytokine is administered on a different day (>24 hrs) to the administration of the genetically modified cells. In other forms the cytokine is administered on the same day (within 24 hrs) as the genetically modified cells. In further forms the cytokine(s) and the genetically modified cell is administered within 18 hrs, 12 hrs, 6 hrs, 4 hrs, 2 hrs, 1 hr, 45 mins, 30 mins, 15 mins, 10 mins, 5 mins, 2 mins or 1 min of each other.

Suitable cytokines for administration together with the genetically modified cell include IL-2, IL-4, IL-6, IL-7, IL-9, IL-12, IL-15, IL-17, IL-18, IL-21, IL-23, IFNα, IFNβ, IFNγ, GM-CSF, TGFβ and TNFα. Preferred cytokines include IL-2 and IFNα. Furthermore, the cytokines may be administered as recombinant forms, natural forms, or via delivery systems such as fusions with proteins, delivered as a nucleic acid sequence which is expressed in the genetically modified cell or conjugated with a polymer such a polyethylene glycol (PEG).

The cell to be genetically modified can be obtained from any suitable source. In some embodiments of the sixth or seventh aspects of the invention the cell to be genetically modified is an autologous cell, being a cell autologous to the cell expressing a dysfunctional P2X$_7$ receptor. Advantageously, an autologous cell would not be recognised as 'non-self' by the subject's immune system and would therefore be tolerated by the subject. However, in some forms of cancer suitable autologous cells may not be readily available. Therefore, in some embodiments of the invention the cell to be genetically modified is an allogeneic or heterologous cell.

P2X$_7$ dysfunction is a common molecular alteration in a variety of cancers. Consequently, the method of the sixth or seventh aspects of the invention can be used for the prevention and treatment of a variety of cancers.

In some embodiments of the sixth or seventh aspects of the invention the method is used for the prevention or treatment of a cancer selected from one or more of; brain cancer, oesophageal cancer, mouth cancer, tongue cancer, thyroid cancer, lung cancer, stomach cancer, pancreatic cancer, kidney cancer, colon cancer, rectal cancer, prostate cancer, bladder cancer, cervical cancer, epithelial cell cancers, skin cancer, leukaemia, lymphoma, myeloma, breast cancer, ovarian cancer, endometrial cancer, testicular cancer. Preferably the cancer is selected from one or more of lung cancer, oesophageal cancer, stomach cancer, colon cancer, prostate cancer, bladder cancer, cervical cancer, vaginal cancers, epithelial cell cancers, skin cancer, blood-related cancers, breast cancer, endometrial cancer, uterine cancer testicular cancer.

In some embodiments of the sixth or seventh aspects of the invention, the cancer is metastatic cancer, such as stage III or stage IV cancer.

Upon creation of a genetically modified cell in accordance with the fourth or fifth aspects of the invention it may be desirable to expand the cell population in vitro to increase the total cell numbers available for use in treatment. This can be done using the step of exposing the cell to an antigen for the CAR. Accordingly, in an eighth aspect the present invention provides a method of expanding in vitro the genetically modified cell according to the fourth or fifth aspects of the invention, the method including the step of exposing the cell to an antigen for the CAR. In some embodiments, the method includes the further step of exposing the cell to a cytokine.

In a ninth aspect, the present invention provides a method of expanding in vitro the genetically modified cell according to the fourth or fifth aspects of the invention, the method including the step of exposing the cell to an antigen for the CAR and simultaneously exposing the cell to a cytokine.

Preferable cytokines used in the eighth or ninth aspects of the invention include members of the IL-2 subfamily, the interferon subfamily, the IL-10 subfamily, the IL-1 subfamily, the IL-17 subfamily or the TGF-β subfamily. In some embodiments of the eighth or ninth aspects of the invention, the cytokine is selected from the group consisting of IFN-γ, IL-2, IL-5, IL-7, IL-8, IL-10, IL-12, IL-13, IL-15, IL-17, IL-18, TNF-α, TGF-β1, TGF-β2, TGF-β3 and GM-CSF, or a combination thereof.

In a tenth aspect, the present invention provides a method of expanding in vitro the genetically modified cell according to the fourth or fifth aspects of the invention, the method including exposing the cell to immobilised anti-CD3 and anti-CD28 antibodies. In some embodiments of the tenth aspect of the invention, the antibodies are immobilised on a beaded substrate (for example "Human Activator" Dynabeads™). In some embodiments of the tenth aspect of the invention, the antibodies are immobilised on an alternative surface such as the surface of a tissue culture vessel, a culture flask, plate or bioreactor.

As would be understood by a person skilled in the art, depending on the signalling domain of the CAR, recognition by the CAR of its cognate antigen will lead to intracellular signalling that may ultimately lead to cellular proliferation. Accordingly, small numbers of cells, or even individual cells, can be expanded (or in the case of a single cell, clonally expanded) to form therapeutically significant numbers. This process can be further enhanced by the provision of cytokines.

The delivery or administration of the genetically modified cell according to a fourth or fifth aspect of the invention may be delivery or administration of the cell alone, or delivery or administration of the cell formulated into a suitable pharmaceutical composition. Accordingly, in an eleventh aspect, the present invention provides a pharmaceutical composition including a genetically modified cell according to a fourth or fifth aspect of the invention, and a pharmaceutically acceptable carrier.

Methods are known in the art for providing CAR-containing cells for immunotherapy (see for example Kershaw, MH. et al. Clin Cancer Res. 2006; 12(20): 6106-15; Parker L L. et al. Hum Gene Ther 2000; 11: 2337-87). Furthermore, protocols and methods are known in the art for the preparation, expansion and assessment of mammalian CAR-expressing cells (see for example Cheadle, E J. et al. Antibody Engineering: Methods and Protocols, Second Edition, Methods in Molecular Biology, vol. 907: 645-66) and are summarised in the Examples below.

The pharmaceutical composition may also include one or more pharmaceutically acceptable additives, including pharmaceutically acceptable salts, amino acids, polypeptides, polymers, solvents, buffers, excipients and bulking agents, taking into consideration the particular physical and chemical characteristics of the cell to be administered. In some embodiments, the pharmaceutical composition includes a suspension of genetically modified cells according to the fourth or fifth aspects of the invention in a suitable medium, such as isotonic saline solution. In some embodiments, the pharmaceutical composition may include suitable adjuvants such as one or more cytokines as described above. In some embodiments, the pharmaceutical composition may also include an intermediate as described above.

Administration of the pharmaceutical composition may also be via parenteral means which include intravenous, intraventricular, intraperitoneal, intramuscular or intracranial injection, or local injections to the site of a tumour or cancerous mass.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Finally, reference is made to standard textbooks of molecular biology that contain methods for carrying out basic techniques encompassed by the present invention. See, for example, Green MR and Sambrook J, Molecular Cloning: A Laboratory Manual (4th edition), Cold Spring Harbor Laboratory Press, 2012.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

The invention is further illustrated in the following examples. The examples are for the purpose of describing particular embodiments only and are not intended to be limiting with respect to the above description Example 1

Protocol for PEP2-2-3 Binding Peptide Chimeric Antigen Receptor (CAR) Design and Expression An exemplified protocol detailing the process of designing and expressing an anti-non-functional (nf) P2X$_7$ receptor CAR according to an embodiment of the present invention is detailed as follows.

Design of PEP2-2-3 (anti-nf P2x$_7$) Chimeric Antigen Receptor

An anti-nfP2x$_7$ chimeric antigen receptor (CAR) was designed according to the schematic illustrated in FIG. 1.

An antigen-recognition domain 1 of the CAR was generated which included the amino acid sequence of the PEP2-2-3 binding peptide (amino acid sequence set forth in SEQ ID NO: 10 and nucleotide sequence set forth in SEQ ID NO: 11). The PEP2-2-3 sequence was shown to have specific affinity for the dysfunctional P2X$_7$ receptor expressed on cancer cells, such as prostate LNCap cells, without significant affinity for monocytes or lymphocytes.

A CD8a signalling peptide 2 (having the amino acid sequence set forth in SEQ ID NO: 12 and the nucleotide sequence set forth in SEQ ID NO: 13) was linked to the N-terminus of the PEP2-2-3 antigen-recognition domain 1. The CD8a signalling peptide 2 includes a Kozak consensus sequence at positions 1 to 13 of SEQ ID NO: 13. The CD8a signalling peptide 2, including the Kozak sequence, acts to facilitate recognition of the transcribed RNA by the ribosome and provides a translation start site, thereby promoting translation of the transcribed RNA sequence of the CAR to a protein.

The antigen-recognition domain 1 of the CAR was linked to a transmembrane domain 3 via one of two hinge regions, termed long hinge 4 and short hinge 5. The provision of a long hinge 4 permits for flexibility of the antigen-recognition domain which may be required for the antigen-recognition domain to interact with its cognate ligand (dysfunctional $P2X_7$). The amino acid and nucleotide sequences for the long hinge 4 are set forth in SEQ ID NO: 14 and SEQ ID NO: 15, respectively. The amino acid and nucleotide sequences for the short hinge 5 are set forth in SEQ ID NO: 16 and SEQ ID NO: 17, respectively.

The transmembrane domain 3, and a portion of the intra-cellular domain 6, of the CAR is provided by a portion of the CD28 co-stimulatory receptor 7 (amino acid sequence set forth in SEQ ID NO: 18 and nucleotide sequence set forth in SEQ ID NO: 19). The intracellular domain further includes a portion of the co-stimulatory receptor OX40 8 (amino acid sequence set forth in SEQ ID NO: 20 and nucleotide sequence set forth in SEQ ID NO: 21) and a portion of the activation receptor CD3 zeta 9 (amino acid sequence set forth in SEQ ID NO: 22 and nucleotide sequence set forth in SEQ ID NO: 23).

A P2A sequence 10 (amino acid sequence set forth in SEQ ID NO: 24 and nucleotide sequence set forth in SEQ ID NO: 25) was added to the C-terminus of the CAR, permitting the post-translational excision of any peptide sequence attached to the C-terminus of the CAR. The amino acid sequence for the constructed anti-nfP2X$_7$ CAR-long hinge and the anti-nfP2X$_7$ CAR-short hinge are set forth in SEQ ID NOs: 26 and 27, respectively.

Lentival Vector Design and Assembly

Figure 2:
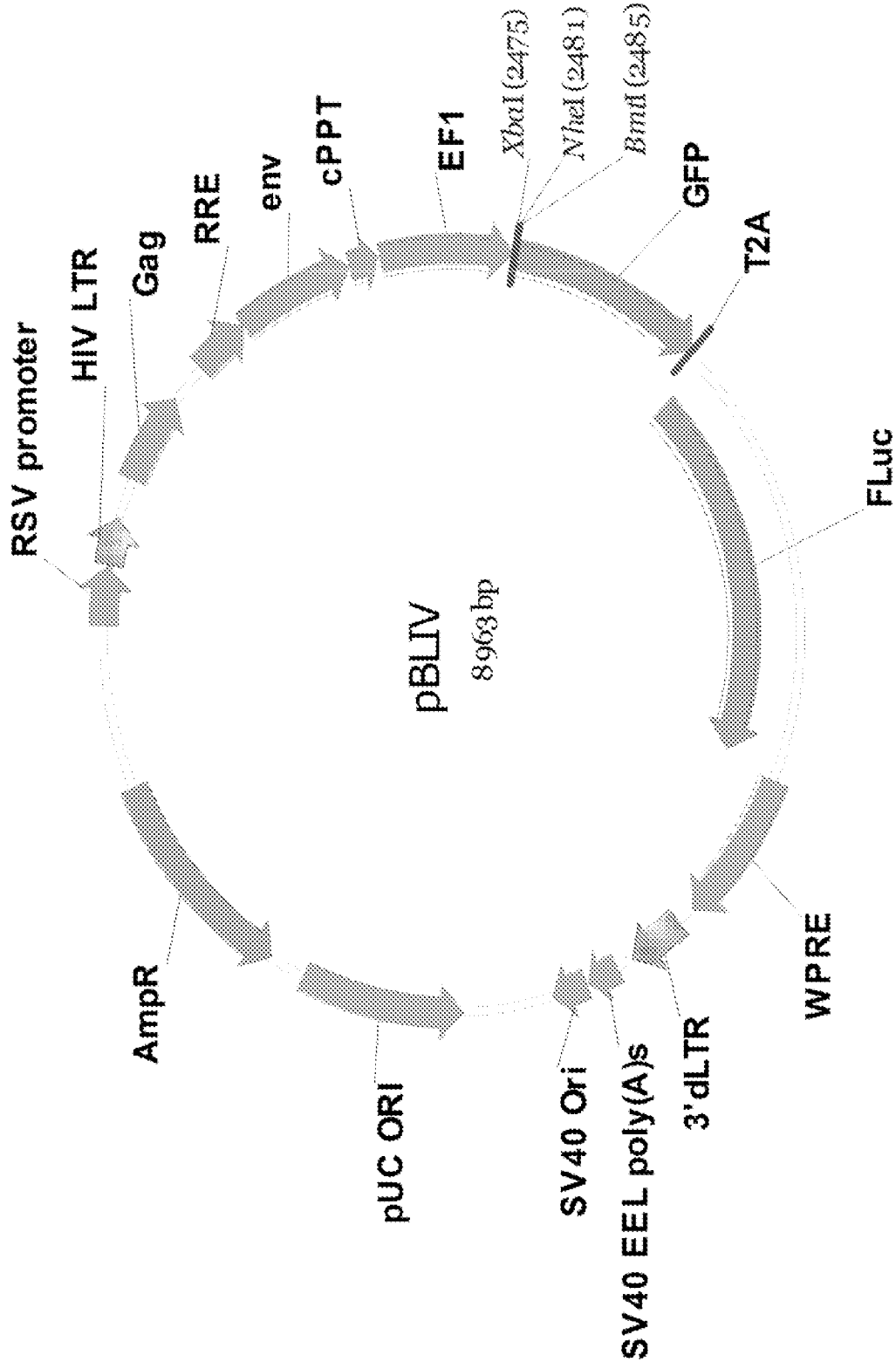
FIG. 2—a schematic showing the BLIV plasmid used for expression of the anti-nf P2X7 receptor CAR in FIG. 1.

The designed CARs were incorporated into the BLIV lentiviral plasmid (System Biosciences, California, USA) illustrated in FIG. 2, which includes the fluorescence and bioluminescence reporting proteins, green-fluorescence protein (GFP) and Firefly Luciferase (FLuc). The BLIV plasmid further includes a T2A coding sequence between the GFP and FLuc reporter protein coding sequences permitting for post-translational separation of the FLuc and GFP proteins.

Sequences having homology to the sequences upstream and downstream of the NheI restriction site of the BLIV vector were added to the 5' and 3' ends of the designed CARs to result in the final nucleotide sequences set forth in SEQ ID NO 28 (CAR-long hinge) and SEQ ID NO: 29 (CAR-short hinge). The inclusion of the 5' and 3' sequences permitted incorporation of the anti-nf P2X$_7$ CAR into the BLIV vector using Gibson cloning.

The nucleotide sequence for the anti-nf P2X$_7$ CAR-long hinge and anti-nf P2X$_7$ CAR-short hinge were constructed using gene blocks technology (gBlock™ Gene Fragments— Integrated DNA Technologies, Iowa, USA) and assembled using Gibson Assembly Cloning Kit (New England Biolabs inc. Ipswich MA, USA—cat #E5510S) in accordance with the manufacturer's instructions.

The BLIV plasmid was restricted at the NheI cloning site and the anti-nf P2X$_7$ CAR coding sequence was incorporated using Gibson assembly.

Cloning and Evaluation of BLIV-CAR Vector

New England Biolabs 5-alpha Competent E. coli cells (provided in Gibson Assembly Cloning Kit) were transformed with the generated BLIV-CAR vectors as per the manufacturer's instructions. Briefly:

A tube of NEB 5-alpha Competent E. coli cells was thawed on ice for 10 minutes;

1-5 µl containing 1 pg-100 ng of BLIV-CAR plasmid DNA was added to the cell mixture and mixed in by flicking the tube 4 to 5 times;

The E. coli and plasmid mixture was placed on ice for 30 minutes without mixing;

The cell and plasmid mixture were heat shocked at 42° C. for 30 seconds before being placed on ice for 5 minutes without mixing;

950 µl of SOC was added to the mixture before being heated to 37° C. for 60 minutes and shaken vigorously;

Selection plates were prepared and heated to 37° C.;

Serial 10-fold dilutions of the cells were prepared in SOC solution; and 50 to 100 µl of each dilution was spread onto selection plates followed by incubation overnight at 37° C.

Figure 3:
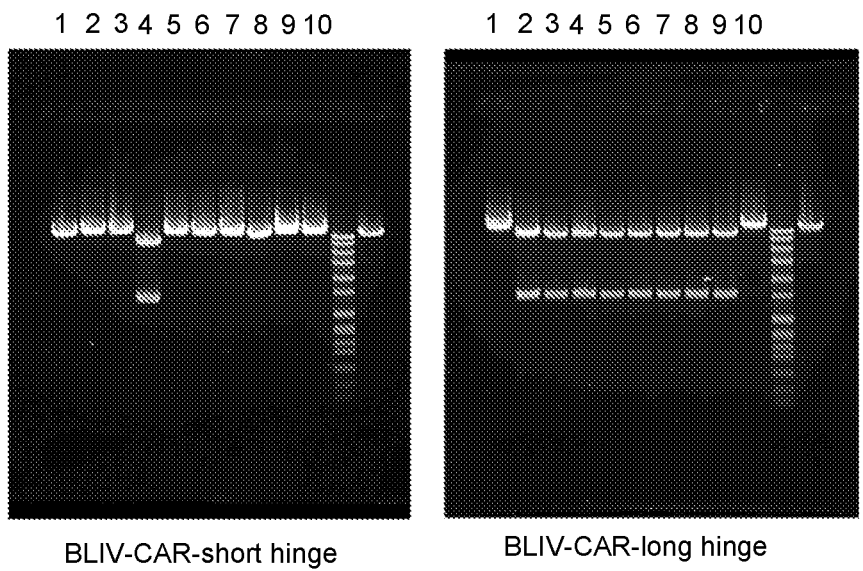
FIG. 3—an electrophoresis gel showing restriction fragments from BamHI restricted DNA isolated from E. coli clones transformed with the BLIV plasmid.

Following incubation of the transformed (E. coli) cells, 10 colonies of bacteria transformed with BLIV-CAR-short hinge plasmid and 10 colonies of bacteria transformed with the BLIV-CAR-Long hinge plasmid were isolated, plasmid DNA was purified, and restricted with a BamHI restriction enzyme. The restricted DNA was analysed via gel electrophoresis for appropriate sized restriction fragments. As shown in FIG. 3, colonies 2 to 9 of the bacterial clones transformed with the BLIV-CAR-long hinge plasmid contained the appropriately sized restriction fragments (7.8 kb and 2.8 kb), while only colony 4 of the bacterial clones transformed with the BLIV-CAR-short hinge plasmid provided the appropriate sized restriction fragments (7.4 kb and 2.8 kb).

Figure 4:
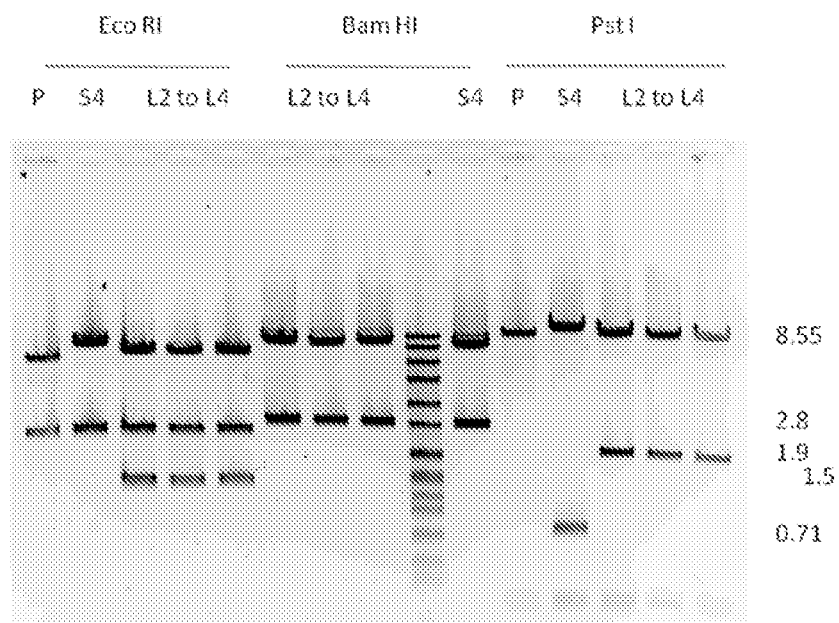
FIG. 4—an electrophoresis gel showing restriction fragments from EcoRI, BamHI and PstI restricted DNA isolated from selected E. coli clones transformed with the BLIV plasmid.

Clones 2 to 4 of the bacteria containing the BLIV-CAR-long hinge plasmid (L2 to L4), and clone 4 of the bacteria containing the BLIV-CAR-short hinge plasmid (S4) were selected for further confirmation of plasmid identity using EcoRI, BamHI and PstI restriction enzymes. All of the colonies showed restriction fragments of the expected length, as set out in Table 4 and FIG. 4.

TABLE 4

Expected Restriction Fragment Length of BLIV-CAR Plasmids

| Restriction Enzyme and Plasmid | Expected Length |
| --- | --- |
| Unmodified BLIV plasmid | 8.9 kb |
| Bam HI restricted BLIV-CAR-long hinge | 7.8 kb and 2.8 kb |
| Bam HI restricted BLIV-CAR-short hinge | 7.4 kb and 2.8 kb |
| Eco RI restricted BLIV-CAR-long hinge | 6.8 kb, 2.6 kb and 1.5 kb |
| Eco RI restricted BLIV-CAR-short hinge | 7.7 kb and 2.6 kb |
| Pst I restricted BLIV-CAR-long hinge | 8.6 kb, 2.0 kb and 0.22 kb |
| Pst I restricted BLIV-CAR-short hinge | 9.3 kb, 0.8 kb and 0.22 kb |

Construction and Verification of Lentiviral Vectors 293T cells were used to package lentivirus from a 3 plasmid protocol according to the following method.

Day 1: 293T cells were seeded in 35 ml DMEM media with 10% serum in a T-225 flask such that the cells were 90-95% confluent the following day.

Day 2: 30 ug of one of the generated BLIV-CAR plasmids (or an unmodified BLIV plasmid), 30 ug of gag-pol plasmid delta 8.2, and 15 ug of VSV-G plasmid (pMD2.G), were added to OptiMEM media to a final volume of 750 ul, and mixed. 300 ul of PEI solution were added and incubated at room temperature for at least 20 minutes. The mixture was then added to the confluent 293T cells before incubation at 37° C.

Day 3: Supernatant was decanted from the 293T cells 24 hours after addition of the plasmid mixture and stored at 4° C. The decanted mixture was replaced with 35 ml of fresh media before further incubation at 37° C.

Day 4: 48 hours after addition of the plasmid mixture, the media was removed and combined with the supernatant from the 24 hour harvest. The combined supernatants were spun for 15 minutes at 1500 g to remove any remaining cellular debris. The supernatant was filtered through a 0.45 um filter, and then spun at 17,000 rpm in a WX ultracentrifuge for one hour. After centrifugation, the supernatant was decanted by hand, with 50-200 ul remaining in the tube. The centrifuge tube was placed in a 50 ml screw-top tube in order to prevent contamination and evaporation and the virus was allowed to resuspend at 4° C. overnight.

Day 5: The virus was resuspended off the bottom of the centrifuge tube and transferred into a new 1.5 ml tube. The resuspended virus was spun for 5 minutes in a microcentrifuge tube at 5000 rpm to remove any remaining debris.

Transfection of 293T cells with the BLIV-CAR-short hinge and BLIV-CAR-long hinge vector was assessed after 24 hours of incubation by the presence of GFP fluorescence (see FIG. 5A and FIG. 6A). Supernatant collected at day 5 (as set out above) containing short- and long-hinge BLIV-CAR lentivirus vectors were incubated with fresh 293T cells and visualized for GFP fluorescence to test transduction capacity (see FIG. 5B and FIG. 6B).

Figure 7:
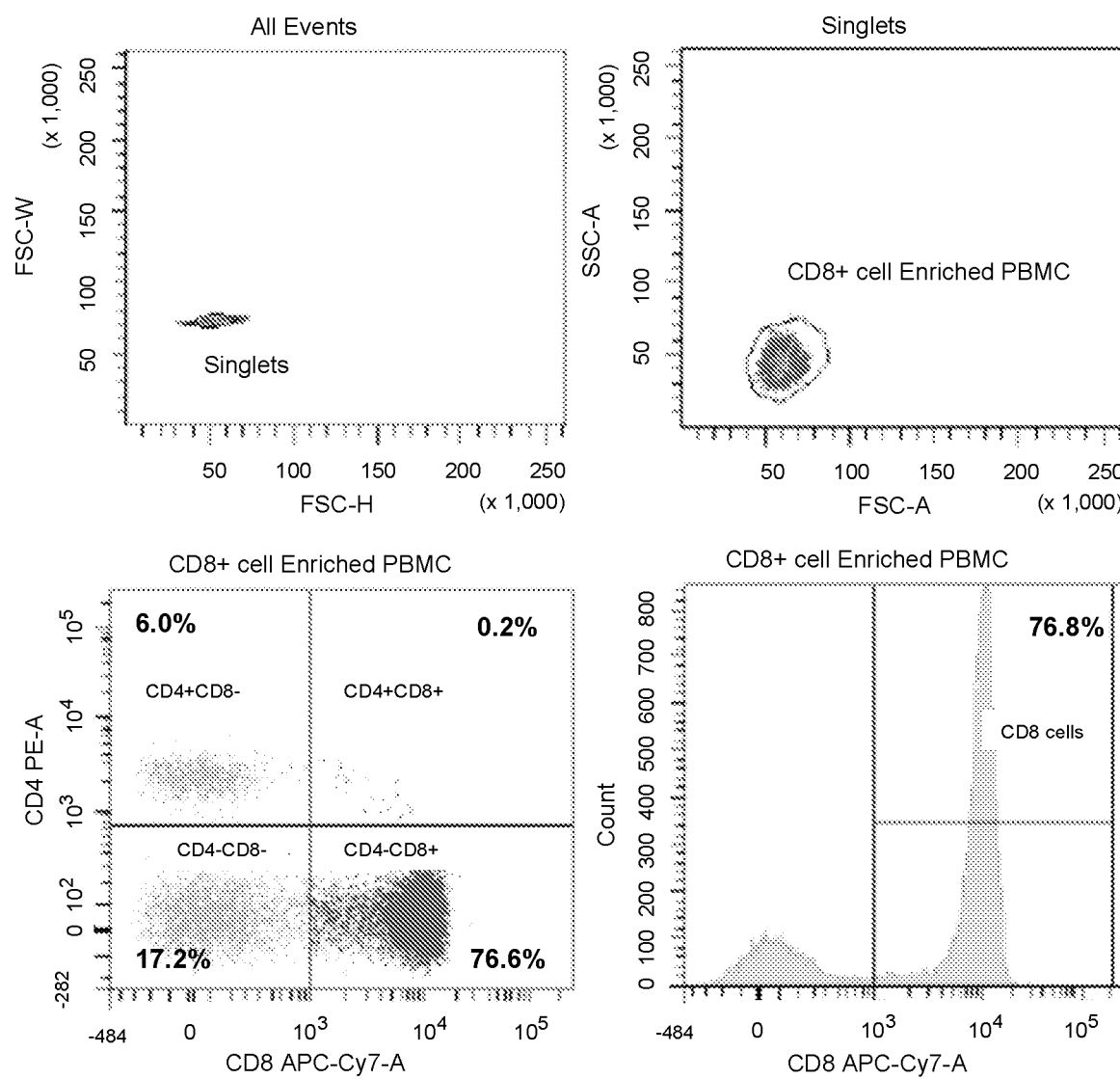
FIG. 7—FACS analysis of the cell purity of T cells purified with the RosetteSep human CD8+ T cell enrichment kit.

Screening for CAR T Cell Function $10^8$ CD8 T cells were isolated from 50 ml of human blood using the RosetteSep™ human CD8+ T cell isolation kit (Stemcell technologies, Vancouver, Canada) in accordance with the manufacturer's instructions. Analysis of the purity, as illustrated in FIG. 7, demonstrated that 76.6% of purified cells were CD8+

CD8+ T cells were incubated at $10^5$ cells per well with a 1:1 ratio of dynal T cell expander (CD3/CD28) beads. The CD8 cells were then incubated overnight together with lentiviral preparations, at a multiplicity of infection (MOI) of 5 or greater, containing either unmodified BLIV plasmids, BLIV-CAR-short hinge plasmids or BLIV-CAR-long hinge plasmids. Following incubation, the CD8+ T cells were washed before being co-cultured with the target cells.

Target cells expressing the non-functional $P2X_7$ receptor were provided by the mammary cancer cell line BT549 (ATCC HTB-122). These cells were dye-labelled using the fluorescent membrane intercalculating dye eFluor™ 670 (affymetrix eBioscience) as per the manufacturer's instructions. Briefly:

BT549 cells were prepared as a single-cell suspension and washed in PBS twice to remove any residual serum;

Cells were resuspended in room temperature PBS;

A 10 μM solution of Cell Proliferation Dye eFluor® 670 was prepared in room temperature PBS;

An equal volume of the 10 μM dye solution was added to the prepared BT549 cells to give a final concentration of 5 μM dye solution;

The BT549 cells in the dye solution were incubated for 10 minutes at 37° C. in the dark, before the labelling was stopped by adding 4 times the volume of cold culture medium containg 10% serum followed by incubation on ice for 5 minutes in the dark;

Finally cells were washed 3 times in culture medium before being resuspended in culture medium at the desired concentration.

Following dye labelling, target cells were co-culturing with the prepared CD8+ T cells at ratios of 10:1, 5:1, 1:1 and 0:1 (T cells:targets).

Figure 8A:
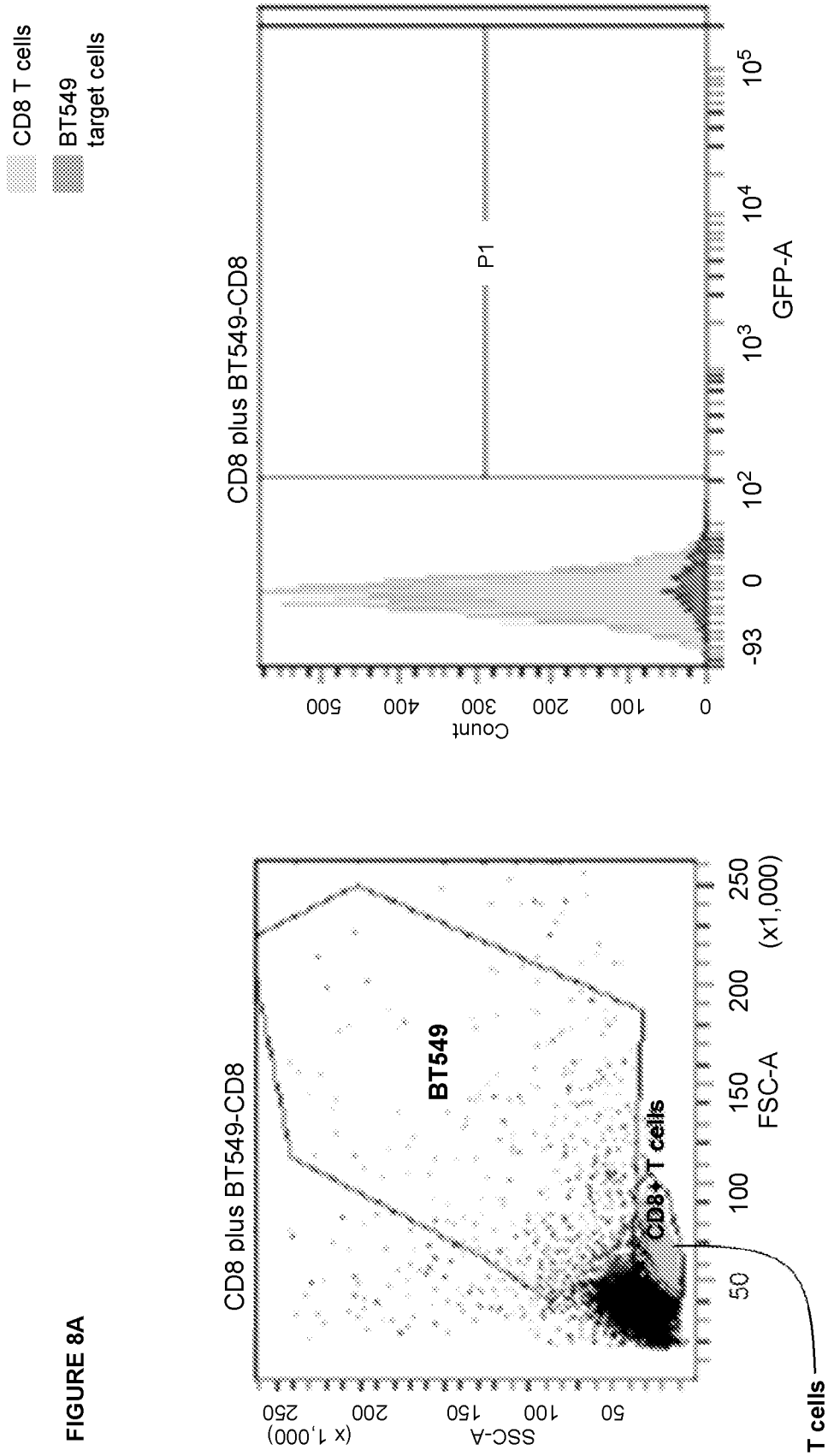
FIG. 8—FACS analysis of killing assays comprising the co-culturing of CD8+ T cells and BT549 cells.
Figure 8B:
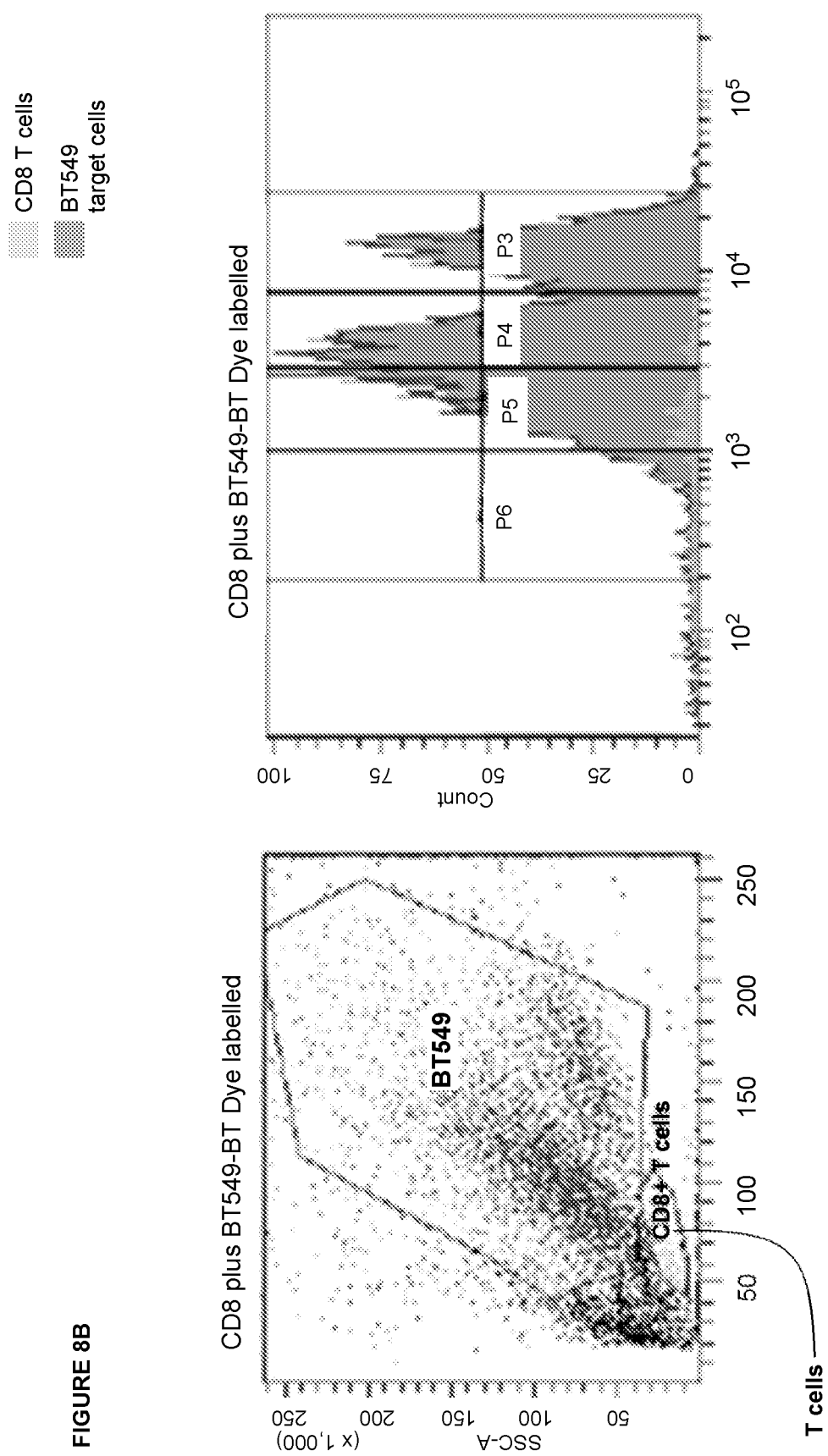
Figure 8C:
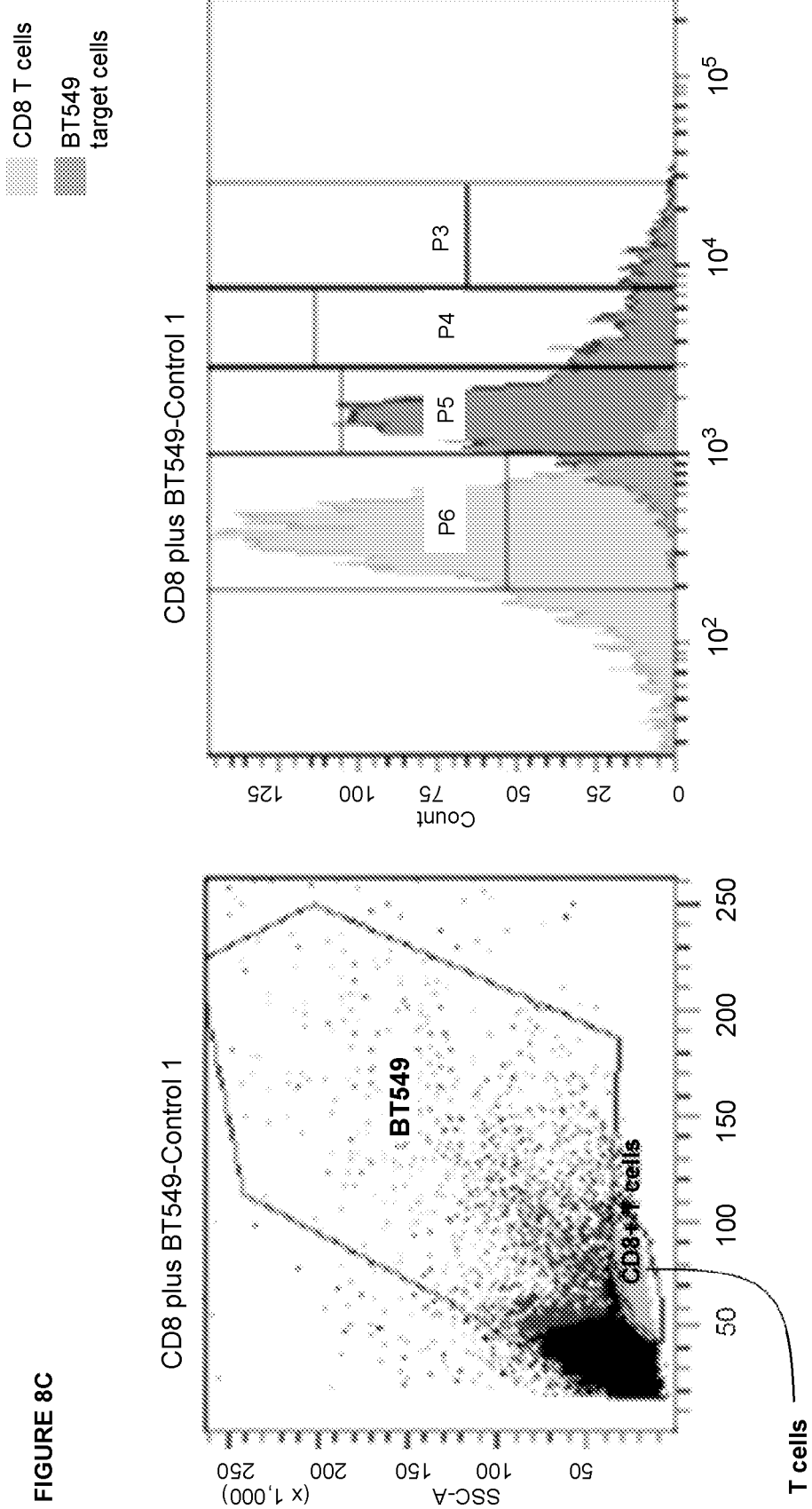
Figure 8D:
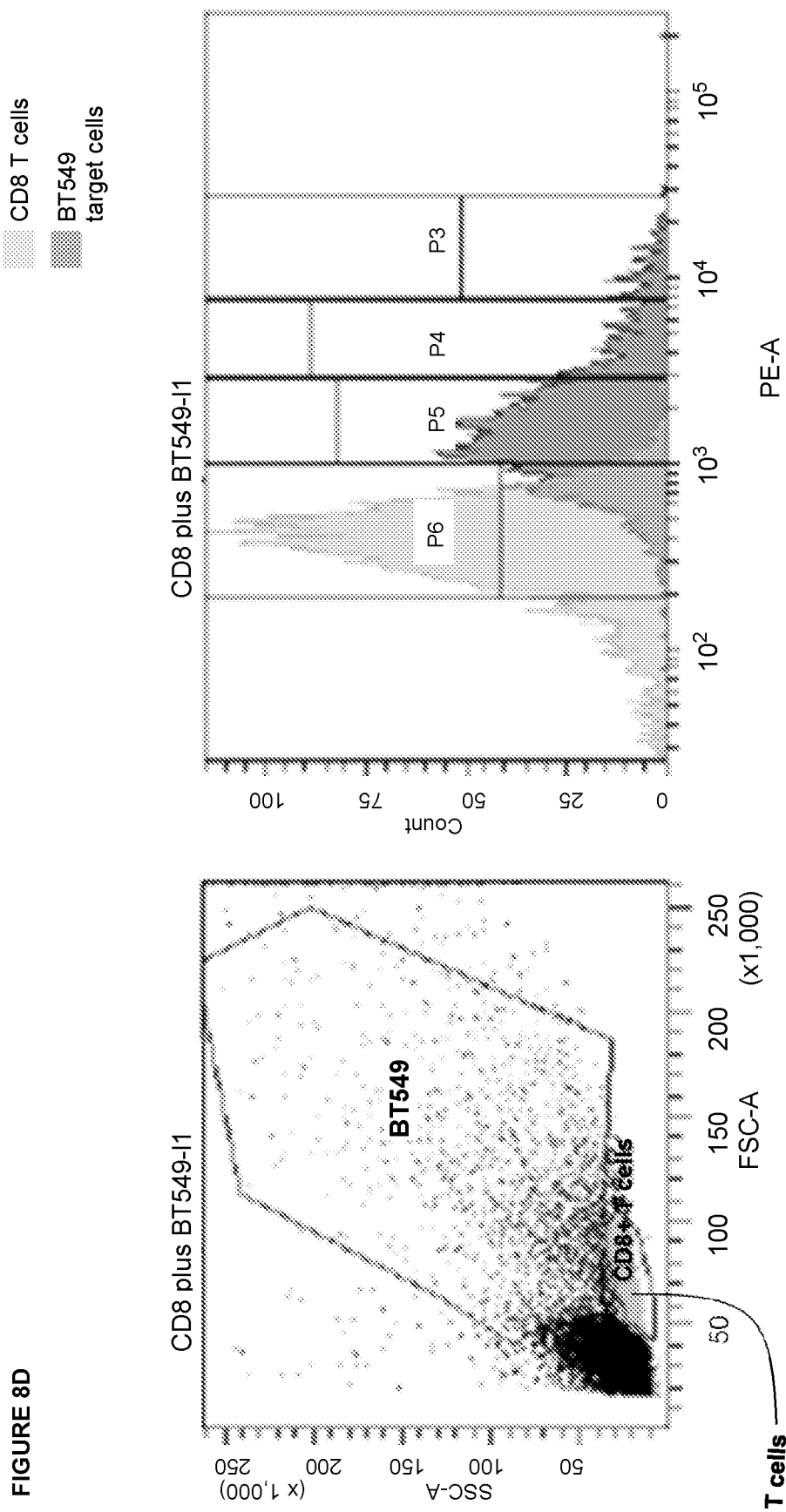
Figure 8E:
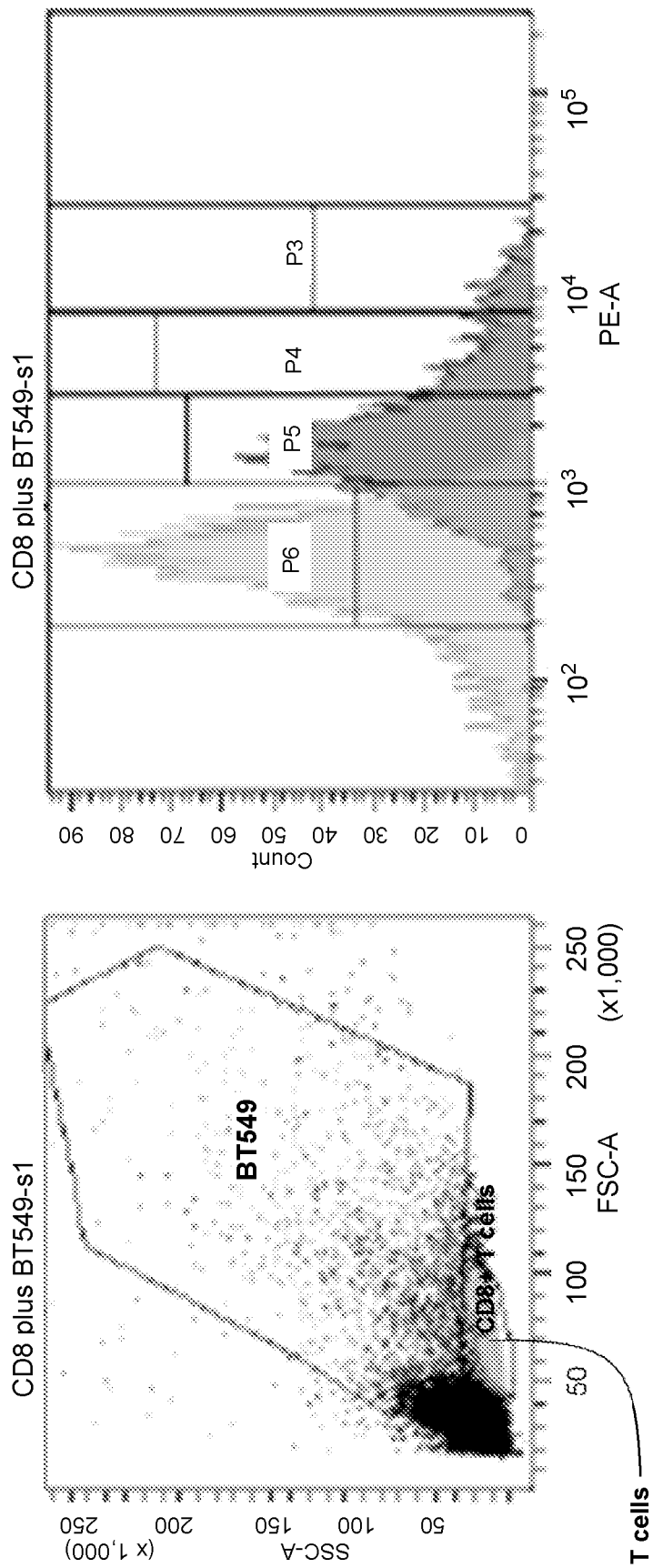

After 24 hrs of co-culture, cells were collected and analysed using Fluorescence-Activated Cell Sorting (FACS). The number of target cells containing the membrane intercalculating dye was quantified to assess if the co-cultured T cells led to target cell death or arrest of cell proliferation. The gating and analysis strategy used to quantify the efficacy of the CD8+ T cells at killing target cells is illustrated in FIG. 8, and is quantified in FIG. 9. FIG. 8A illustrates the gating and histogram analysis of labelled CD8+ T cells. FIG. 8B illustrates the gating and histogram analysis of labelled BT549 target cells. FIG. 8C illustrates the gating and histogram analysis after 24 hrs of co-culture of control CD8+ T cells and BT549 targets. FIG. 8D illustrates the gating and histogram analysis after 24 hrs of co-culture of CD8+ T cells transduced with BLIV-CAR-long hinge and BT549 target cells. FIG. 8E illustrates the gating and histogram analysis of 24 hr co-culture of CD8+ T cells transduced with BLIC-CAR-short hinge and BT549 target cells.

Figure 9:
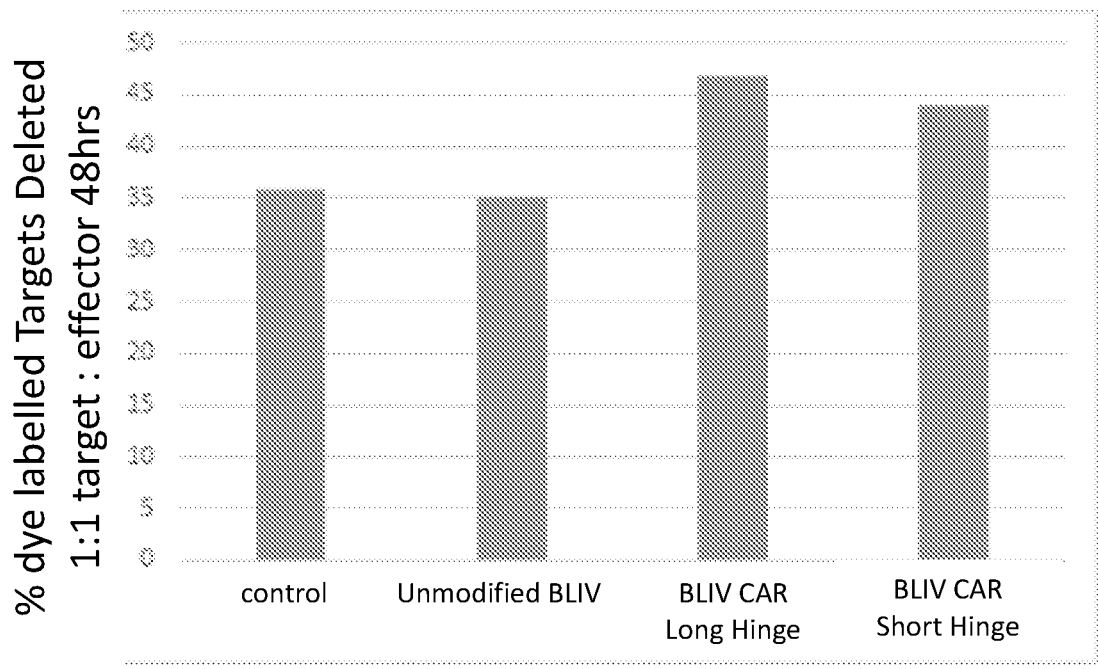
FIG. 9—Graph illustrating the percentage of dye-labelled target cells deleted after 48 hr of co-culture with CD8+ T cells transduced with lentiviral vectors containing the BLIV-CAR-short hinge and BLIV-CAR-short hinge plasmids compared to non-transduced CD8+ T cells and CD8+ T cells transduced with empty BLIV plasmids.

As can be seen in FIG. 9, there was an increase in the number of BT549 target cells deleted (killed) when the target cells were co-cultured with CD8 T cells transduced with lentivirus containing either the BLIV-CAR-long hinge or BLIV-CAR-short hinge, compared to the co-culture of the target cells with non-transduced or control transduced (unmodified BLIV vector) CD8 T cells.

In view of the results presented in FIG. 9, it is apparent that CD8+ T cells transduced with anti-nfP2X$_7$ CAR receptors (having either the short or the long hinge) demonstrate elevated levels of cytotoxic activity towards non-functional $P2X_7$ expressing target cells, demonstrating the ability of the CAR-T cells to kill cancer cell targets.

Example 2

Design of Alternative Anti-nfP2X7 Chimeric Antigen Receptor

A further exemplified protocol detailing the process of designing, and expressing on a T cell, an anti-non-functional (nf) $P2X_7$ receptor CAR, according to an embodiment of the present invention, is detailed below.

Anti-nfP2X$_7$ CARs were designed utilising three anti-non-functioning $P2X_7$ binding peptides. Specifically, CARs were designed to include antigen recognition domains with sequence homology to peptides PEP2-2-1-1, PEP2-472-2 or PEP2-2-12 (having the amino acid sequences set forth in SEQ ID NOs: 32, 33 and 34 respectively). These binding peptides have been shown to bind to the non-functional P2X7 receptor (Barden, J. A., Sluyter, R., Gu, B. J. & Wiley, J. S. 2003. Specific detection of non-functional human P2X(7) receptors in HEK293 cells and B-lymphocytes. FEBS Lett 538, 159-162).

The alignment of the above binding peptides to the heavy chain variable regions of antibodies that recognise non-functional $P2X_7$ receptors is shown in FIG. 10. The alignment of the Complementarity Determining Region (CDR 1 to 3) sequences are indicated by the boxes.

A specific example of the construction of a CAR having the PEP2-2-1-1 sequence is detailed below. The same CAR structure and sequences were used for CARs having PEP2-

472-2 or PEP2-2-12 sequences as the binding peptides, with the alternative binding peptides substituted for PEP2-2-1-1.

DNA sequences coding for the PEP2-2-1-1 binding peptide were synthesised in-frame with other DNA sequences to generate a CAR having the configuration described below.

Figure 11:
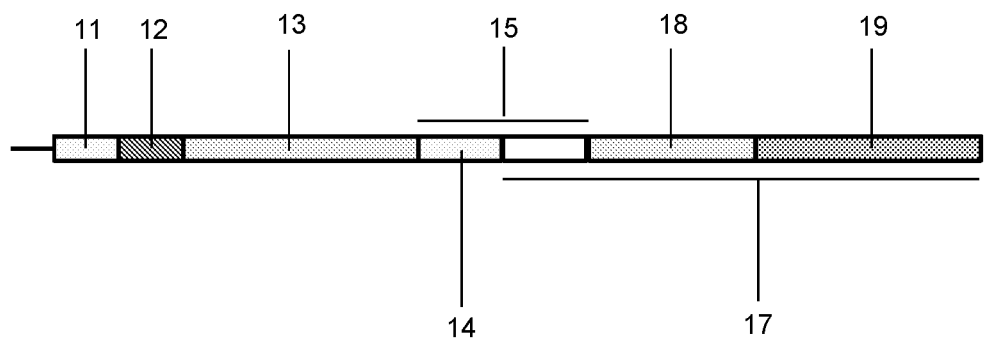
FIG. 11—A schematic showing the arrangement of an anti-nf $P2X_7$ receptor CAR according to a further embodiment of the present invention.
Figure 12:
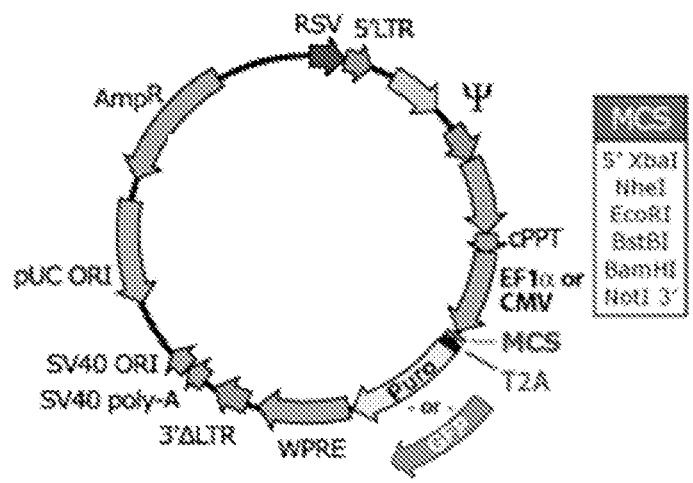
FIG. 12—A schematic showing the pCDH plasmid used for expression of an anti-nf $P2X_7$ receptor CAR of FIG. 11.

With reference to FIG. 11, an antigen recognition domain was prepared by linking a leader sequence of *Homo sapiens* CD8a molecule (CD8A) transcript variant 1 (having the amino acid sequence set forth in SEQ ID NO: 30 and the nucleotide sequence set forth in SEQ ID NO: 31) 11 to the N terminus of the PEP2-2-1-1 binding peptide 12 (having the amino acid sequence set forth in SEQ ID NO: 32 and the nucleotide sequence set forth in SEQ ID NO: 35).

The antigen recognition domain was then linked to a transmembrane domain via a modified IgG4 Hinge-CH2-CH4 13 having the sequence of the long hinge as set out in Example 1 above (i.e. the amino acid sequence set forth in SEQ ID NO: 14 and the nucleotide sequence set forth in SEQ ID NO: 15).

The extracellular domain comprising the CD8 leader sequence 11 and the PEP2-2-1 binding peptide 12 was linked to a transmembrane domain 14 provided by a portion of human CD28 15 (having the amino acid sequence set forth in SEQ ID NO: 18 and the nucleotide sequence set forth in SEQ ID NO: 19) which also included a portion of the CD28 cytoplasmic domains 16.

The intracellular portion of the CAR 17 was provided by a portion of the human CD28 molecule mentioned above 14 and the cytoplasmic domain of *Homo sapiens* tumour necrosis factor receptor superfamily member 4 (TNFRSF4/OX40—having the amino acid sequence set forth in SEQ ID NO: 20 and the nucleotide sequence set forth in SEQ ID NO: 21) 18 linked to the cytoplasmic domain of *Homo sapiens* CD247 molecule 19 (T-cell surface glycoprotein CD3 zeta chain, having the amino acid sequence set forth in SEQ ID NO: 22 and the nucleotide sequence set forth in SEQ ID NO: 23).

Lentival Vector Design and Assembly

The nucleotide sequences for the designed PEP2-2-1-1, PEP2-472-2 and PEP2-2-12 CARs were constructed using gene blocks technology (gBlock™ Gene Fragments—Integrated DNA Technologies, Iowa, USA) and assembled using Gibson Assembly Cloning Kit (New England Biolabs inc. Ipswich MA, USA—cat #E5510S) in accordance with the manufacturer's instructions. The sequences of the nucleotide constructs for PEP2-2-1-1, PEP2-472-2 or PEP2-2-12 CARs for integration in to cloning vectors (including restriction sites) are set out in SEQ ID NOs: 35, 36 and 37, respectively.

The CAR nucleotide constructs were incorporated into the pCDH-CMV-MCS-T2A (pCDH) vector (System Biosciences, California, USA Cat #CD524A-1) illustrated in FIG. 11, which includes the fluorescence reporting protein, green-fluorescence protein (GFP). The pCDH vector further includes a T2A coding sequence between the cloning site and the GFP permitting for post-translational separation of the cloned CAR and the GFP proteins.

For integration of PEP2-2-12 and PEP2-472-2 CAR nucleotide constructs into the pCDG vector, the pCDH vector was restricted with EcoR1 and NotI and gel purified (QIAquick gel extraction kit, QIAGEN). PEP2-2-12 and PEP2-472-2 CAR nucleotide gBlock constructs were also digested with EcoRI and NotI digestion enzymes. The restricted gBlock fragment was then purified with a QIAquick PCR purification kit in accordance with the manufacturer's instructions. The restricted vector was ligated with the restricted CAR constructs at a 3:1 molar ratio of insert to vector. Ligation mixes were transformed into chemical competent SURE2 cells (Agilent).

The PEP2-2-1-1 CAR construct contained an internal EcoR1 restriction site and therefore it was integrated into the pCDH vector in a manner different to the PEP2-2-12 and PEP2-472-2 CAR nucleotide constructs. The pCDH vector was restricted with EcoR1, and the resulting 5'-overhang filled by T4 DNA polymerase in the presence of 100 uM dNTPs (12° C. for 15 minutes). The reaction was terminated (75° C. for 20 minutes in the presence of 10 mM EDTA) and the restricted vector was column purified (QIAquick PCR purification kit, QIAGEN). The purified vector was then further restricted with NotI and gel purified (QIAquick gel extraction kit, QIAGEN). The PEP2-2-1-1 CAR construct fragment was first restricted with SmaI followed by NotI digestion (both at 25° C.). The restricted gBlock fragment was purified with a QIAquick PCR purification kit in accordance with manufacturer's instructions. The restricted vector was ligated with the CAR construct at a 3:1 molar ratio of insert to vector.

Cloning and Evaluation of pCDH-CAR Vector

Ligation mixes for each of the three CAR constructs described above were transformed into chemical competent SURE2 cells (Agilent) in accordance with the manufacturer's instructions. Briefly:

SURE2 cells were thawed on ice. Once thawed, the cells were gently mixed and 100 μl aliquots of cells were placed in pre-chilled 14 ml round bottom tubes;

2 μl of the β-Mercaptoethanol was added to each aliquot of cells;

The tubes were mixed and incubated on ice for 10 minutes, swirling gently every 2 minutes;

0.1-50 ng of each of the pCDH-CAR vectors was added to an aliquot of cells;

The aliquots were gently mixed, then incubate on ice for 30 minutes;

The tubes were heat-pulsed at 42° C. in a water bath for 30 seconds and then incubate on ice for 2 minutes;

0.9 ml of preheated (42° C.) NZY+ broth was added to each tube followed by incubation at 37° C. for 1 hour with agitation at 225-250 rpm;

Up to 200 μl of the transformation mixture was plated on LB agar plates containing antibiotic, followed by incubation at 37° C. overnight;

Colonies were picked and cultured further overnight;

Plasmid DNA was isolated from cultured clones with a Quicklyse miniprep kit (QIAGEN) and digested with EcoRI/NotI digestion to identify clones with the correctly sized CAR-pCDH vectors Following incubation of the transformed (SURE2) cells, 5 to 6 colonies of cells transformed with pCDH-CAR for each of the PEP2-2-1-1, PEP2-472-2 or PEP2-2-12 binding peptides were isolated and further incubated overnight. Plasmid DNA was isolated with a Quicklyse miniprep kit (QIAGEN) from each of the cultured colonies, and restricted with the EcoRI/NotI restriction enzymes. The restricted DNA was analysed via gel electrophoresis for appropriate sized restriction fragments.

Figure 13:
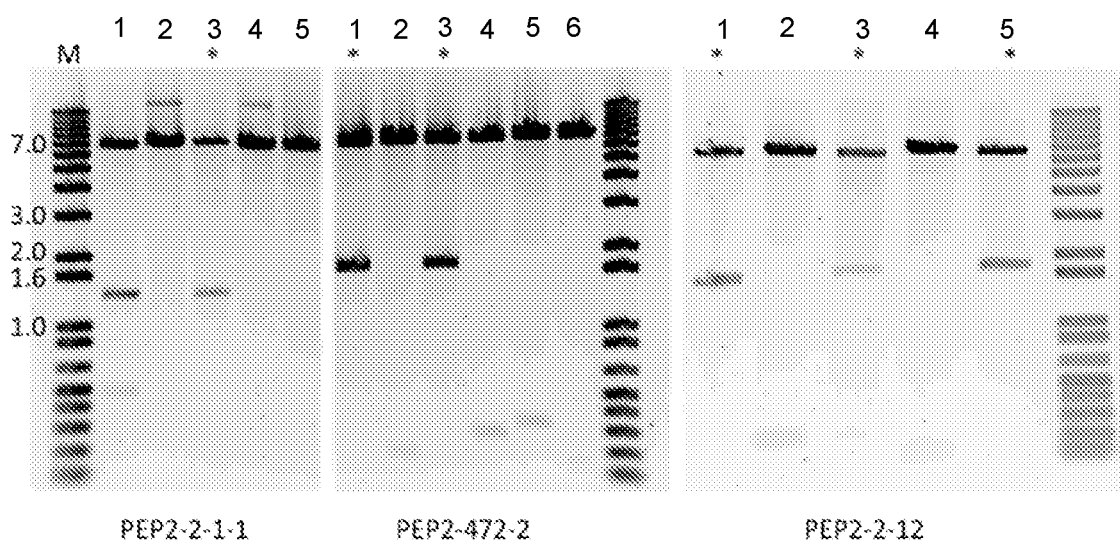
FIG. 13—An electrophoresis gel showing restriction fragments from EcoRI and Not I restricted DNA isolated from selected Sure 2 clones, transformed with the pCDH plasmid.

As shown in FIG. 13, colony 3 of the PEP2-2-1-1 pCDH-CAR construct, colonies 1 and 3 of the PEP2-472-2 pCDH-CAR construct and colonies 1, 3 and 5 of the PEP2-2-12 pCDH-CAR construct contained the appropriately sized restriction fragments.

Each selected clone was sequenced to confirm the integration of the CAR using the appropriate primers selected from Table 5.

TABLE 5

Primers used for confirmation of correct CAR construct in selected colonies

| Primer name | Sequence | SEQ ID NO |
|---|---|---|
| pCHD-CMV-For | GGTGGGAGGTCTATATAAGC | SEQ ID NO: 38 |
| pCHD-coGFP-Rev | TGATGCGGCACTCGATCTC | SEQ ID NO: 39 |
| 2-2-1-1-Rev | CTTCACGGAGTCTGCGTAG | SEQ ID NO: 40 |
| 2-2-1-1-For | TCTTGTCACTGTATCCAGTG | SEQ ID NO: 41 |
| 2-472-2-Rev | CGTATCTTCAGCTCTCAAGC | SEQ ID NO: 42 |
| 2-472-2-For | TGGTCCTTCAGTTTTCCTGT | SEQ ID NO: 43 |
| 2-12-2-Rev | CAGCTGTATCTTCTGCTC | SEQ ID NO: 44 |
| Com-For-1 | AGTGGGAGAGTAACGGACAG | SEQ ID NO: 45 |
| Com-For-2 | AGGGCCAGAATCAATTGTAC | SEQ ID NO: 46 |

Sequencing data for each selected colony was aligned to the in silico derived recombinant clone for each of the PEP2-2-1-1, PEP2-472-2 or PEP2-2-12 CAR constructs and appropriate constructs were verified for at least one of each of the selected colonies. Large scale Endotoxin free plasmid isolation of the verified clones was performed with a NucleoBond® Xtra Midi EF kit, Macherey-Nagel in accordance with the Manufacturer's instructions.

Construction and Verification of Viral Vectors

Lentivirus packaging was performed in transiently transfected Hek293T cells using Lipofectamine 2000 reagent (Invitrogen) as per a standard laboratory protocol (Brown, C. Y. et al. 2010. Robust, reversible gene knockdown using a single lentiviral short hairpin RNA vector. *Hum Gene Ther* 21, 1005-1017). Briefly:

12.5 ug of Lentiviral vector DNA was mixed with 3.75 ug of pMD2.g (VSV-G envelope expression vector), 6.25 ug of pRSV-Rev and 7.5 ug of pCMVdelta8.2 per transfection in a T75 cm flask using 75 ul of Lipofectin as per the manufacturer's protocol, and incubated overnight;

The following morning media was changed and virus containing supernatant was harvested 48 hours later;

Harvested supernatants were centrifuged at 300×g for 5 minutes before being filtered through a 0.45 um filter;

Virus particles from filtered supernatants were concentrated by ultracentrifugation (68,000×g for 90 minutes and 4° C., Beckman SW32 rotor). The supernatant was removed and the virus pellet resuspended gently in DMEM on ice;

100 ul virus aliquots were stored at −70° C. until needed.

Figure 14:
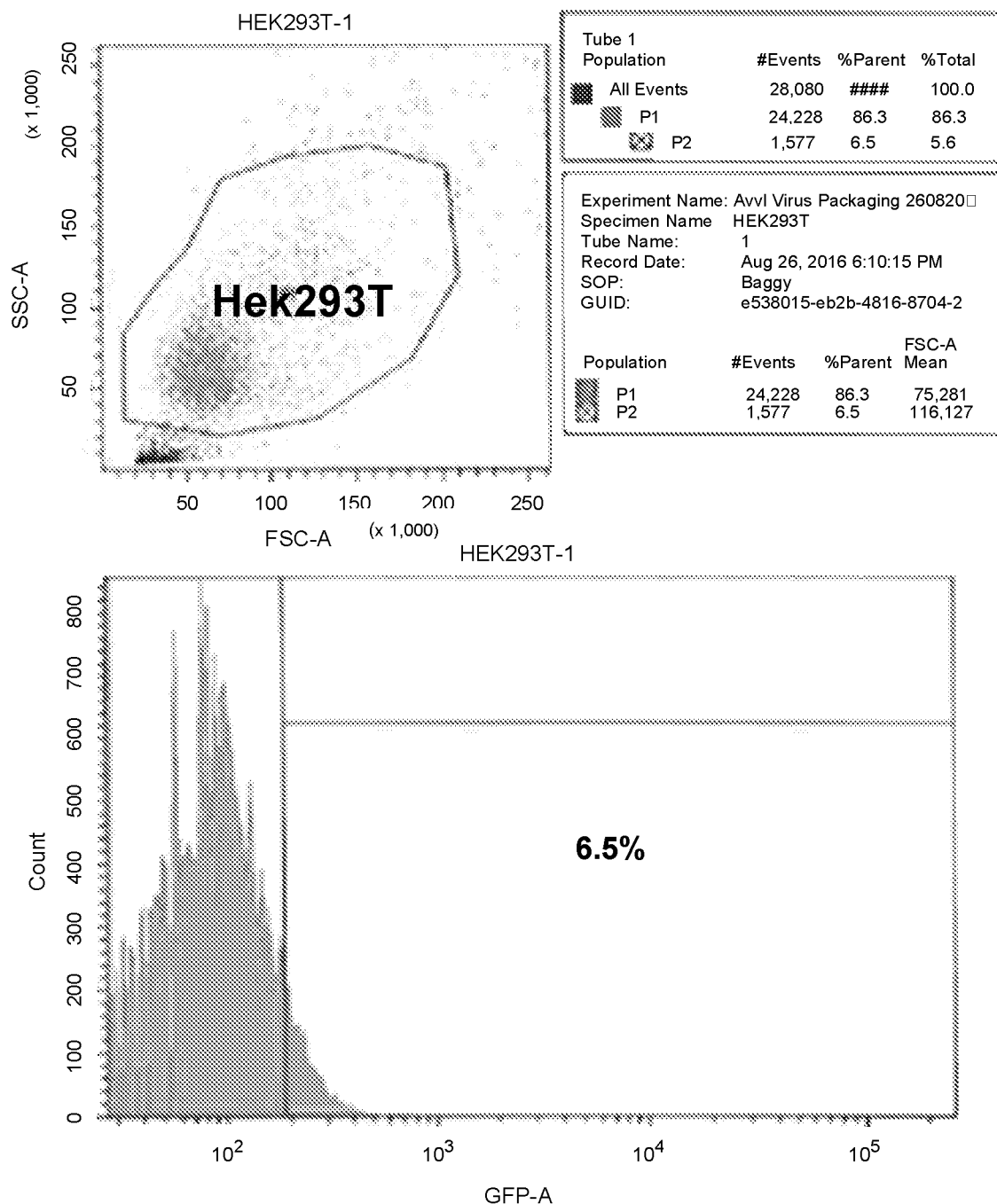
FIG. 14—FACS analysis of the efficiency of transfection of HEK293T cells.
Figure 14:
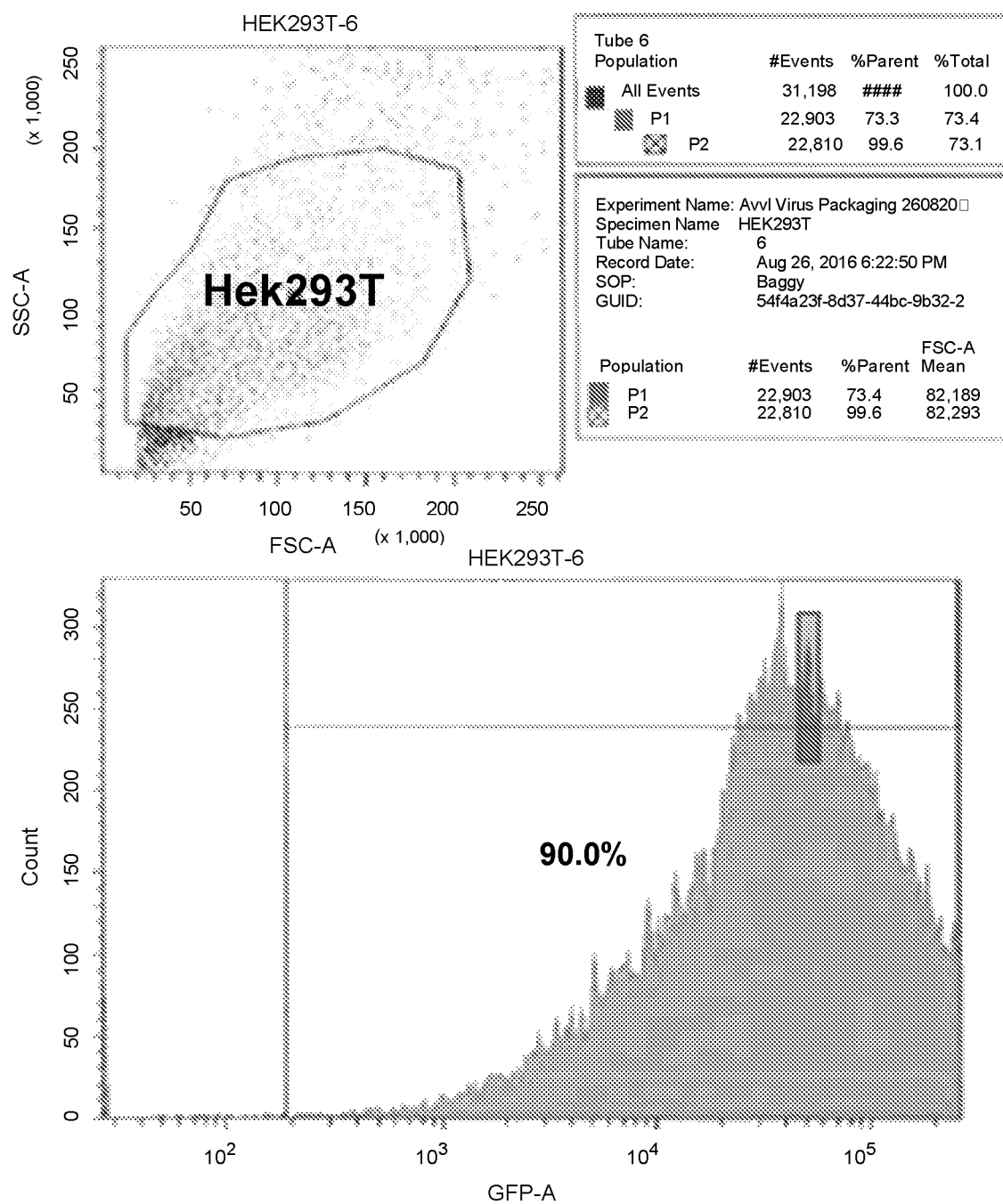

To assess the rate of virus transfection, transfected Hek293T cells were harvested and the percent of GFP positive cells (pCDH vector containing cells) was determined by flow cytometry. Representative results for Hek293T transfected with the LV-PEP2-472-2 packaging mix is shown in FIG. 14.

Figure 15:
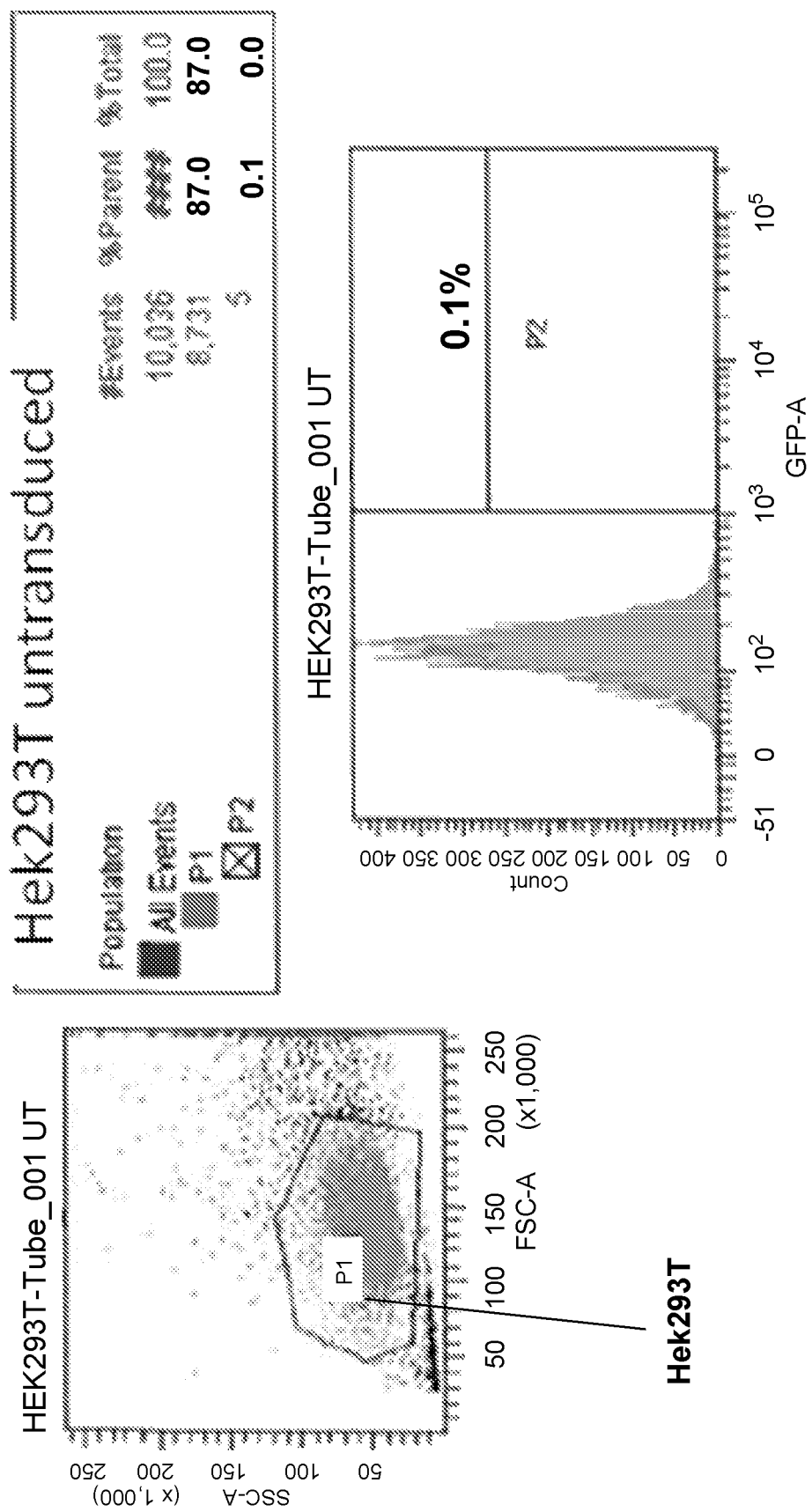
FIG. 15—Representative histograms of FACS analysis of lentiviral transduction efficiency.
Figure 15:
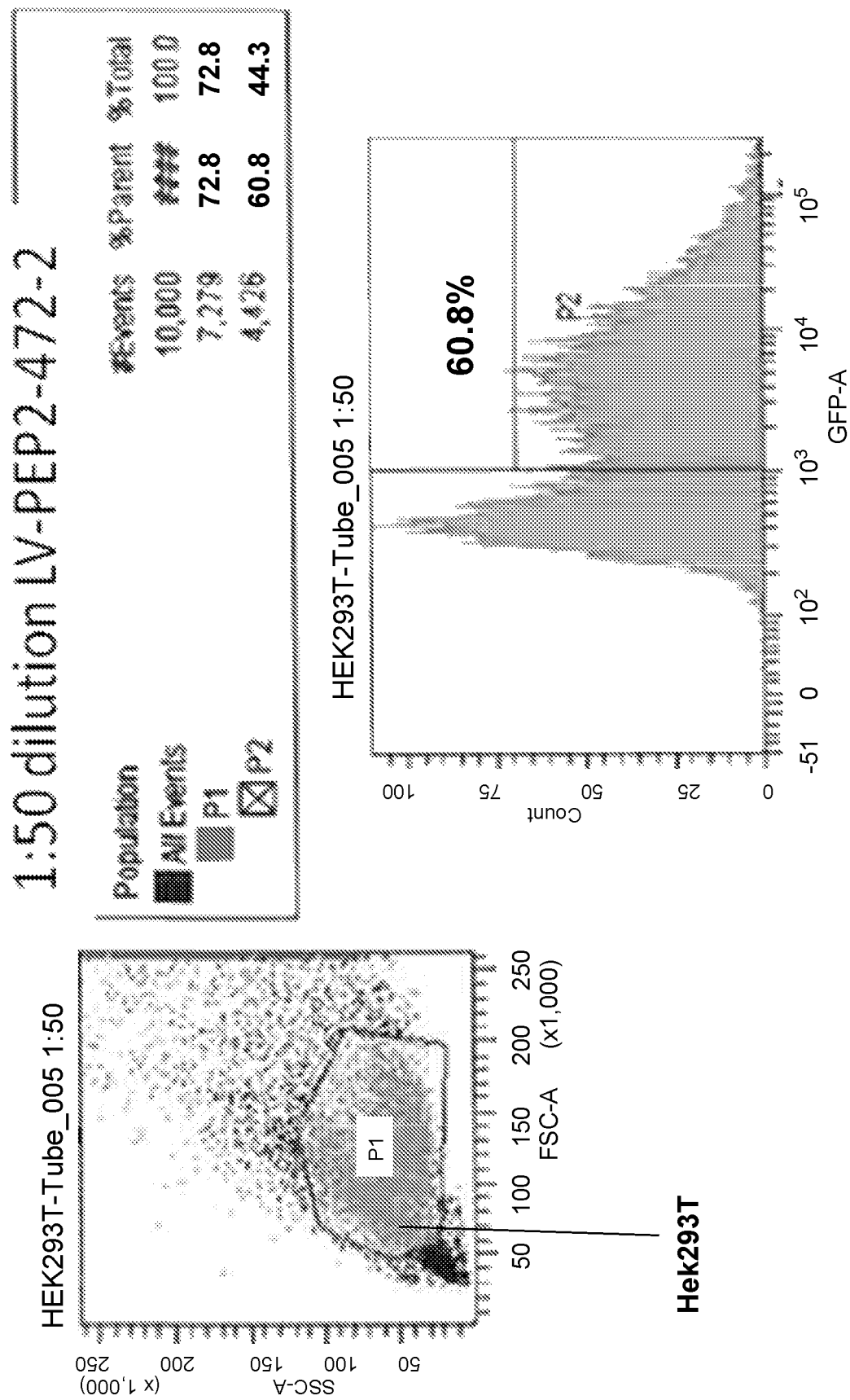
Figure 15:
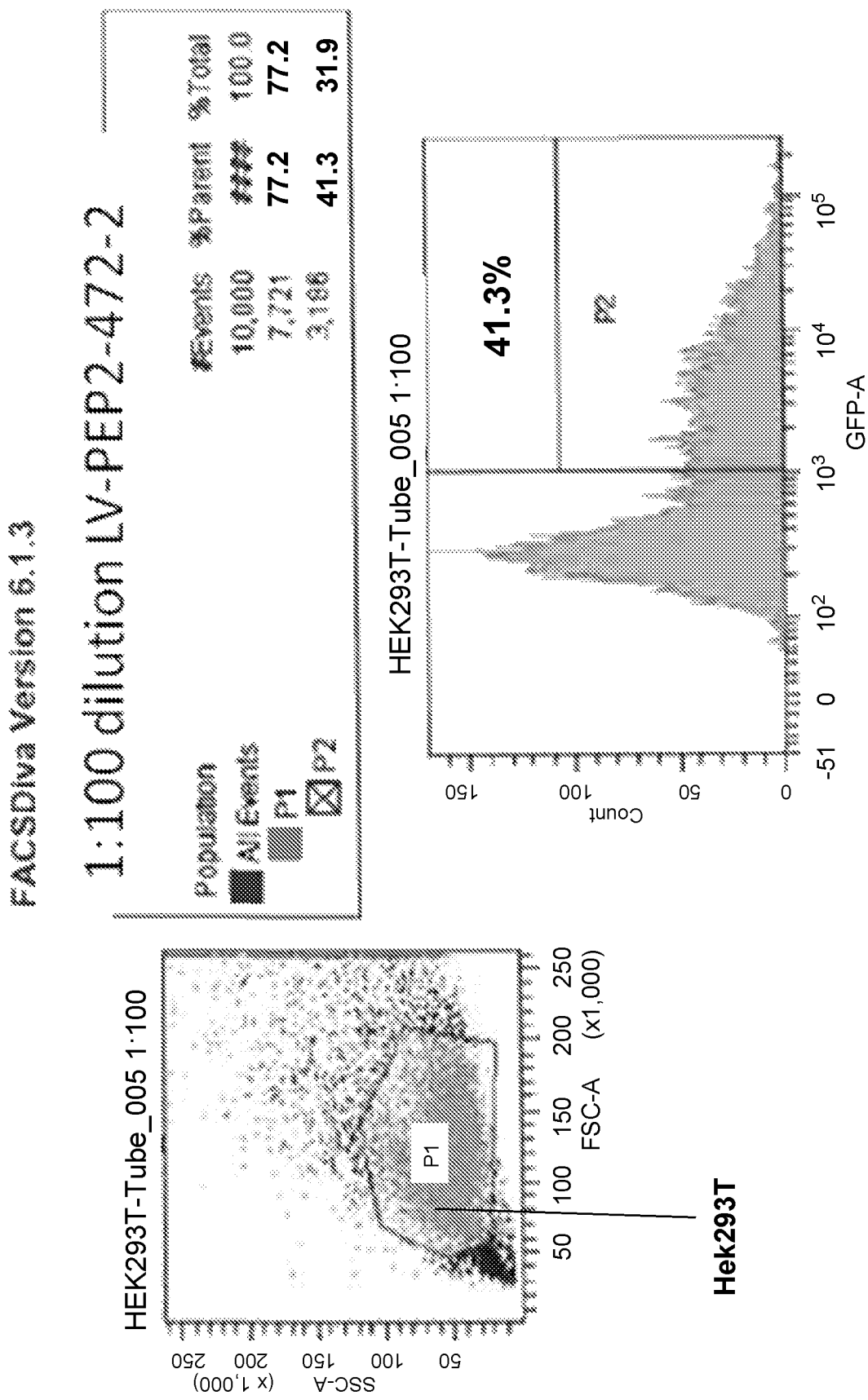

Viral titres were calculated by transduction of a known number of Hek293T cells with serial dilutions (1:50 and 1:100) of concentrated LV stock. Transductions were performed overnight in the presence of 8 ug/ml polybrene (Hexadimethrine bromide). The following day media containing virus and polybrene was replaced with fresh media, cells were harvested 24 hours later and the percentage of GFP positive cells determined by flow cytometry. Viral titres were calculated using the formula: Transduction units/ml (TU)=(F×C/V)×D where F=frequency of GFP+ cells (% GFP+/100), C=cell number at the time of virus addition, V=volume of transduction in mL and D=dilution factor. Representative flow data for LV-PEP2-472-2 transduction is shown in FIG. 15. The TU for each of the PEP2-2-1-1, PEP2-12-2 and PEP2-472-2 CAR viral vectors is provided in the Table 6 below.

TABLE 6

Transduction Units for Viral Vectors

| Lentiviral construct | Dilution Factor | Average % GFP+ cells | TU/ml |
|---|---|---|---|
| PEP2-2-1-1 | 50 | 31.15 | 4.14e6 |
| | 100 | 21.25 | 5.62e6 |
| PEP2-12-2 | 50 | 54.6 | 7.26e6 |
| | 100 | 33.15 | 8.82e6 |
| PEP2-472-2 | 50 | 62 | 8.25e6 |
| | 100 | 39.55 | 10.52e6 |

Screening for nf-P2X$_7$ CAR T Cell Function

Production of CD8 T Cells Expressing Anti-nf-P2X$_7$ CARs

Human CD8 cells were purified and transduced in accordance with the following method:

Human CD8 T cells were purified from mononuclear cells (MNCs) isolated from Buffy Coats from anonymous donors (Australia Red Cross blood service). MNCs were isolated using Ficoll-Paque™ density gradient media. CD8 T cells were purified from MNCs Dynabeads® Untouched™ Human CD8 T Cells Kit (Invitrogen) according manufacturer's instructions. The purity of isolated cells, as assessed by flow cytometry, was >85%.

2×10$^6$ purified cells were pre-incubated with CD3/CD28 beads (3:1 bead to cell ratio) and IL2 (500 U/ml) for 30 minutes prior to the addition of 1 to 2 multiplicity of infection (MOI) units of virus containing LV-PEP2-2-1-1, LV-PEP2-472-2 or an empty LV vector (GFP control virus) together with 8 ug/ml polybrene. Cells were incubated with virus for 16 hours before the virus containing media was removed. The remaining cells and beads were incubated in fresh media including IL2 for 40 hours before GFP fluorescence levels were analysis.

Figure 16:
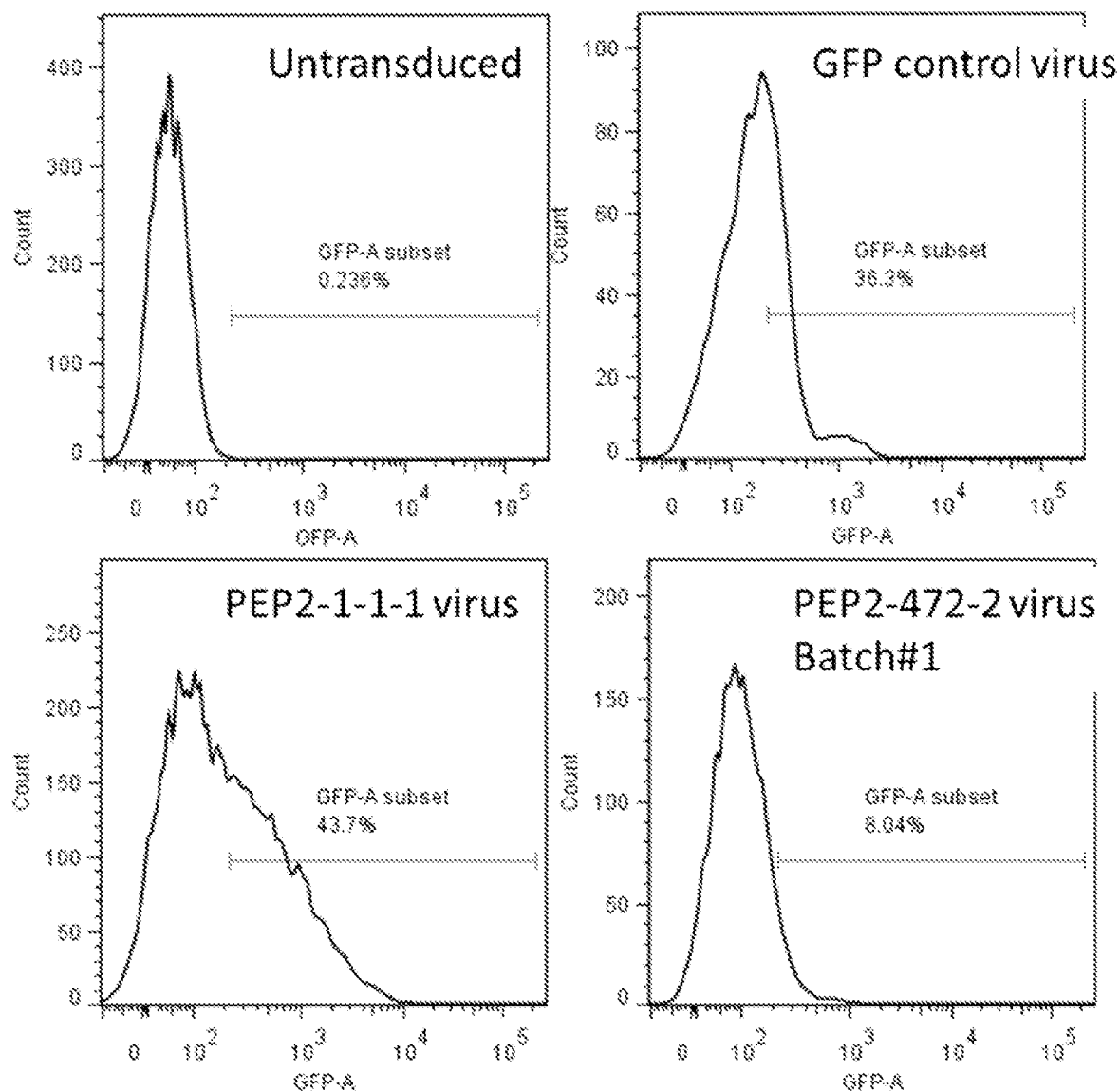
FIG. 16—FACS analysis of the percentage of transduced CD8 cells expressing GFP.

As illustrated in FIG. 16, between 8% and 43% of CD8 cells GFP+ indicating successful transduction.

Production of Target Cells Expressing Nf-P2X$_7$ or Wild-Type (WT) P2X$_7$ Receptors To assess the efficacy of CD8 cells expressing the anti-nf-P2X$_7$-CARs, Hek293T cells over-expressing either a non-functional P2X$_7$ receptor (having a K193A mutation) or a wild type extracellular domain of the P2X$_7$ receptor on their cell surface, were prepared.

EXD2_K193A (nf-P2X$_7$) and EXD2_WT (functional P2X$_7$) gBlock gene fragments (SEQ ID NOs: 47 and 48, respectively) were ordered from Integrated DNA technologies (IDT). The EXD2 domains were designed to be expressed in frame with DNA sequences encoding for a fusion protein consisting of the IgK-leader-HA-MYC-PDGFR-transmembrane domian from pDisplay (Invitrogen—FIG. 17). These fusion proteins were designed for surface expression. The EXD2_K193A and EXD2_WT gene fragments were cloned between the HA and MYC-epitope Tags to forma fusion gene blocks. Gateway attB1 and attB2 sequences were included at the 5′- and 3′-ends of the fusion gene blocks for cloning into the LV-416-IRES-puro vector (Clontech).

Cloning was performed using Gateway@ (ThermoFisher) and all steps were carried out following the manufacturer's protocol. Briefly:

First BP recombination reactions were performed between attB-flanked DNA fragments (EXD2_K193A, SEQ ID NO: 47 and EXD2_WT, SEQ ID NO: 48) and an attP containing pDONR-107 vector to generate an entry clone. The BP recombination reactions were used to transform chemically competent E. cloni®10G cells (Lucigen®) according to manufacturer's protocol;

Transformed cells were plated onto LB agar plates containing 50 ug/ml Kanamycin (Sigma) and incubated at 37° C. overnight;

Two clones from each plate were picked to prepare mini cultures (2 mL) in LB broth with kanamycin (SIGMA) (50 ug/ml). Followed by incubation at 37° C. overnight with agitation.

Figure 18:
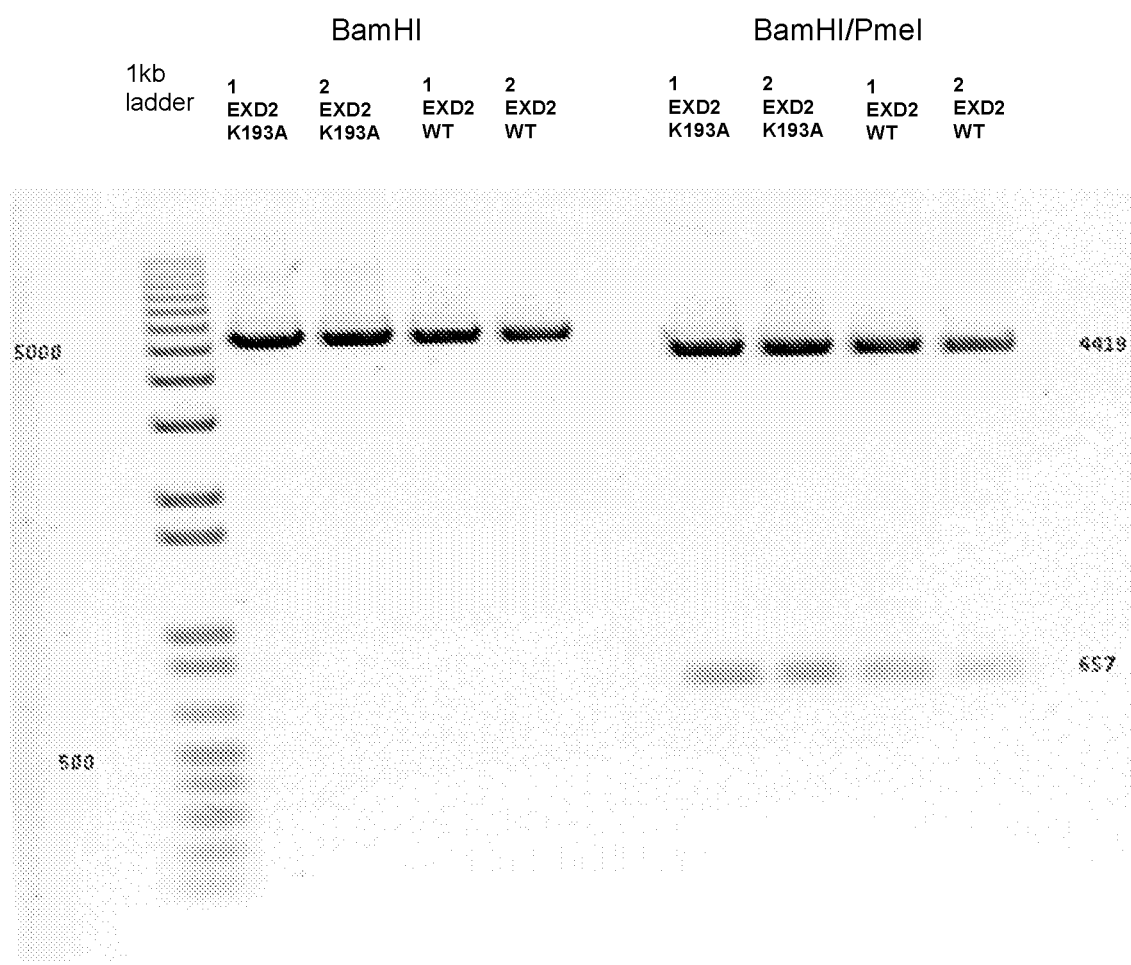
FIG. 18—An electrophoresis gel showing restriction fragments from Bam HI and Pmel restricted DNA isolated from selected E. cloni®10G clones transformed with EXD2_K193A or EXD2_WT containing pDONR-107 vectors.

Plasmid DNA was extracted the following day from the mini cultures using the QIAGEN QuickLyse miniprep kit;

A diagnostic Bam H1-HF (NEB) and PmeI (NEB) digests were performed to identify recombinant clones. Both the EXD2_K193A and EXD2_WT clones were confirmed to be digested correctly via Bam H1 and Bam H1/PmeI digestion followed by gel electrophoresis (FIG. 18).

One clone from each construct (EXD2_K193A and EXD2_WT) was chosen for the LR recombination reaction (as set forth below) to insert the EXD2_K193A and EXD2_WT constructs into a pLV-416 destination vector.

Figure 19:
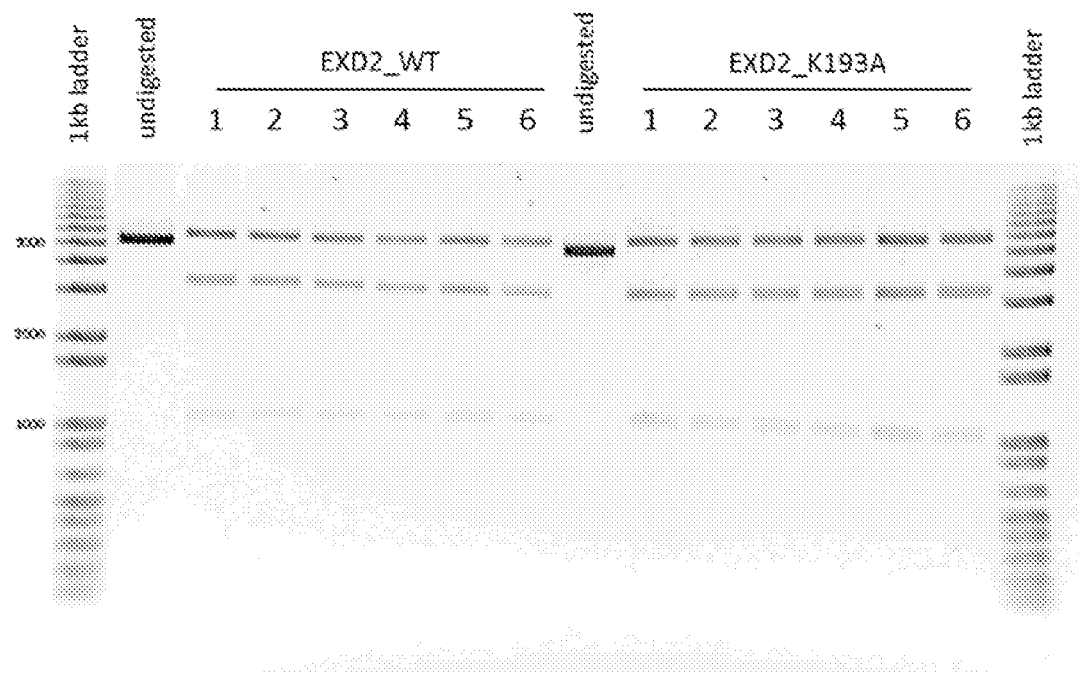
FIG. 19—An electrophoresis gel showing restriction fragments from Bam HI restricted DNA isolated from selected E. cloni®10G clones transformed with EXD2_K193A or EXD2_WT containing pLV-416 vectors.

Following selection of clones, LR recombination reactions were then performed to transfer each EXD2 insert from the pDONR-107 entry clone to the pLV-416 destination vector to create an expression vector. The final LR recombination reaction was used to transform chemically competent E. cloni®10G cells (Lucigen®) according to manufacturer's protocol. Briefly:

Transformed cells were plated onto LB agar plates containing 100 ug/ml Ampicillin (SIGMA) and incubated at 37° C. overnight;

Six clones from each plate were picked to prepare mini cultures (2 mL) in LB broth with Ampicillin (50 ug/ml), which were incubated at 37° C. overnight with agitation;

The following day plasmid DNA was isolated and Bam H1 digestion was performed to identify recombinant clones. Recombinant clones were identified by the presence of three bands of the appropriate size (3431, 1056 and 5844 bp—see FIG. 19). As can be seen in FIG. 19 all six selected clones from each plate provided the appropriate sized restriction fragments;

Two clones transduced with the pLV-416 constructs containing EXD2_K193A or EXD2_WT were sequenced with the primers set forth in Table 7 to confirm the constructs were correct.

TABLE 7

Primers Used for Confirmation of Correct EXD2_K193A and EXD2_WT Constructs in Selected Colonies

| Primer name | Sequence | SEQ ID NO |
|---|---|---|
| EXD-F1 primer | ACAAGCTGTACCAGCGGAAA | SEQ ID NO: 49 |
| EXD2-R1 primer | CACCACCACCTTAAAGGGCA | SEQ ID NO: 50 |
| EXD2-F1 primer | ACAAGCTGTACCAGCGGAAA | SEQ ID NO: 51 |

To produce viral particles for transduction of HEK293 cells, and the generation of a stable HEK293 cell line, expressing a functional or non-functional P2X$_7$ receptor, the following protocol was used:

HEK293 cells were plated ($7 \times 10^6$ cells per flask) a day prior to transfection.

HEK293T cells were transfected with Lentiviral packaging vectors and either pLV-416-EXD2 and pLV-416-EXD2_WT. To monitor transfection efficiency, a GFP expression plasmid (1 ug) was also included.

Following overnight incubation, the medium containing the transfection reagents was removed and replaced with 10 ml of fresh medium (DMEM with 10% FCS). 10 ml of media was harvested 24 hours later and stored in 2 ml aliquots at −80° C. until required. Another 10 ml of fresh medium (DMEM with 10% FCS) was added to the flasks which was harvested a further 24 hours later.

Viral particles were isolated from the harvested media by centrifuging the media at 1200 rpm followed by filtration through a 0.45 um filter. The filtered media, with virus particles, were used for transfection of HEK293 cells.

Figure 20:
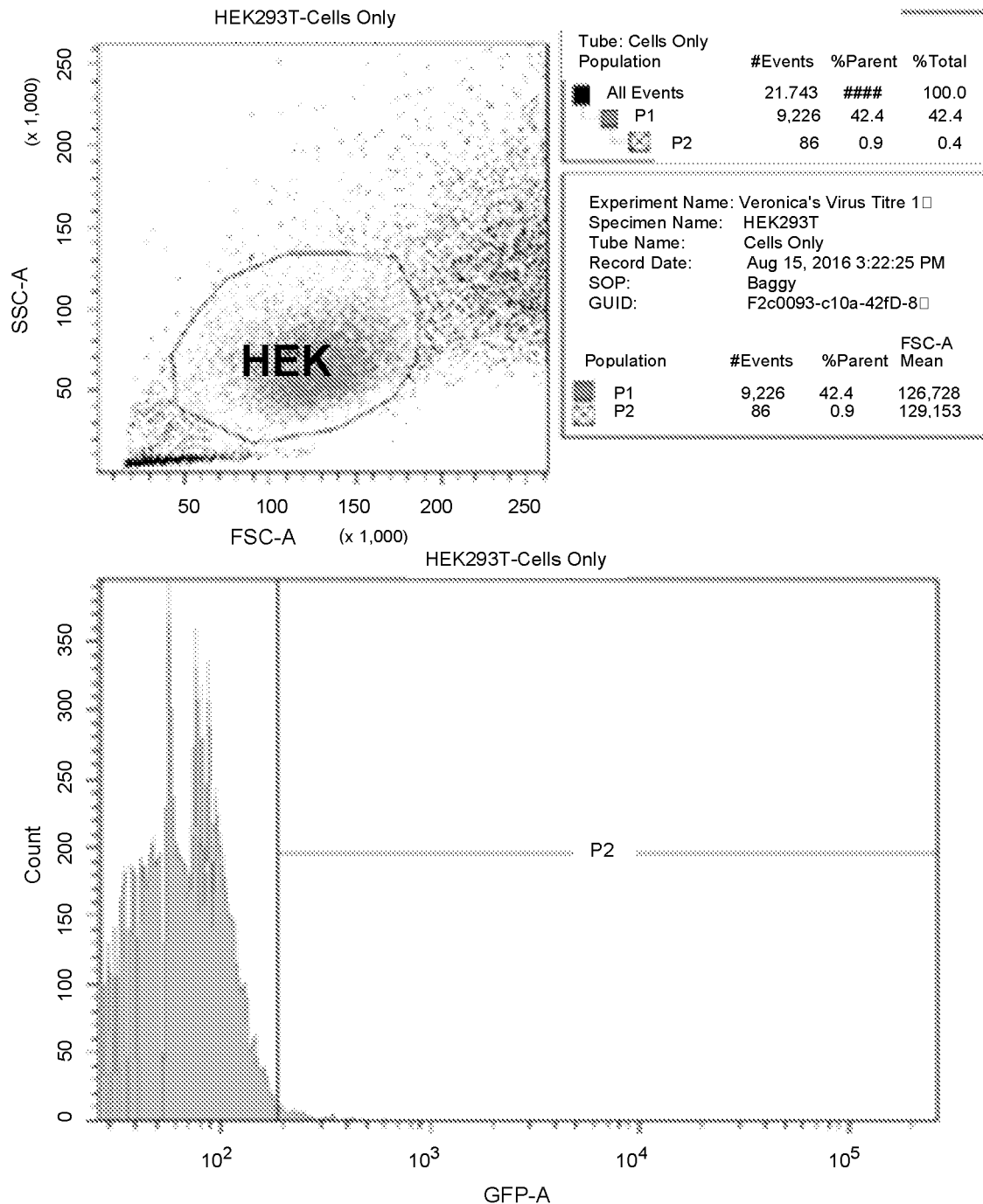
FIG. 20—FACS analysis of transduction of lentiviral packaging of HEK293 cells with pLV-416-EXD2_K193A and pLV-416-EXD2_WT.
Figure 20:
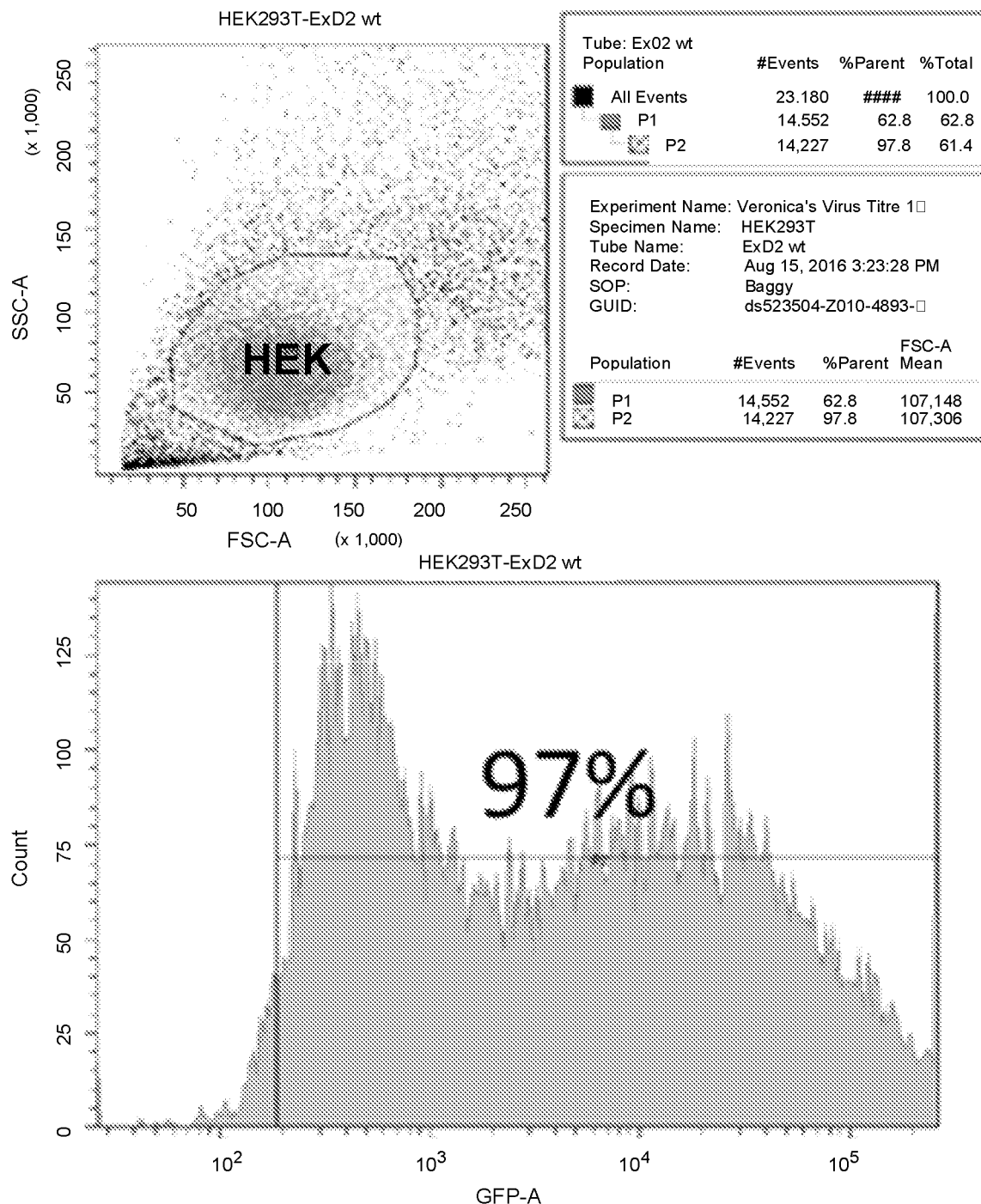
Figure 20:
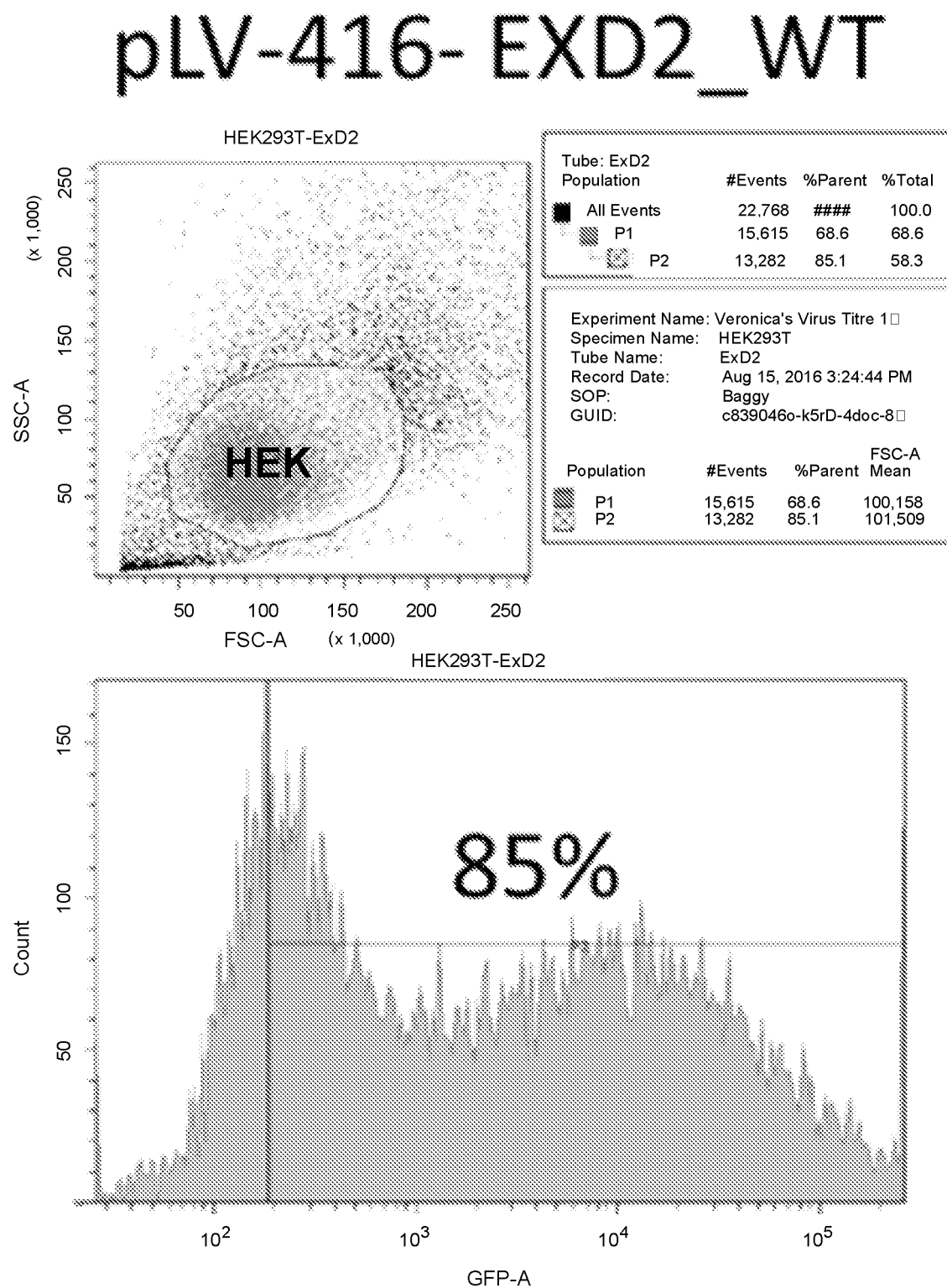

To assess transfection efficiency, cells were harvested following the removal of the second 10 ml of medium and the percentage of GFP positive cells was determined by flow cytometry. FIG. 20 illustrates that HEK293 cells were transfected with pLV-416-EXD2_K193A and pLV-416-EXD2_WT at an efficiency of 97% and 85%.

To generated stable HEK293 cells over-expressing the extracellular domain of functional and non-functional P2X$_7$ on their cell surface. The following protocol was used:

HEK293 cells were plated ($7 \times 10^5$ per flask) in T25 flasks a day prior to transduction.

The following day the medium was removed from each flask, and fresh media containing virus particles produced in accordance with the above protocol were added according to the ratios set out in Table 8;

Polybrene was added to each flask to a final concentration of 8 ug/mL.

TABLE 8

Transduction Protocol

| Virus particle | Media | Media with virus | Media | Media with virus | Media | Media with virus |
|---|---|---|---|---|---|---|
| pLV-416-EXD2 | 2.5 mL | 2.5 mL | 4 mL | 1 mL | 4.5 mL | 0.5 mL |
| pLV-416-EXD2_WT | 2.5 mL | 2.5 mL | 4 mL | 1 mL | 4.5 mL | 0.5 mL |
| Control LV-411-GFP | 4 mL | 1 mL (0.5 MOI) | | | | |
| Polybrene 20 mg/mL stock | 2 uL | | 2 uL | | 2 uL | |
| Un-transduced | 5 mL | | | | | |

24 h after the transduction, the medium was removed from each flask and fresh medium (DMEM with 10% FCS) supplemented with 1600 ug/mL G418 was added to all flasks except the flask containing control Lentivirus expressing GFP (LV-411-GFP).

Figure 21:
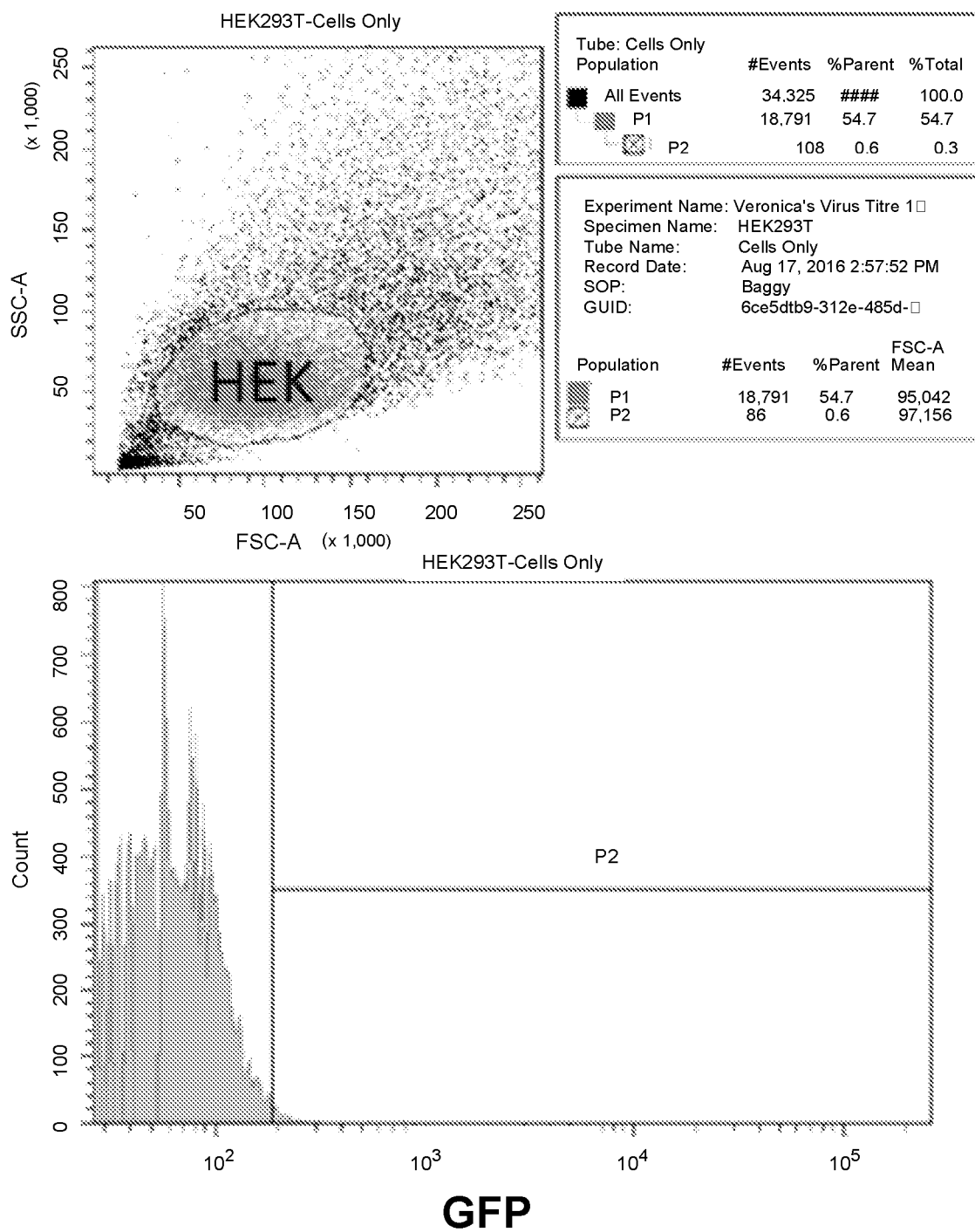
FIG. 21—FACS analysis of transduction of HEK293 with lentivirus containing either pLV-416-EXD2_K193A or pLV-416-EXD2_WT constructs.
Figure 21:
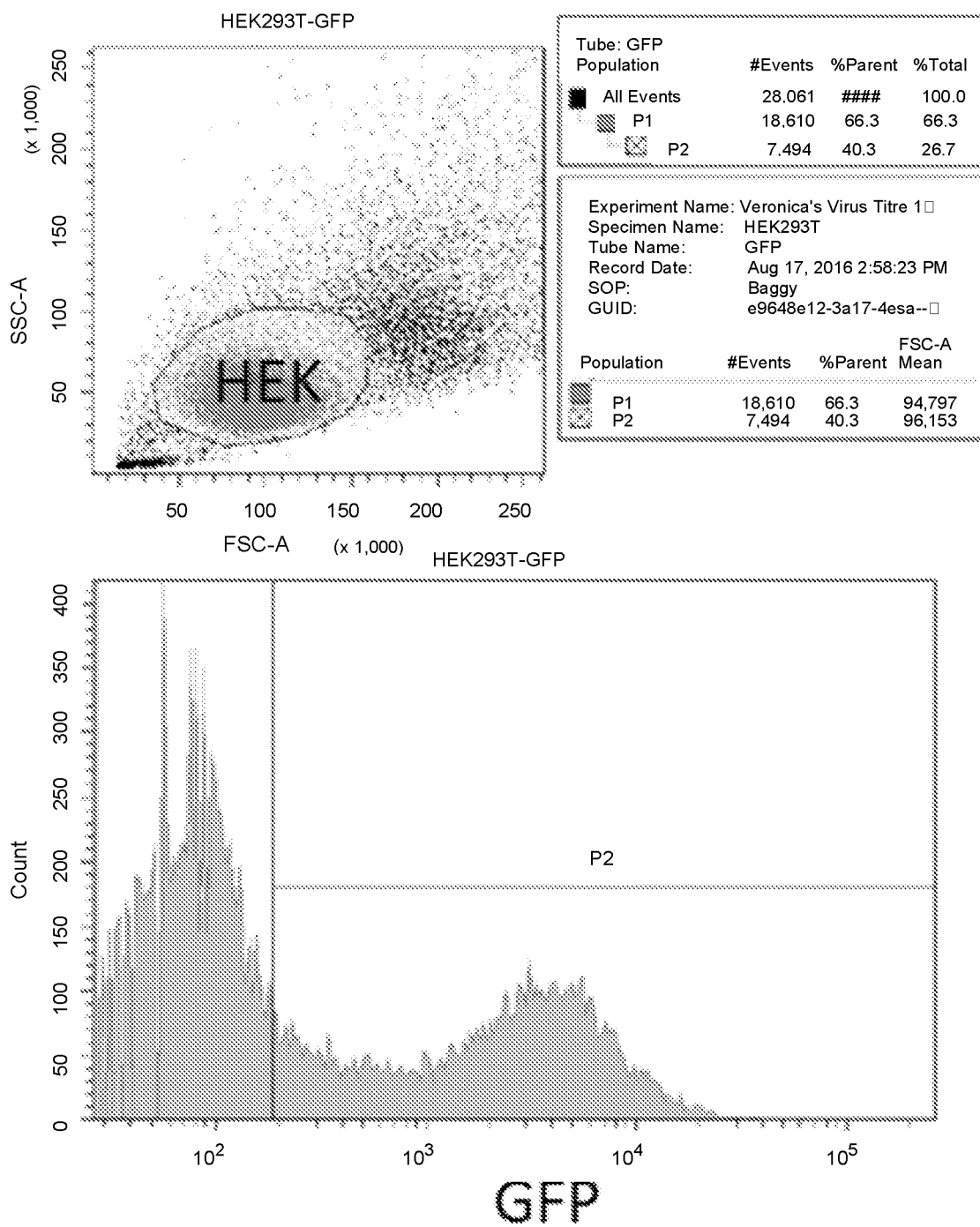

HEK293T cells transduced with control pLV-411-GFP virus were monitored for GFP expression 72 hours post-transduction (see FIG. 21);

All un-transduced cells died 4 days after culturing with G418 supplemented media. The transduced cell lines continued to grow normally with G418 in media.

The extracellular domain of the transfected $P2X_7$ receptors contains HA- and MYC-epitope tags. Therefore, these cells can be stained with monoclonal antibodies against HA- and MYC- to confirm surface expression of the extracellular domain by flow cytometry.

Screening for CAR T Cell Function

To assess the functionality of the nf-P2X7-CARs, CD8 cells transduced with each of the PEP2-2-1-1 or PEP2-472-2 CAR constructs (as prepared above) were co-incubated for 4 hours in a 96-well round-bottom culture plate at 1:1 ratio with $1 \times 10^4$ target cells expressing an nf-$P2X_7$ receptor (as prepared above) and MDA-MB-231 breast cancer cells, which express a non-functional $P2X_7$ receptor (231 $P2X_7$ cells).

The percentage of cytotoxicity was determined via a in a CytoTox 96® Non-Radioactive Cytotoxicity Assay (Promega, Madison, Wisconsin, USA) in accordance with the manufacturer's instructions. Briefly:

- 45 mins prior to 4 hours, 10 μl of Lysis Solution (10×) was added to each well for every 100 μl of target cells;
- After a further 45 minutes the plates were centrifuge at 250×g for 4 minutes;
- 50 μl aliquots were taken from each well and transferred to a 96-well flat-bottom plate;
- 50 μl of CytoTox 96® Reagent was added to each well of the plate containing the transferred aliquots, and the plate was cover with foil for 30 minutes at room temperature;
- Following 30 minutes, 50 μl of Stop Solution was added to each well and the absorbance at 490 nm was read from each well.

The absorbance values for each well was corrected in accordance with the manufacturer's instructions and the percentage of cytotoxicity was calculated using the following formula, normalised to empty vector transduced T cells, to give a fold change in cell killing.

$$\% \text{ Cytotoxicity} = \frac{\text{Experimental} - \text{Effector Spontaneous} - \text{Target Spontaneous}}{\text{Target Maximum} - \text{Target Spontaneous}} * 100$$

As demonstrated in FIG. 22A, both PEP2-2-1-1 and PEP2-472-2 CAR expressing CD8 T cell killed approximately 15 and 11-fold (respectively) more HEK cells expressing a non-functional $P2X_7$ receptor than CD8 cells transduced with an empty vector. Furthermore, as shown in FIG. 22B, PEP2-2-1-1 and PEP2-472-2 CAR expressing CD8 T cell killed approximately 2.5 and 2.25-fold (respectively) more 231 $P2X_7$ cells than CD8 cells transduced with an empty vector.

All methods described herein can be performed in any suitable order unless indicated otherwise herein or clearly contradicted by context. The use of any and all examples, or exemplary language (e.g., "such as") provided herein, is intended merely to better illuminate the example embodiments and does not pose a limitation on the scope of the claimed invention unless otherwise claimed. No language in the specification should be construed as indicating any non-claimed element as essential.

The description provided herein is in relation to several embodiments which may share common characteristics and features. It is to be understood that one or more features of one embodiment may be combinable with one or more features of the other embodiments. In addition, a single feature or combination of features of the embodiments may constitute additional embodiments.

The subject headings used herein are included only for the ease of reference of the reader and should not be used to limit the subject matter found throughout the disclosure or the claims. The subject headings should not be used in construing the scope of the claims or the claim limitations.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

Also, it is to be noted that, as used herein, the singular forms "a", "an" and "the" include plural aspects unless the context already dictates otherwise.

Future patent applications may be filed on the basis of the present application, for example by claiming priority from the present application, by claiming a divisional status and/or by claiming a continuation status. It is to be understood that the following claims are not intended to limit the scope of what may be claimed in any such future application.

We claim:

1. A chimeric antigen receptor comprising:
An antigen-recognition domain that binds to a dysfunctional P2X7 receptor but not a functional P2X7 receptor;
a transmembrane domain; and
a signalling domain comprising an intracellular signalling portion of an activation receptor and an intracellular signalling portion of a co-stimulatory receptor;
wherein the antigen recognition domain comprises complementarity-determining region 1(CDR1), CDR2 and CDR3 from the heavy chain of an antibody, wherein the antigen recognition domain comprises:
1. (a) CDR1 comprising an amino acid sequence of residues 30 to 35 of SEQ ID NO:32; (b) CDR2 comprising an amino acid sequence of residues 50 to 67 of SEQ ID NO: 32; and (c) CDR3 comprising an amino acid sequence of residues 98 to 108 of SEQ ID NO: 32;
2. (a) CDR1 comprising an amino acid sequence of residues 30 to 35 of SEQ ID NO: 33; (b) CDR2 comprising an amino acid sequence of residues 50 to 67 of SEQ ID NO: 33; and (c) CDR3 comprising an amino acid sequence of residues 98 to 108 of SEQ ID NO: 33;
3. (a) CDR1 comprising an amino acid sequence of residues 30 to 35 of SEQ ID NO: 10; (b) CDR2 comprising an amino acid sequence of residues 50 to 67 of SEQ ID NO: 10; and (c) CDR3 comprising an amino acid sequence of residues 98 to 108 of SEQ ID NO: 10; or
4. (a) CDR1 comprising an amino acid sequence of residues 30 to 35 of SEQ ID NO: 34; (b) CDR2 comprising an amino acid sequence of residues 50 to 67 of SEQ ID NO: 34; and (c) CDR3 comprising an amino acid sequence of residues 98 to 108 of SEQ ID NO: 34.

2. The chimeric antigen receptor according to claim 1, wherein the antigen recognition domain comprises:
a) CDR1 comprising an amino acid sequence of residues 30 to 35 of SEQ ID NO:32;
b) CDR2 comprising an amino acid sequence of residues 50 to 67 of SEQ ID NO: 32; and c) CDR3 comprising an amino acid sequence of residues 98 to 108 of SEQ ID NO: 32.

3. The chimeric antigen receptor according to claim 1, wherein the antigen recognition domain comprises:
a) CDR1 comprising an amino acid sequence of residues 30 to 35 of SEQ ID NO: 33;
b) CDR2 comprising an amino acid sequence of residues 50 to 67 of SEQ ID NO: 33; and
c) CDR3 comprising an amino acid sequence of residues 98 to 108 of SEQ ID NO: 33.

4. The chimeric antigen receptor according to claim 1, wherein the antigen recognition domain comprises:
a) CDR1 comprising an amino acid sequence of residues 30 to 35 of SEQ ID NO: 10;
b) CDR2 comprising an amino acid sequence of residues 50 to 67 of SEQ ID NO: 10; and
c) CDR3 comprising an amino acid sequence of residues 98 to 108 of SEQ ID NO: 10.

5. The chimeric antigen receptor according to claim 1, wherein the antigen recognition domain comprises:
a) CDR1 comprising an amino acid sequence of residues 30 to 35 of SEQ ID NO: 34;
b) CDR2 comprising an amino acid sequence of residues 50 to 67 of SEQ ID NO: 34; and
c) CDR3 comprising an amino acid sequence of residues 98 to 108 of SEQ ID NO: 34.

6. The chimeric antigen receptor according to claim 1 wherein the antigen-recognition domain is a dAb, or sdAb.

7. The chimeric antigen receptor according to claim 1, wherein the antigen-recognition domain is multivalent.

8. The chimeric antigen receptor according to claim 7, wherein multivalent is divalent or trivalent.

9. The chimeric antigen receptor according to claim 1, comprising the amino acid sequence of SEQ ID NO: 26, 27, 52, 53 or 54.

10. The chimeric antigen receptor according to claim 1, comprising the amino acid sequence of SEQ ID NO: 52.

11. The chimeric antigen receptor according to claim 1, comprising the amino acid sequence of SEQ ID NO: 53.

12. The chimeric antigen receptor according to claim 1, comprising the amino acid sequence of SEQ ID NO: 54.

13. The chimeric antigen receptor according to claim 1, wherein the activation receptor is a portion of CD3-ζ and wherein the co-stimulatory receptor is selected from the group consisting of CD27, CD28, CD30, CD40, DAP10, OX40, 4-1BB and ICOS.

14. A nucleic acid molecule comprising a nucleotide sequence encoding the chimeric antigen receptor according to claim 1.

15. A viral vector for viral transduction of a host cell comprising a nucleic acid according to claim 14.

16. A genetically modified cell, the cell including the chimeric antigen receptor according to claim 1.

17. A genetically modified cell according to claim 16, wherein the cell is a leukocyte, a Peripheral Blood Mononuclear Cell (PBMC), a lymphocyte, a T cell, a CD4+ T cell, a CD8+ T cell, a natural killer cell or a natural killer T cell.

18. A genetically modified cell according to claim 16, wherein the cell is a CD8+ T cell.

19. A method of killing a cell expressing a dysfunctional $P2X_7$ receptor, the method comprising exposing the cell expressing a dysfunctional $P2X_7$ receptor to the genetically modified cell according to claim 18.

20. A method of treating cancer in a subject, comprising administering a genetically modified cell according to claim 18 to a subject in need thereof.

21. A method of killing a cell expressing a dysfunctional $P2X_7$ receptor, wherein the cell expressing a dysfunctional $P2X_7$ receptor is a cancer cell, the method comprising exposing the cell expressing a dysfunctional $P2X_7$ receptor to the genetically modified cell according to claim 18.

22. A method according to claim 21, wherein the cancer cell is selected from one or more of; brain cancer, oesophageal cancer, mouth cancer, tongue cancer, thyroid cancer, lung cancer, stomach cancer, pancreatic cancer, kidney cancer, colon cancer, rectal cancer, prostate cancer, bladder cancer, cervical cancer, epithelial cell cancers, skin cancer, leukaemia, lymphoma, myeloma, breast cancer, ovarian cancer, endometrial cancer and testicular cancer, preferably wherein the cancer cell is selected from one or more of; lung cancer, oesophageal cancer, stomach cancer, colon cancer, prostate cancer, bladder cancer, cervical cancer, vaginal cancers, epithelial cell cancers, skin cancer, blood-related cancers, breast cancer, endometrial cancer, uterine cancer and testicular cancer.

23. A pharmaceutical composition including a chimeric antigen receptor according to claim 1 and a pharmaceutically acceptable carrier.

24. The chimeric antigen receptor according to claim 1, wherein the transmembrane region comprises an amino acid sequence derived from the CD28 co-stimulatory receptor.

25. The chimeric antigen receptor according to claim 1, wherein the activation receptor is a portion of CD3-ζ and wherein the co-stimulatory receptor is 4-1BB.

26. The chimeric antigen receptor according to claim 7, wherein the activation receptor is a portion of CD3-ζ and wherein the co-stimulatory receptor is OX40.

27. The chimeric antigen receptor according to claim 1, wherein the transmembrane region comprises an amino acid sequence derived from the CD28 co-stimulatory receptor.

28. The chimeric antigen receptor according to claim 1,
wherein the transmembrane region comprises an amino acid sequence derived from the CD28 co-stimulatory receptor; and
wherein the signalling domain comprises an amino acid sequence of a portion of CD3-ζ and the amino acid sequence of a co-stimulatory receptor selected from 4-1BB or OX40.

29. The chimeric antigen receptor according to claim 1, wherein the dysfunctional P2X7 receptor has a reduced capacity for binding to ATP compared to a wildtype (functional) $P2X_7$ receptor.

* * * * *